(12) United States Patent
Matsuoka et al.

(10) Patent No.: US 10,756,394 B2
(45) Date of Patent: Aug. 25, 2020

(54) NONAQUEOUS ELECTROLYTE AND NONAQUEOUS SECONDARY BATTERY

(71) Applicant: Asahi Kasei Kabushiki Kaisha, Tokyo (JP)

(72) Inventors: Naoki Matsuoka, Tokyo (JP); Akira Yoshino, Tokyo (JP); Yutaka Natsume, Tokyo (JP); Mitsuhiro Kishimi, Osaka (JP); Hirokazu Kamine, Osaka (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 171 days.

(21) Appl. No.: 15/558,272

(22) PCT Filed: Mar. 30, 2016

(86) PCT No.: PCT/JP2016/060453
§ 371 (c)(1),
(2) Date: Sep. 14, 2017

(87) PCT Pub. No.: WO2016/159117
PCT Pub. Date: Oct. 6, 2016

(65) Prior Publication Data
US 2018/0062213 A1    Mar. 1, 2018

(30) Foreign Application Priority Data

Mar. 31, 2015   (JP) ................... 2015-073052

(51) Int. Cl.
*H01M 10/42*     (2006.01)
*H01M 10/0568*   (2010.01)
(Continued)

(52) U.S. Cl.
CPC ...... *H01M 10/4235* (2013.01); *C07D 235/06* (2013.01); *C07D 235/22* (2013.01);
(Continued)

(58) Field of Classification Search
None
See application file for complete search history.

(56) References Cited

U.S. PATENT DOCUMENTS

2007/0224516 A1* 9/2007 Deguchi ............... H01M 2/16
                                                   429/339
2007/0231705 A1 10/2007 Ohzuku et al.
(Continued)

FOREIGN PATENT DOCUMENTS

EP    1018775 A1    7/2000
EP    2573853 A1    3/2013
(Continued)

OTHER PUBLICATIONS

Machine Translation of JP 2002-231305 (Year: 2002).*
(Continued)

*Primary Examiner* — Wyatt P McConnell
(74) *Attorney, Agent, or Firm* — Morgan, Lewis & Bockius LLP

(57) ABSTRACT

The purpose of the present invention is to provide a nonaqueous electrolyte that contains acetonitrile having an excellent balance between viscosity and the dielectric constant and a fluorine-containing inorganic lithium salt, wherein the generation of complex cations comprising a transition metal and acetonitrile is suppressed, excellent load characteristics are exhibited, and increases in internal resistance upon repeated charge/discharge cycles are suppressed; a further purpose of the present invention is to provide a nonaqueous secondary battery. The present invention relates to a nonaqueous electrolyte which contains: a nonaqueous solvent comprising acetonitrile; a fluorine-containing inorganic lithium salt; and a specific nitrogenous cyclic compound typified by benzotriazole.

8 Claims, 3 Drawing Sheets

(51) Int. Cl.
  H01M 10/0569 (2010.01)
  H01M 10/0567 (2010.01)
  H01M 10/0525 (2010.01)
  C07D 235/06 (2006.01)
  C07D 235/22 (2006.01)
  C07D 401/04 (2006.01)
  C07D 401/12 (2006.01)
  C07F 7/08 (2006.01)
  C07F 7/10 (2006.01)
  H01M 4/505 (2010.01)
  H01M 4/525 (2010.01)
  H01M 4/587 (2010.01)

(52) U.S. Cl.
  CPC ......... *C07D 401/04* (2013.01); *C07D 401/12* (2013.01); *C07F 7/0816* (2013.01); *C07F 7/10* (2013.01); *H01M 4/505* (2013.01); *H01M 4/525* (2013.01); *H01M 4/587* (2013.01); *H01M 10/0525* (2013.01); *H01M 10/0567* (2013.01); *H01M 10/0568* (2013.01); *H01M 10/0569* (2013.01); *H01M 2010/4292* (2013.01); *H01M 2300/0028* (2013.01); *Y02T 10/7011* (2013.01)

(56) References Cited

U.S. PATENT DOCUMENTS

| | | | |
|---|---|---|---|
| 2013/0078533 A1* | 3/2013 | Kang | H01M 10/0525 429/342 |
| 2013/0164633 A1 | 6/2013 | Takami et al. | |
| 2013/0224535 A1 | 8/2013 | Matsuoka et al. | |
| 2013/0244116 A1* | 9/2013 | Watanabe | H01M 4/133 429/231.8 |
| 2014/0160631 A1 | 6/2014 | Choi et al. | |
| 2014/0255796 A1 | 9/2014 | Matsuoka et al. | |
| 2015/0050563 A1 | 2/2015 | Yamada et al. | |

FOREIGN PATENT DOCUMENTS

| | | |
|---|---|---|
| EP | 2634854 A1 | 9/2013 |
| JP | H04-351860 A | 12/1992 |
| JP | 2002-231305 A | 8/2002 |
| JP | 2003-123837 A | 4/2003 |
| JP | 2004-111349 A | 4/2004 |
| JP | 2007-273405 A | 10/2007 |
| JP | 2009-021134 A | 1/2009 |
| JP | 2014-116586 A | 6/2014 |
| JP | 2014-241198 A | 12/2014 |
| WO | 2012/057311 A9 | 5/2012 |
| WO | 2013/062056 A1 | 5/2013 |
| WO | 2013/146714 A1 | 10/2013 |

OTHER PUBLICATIONS

Office Action issued in corresponding European Patent Application No. 16772998.7 dated Jul. 18, 2018.
Partial Supplementary European Search Report issued in corresponding European Patent Application No. 16772998.7 dated Dec. 15, 2017.
Supplementary European Search Report issued in corresponding European Patent Application No. 16772998.7 dated Feb. 12, 2018.
International Search Report issued in corresponding International Patent Application No. PCT/JP2016/060453 dated Jul. 5, 2016.
Written Opinion issued in corresponding International Patent Application No. PCT/JP2016/060453 dated Jul. 5, 2016.
International Preliminary Report on Patentability issued in corresponding International Patent Application No. PCT/JP2016/060453 dated Oct. 12, 2017.
Extended European Search Report issued in related European Patent Application No. 18208567.0 dated Jan. 23, 2019.

* cited by examiner

NONAQUEOUS ELECTROLYTE AND NONAQUEOUS SECONDARY BATTERY

TECHNICAL FIELD

The present invention relates to a non-aqueous electrolyte solution and a non-aqueous secondary battery.

BACKGROUND ART

The non-aqueous secondary battery including a lithium ion secondary battery has big characteristics in light weight, high energy and long life time, and thus has been widely used as a power source of various mobile electronic devices. In recent years, its application has been expanding to industrial use represented by a power tool, such as an electromotive tool, etc.; vehicle use, such as electric vehicles, electromotive bicycles, etc. It has been noticed further in a power storage field, such as a housing battery system, etc.

As an electrolyte solution for the lithium ion secondary battery operable at normal temperature, use of the non-aqueous electrolyte solution is desirable in view of practical use. A combination of, for example, a highly dielectric solvent, such as a cyclic carbonate ester, and a low viscosity solvent, such as a lower linear carbonate ester, is exemplified as a general solvent. However, a normal highly-dielectric solvent has a high melting point, as well, as may cause deterioration of load characteristics (rate characteristics) and low-temperature characteristics of the non-aqueous electrolyte solution depending on type of an electrolyte salt used in the non-aqueous electrolyte solution.

As one type of a solvent to overcome such a problem, nitrile-based solvents superior in balance between viscosity and dielectric constant have been proposed. Among them, acetonitrile has high potential as a solvent used in the electrolyte solution of the lithium ion secondary battery. However, acetonitrile has fatal defect of being reductively and electrochemically decomposed at a negative electrode, therefore exertion of practical performance has not been attained. Several improvement ideas have been proposed against this problem.

Main improvement ideas that have been proposed up to now are classified to the following three.
(1) Method for Protecting Negative Electrode and Suppressing Reductive Decomposition of Acetonitrile by Combination of Specific Electrolyte Salt and Additives, etc.

For example, in PATENT LITERATURE 1 and 2, there has been reported the electrolyte solution where influence of reductive decomposition of acetonitrile is reduced by combination of acetonitrile, as a solvent, with a specific electrolyte salt and additives. In addition, at the dawn of the lithium ion secondary battery, there has also been reported the electrolyte solution containing a solvent obtainable by only diluting acetonitrile with propylene carbonate and ethylene carbonate, as in PATENT LITERATURE 3. However, in PATENT LITERATURE 3, high-temperature durability performance was judged only by evaluation of internal resistance and battery thickness after high-temperature storage, therefore information on whether it practically operates as a battery when it is placed under high-temperature environment has not been disclosed. It is very difficult to suppress reductive decomposition of the electrolyte solution containing an acetonitrile-based solvent, by measures of simple dilution only with ethylene carbonate and propylene carbonate. As a suppression method for reductive decomposition of a solvent, a method for combining a plurality of electrolyte salts and additives is practical, as in PATENT LITERATURE 1 and 2.
(2) Method for Suppressing Reductive Decomposition of Acetonitrile by Using Negative Electrode Active Material Which Occludes Lithium Ions at Higher Potential than Reductive Potential of Acetonitrile.

For example, in PATENT LITERATURE 4, there has been reported that a battery, which avoids reductive decomposition of acetonitrile, can be obtained by using a specific metal compound in a negative electrode. However, in applications putting importance on energy density of the lithium ion secondary battery, a method for using the negative electrode active material which occludes lithium ions at lower potential than reduction potential of acetonitrile is far more advantageous, in view of potential difference. Accordingly, when the improvement ideas of PATENT LITERATURE 4 are used in such applications, they are disadvantageous because of providing a narrow usable voltage range.
(3) Method for Maintaining Stable Liquid State by Dissolving High Concentration of Electrolyte Salt in Acetonitrile.

For example, in PATENT LITERATURE 5, there has been described that reversible reaction between lithium insertion to a graphite electrode and lithium desorption from a graphite electrode is possible, by using an electrolyte solution with 4.2 mol/L of lithium, bis(trifluoromethanesulfonyl)imide ($LiN(SO_2CF_3)_2$) dissolved in acetonitrile. In addition, in PATENT LITERATURE 6, there has been reported that a reaction between $Li^+$ insertion to graphite and $Li^+$ desorption from graphite was observed, and further high-rate discharge was possible, as a result of charge-discharge measurement on a cell using the electrolyte solution with 4.5 mol/L of lithium bis(fluorosulfonyl)imide ($LiN(SO_2F)_2$) dissolved in acetonitrile.

CITATION LIST

Patent Literature

[PATENT LITERATURE 1] WO 2012/057311
[PATENT LITERATURE 2] WO 2013/062056
[PATENT LITERATURE 3] JP4-351860A
[PATENT LITERATURE 4] JP2009-21134A
[PATENT LITERATURE 5] WO 2013/146714
[PATENT LITERATURE 6] JP2014-241198A

SUMMARY OF INVENTION

Technical Problem

However, the lithium ion secondary battery using the electrolyte solution containing acetonitrile is inferior in high-temperature durability performance, as compared with an existing lithium ion secondary battery using the electrolyte solution containing a carbonate solvent, and has not yet attained levels of commercially available products, therefore, has not been feasible.

Reason that the acetonitrile-type lithium ion secondary battery is inferior in high-temperature durability performance is considered as follows from the results of various types of verification experiments.

Under high-temperature environment, a fluorine-containing inorganic lithium salt decomposes while withdrawing hydrogen from methyl group of acetonitrile, and the decomposed product promotes elution of a positive electrode transition metal. Complex cations, where acetonitrile is coordinated to this eluted metal, are chemically stable.

Accordingly, upon repeated charge-discharge under high-temperature environment, the stable complex cations may deposit on an electrode and may possibly cause an increase in internal resistance. In addition, the stable complex cations may also adversely influence on a protective film of a negative electrode, which is suppressing reductive decomposition of acetonitrile. These phenomena proved by disassembly analysis result are newly revealed by the present inventors, which has not been described at all in PATENT LITERATURE 1 to 6.

The present invention has been proposed in view of such circumstances. Accordingly, the purpose of the present invention is to provide a non-aqueous electrolyte solution that contains acetonitrile, having excellent balance between viscosity and dielectric constant, and a fluorine-containing inorganic lithium salt, wherein generation of complex cations comprising a transition metal and acetonitrile can be suppressed, excellent load characteristics can be exhibited, as well as increase in internal resistance upon repeated charge-discharge cycles can be suppressed; and a non-aqueous secondary battery comprising the non-aqueous electrolyte solution.

Solution to Problem

The present inventors have intensively studied to solve the problems. As a result, they have discovered that generation of complex cations comprising a transition metal and acetonitrile can be suppressed, excellent load characteristics can be exhibited, as well as increase in internal resistance upon repeated charge-discharge cycles can be suppressed, in the case where a specific nitrogen-containing cyclic compound is further contained as additives, even in a non-aqueous electrolyte solution containing acetonitrile as a non-aqueous solvent, and thus the present invention has been completed.

Accordingly, the present invention has the following constitutions.

[1] A non-aqueous electrolyte solution comprising:
a non-aqueous solvent containing acetonitrile,
a fluorine-containing inorganic lithium salt, and
a compound represented by the following general formula (1):

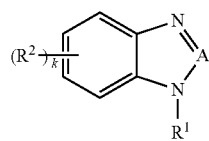

(1)

{wherein A is CH or nitrogen atom,
$R^1$ is hydrogen atom, an alkyl group having 1 to 4 carbon atoms, allyl group, propargyl group, phenyl group, benzyl group, pyridyl group, amino group, pyrrolidylmethyl group, trimethylsilyl group, nitrile group, acetyl group, trifluoroacetyl group, chloromethyl group, methoxymethyl group, isocyanomethyl group, methylsulfonyl group, phenylsulfonyl group, azidosulfonyl group, pyridylsulfonyl group, 2-(trimethylsilyl)ethoxycarbonyloxy group, bis(N,N'-alkyl)aminomethyl group, or bis(N,N'-alkyl)aminoethyl group,
$R^2$ is an alkyl group having 1 to 4 carbon atoms, a fluorine-substituted alkyl group having 1 to 4 carbon atoms, an alkoxy group having 1 to 4 carbon atoms, a fluorine-substituted alkoxy group having 1 to 4 carbon atoms, nitrile group, nitro group, amino group, or a halogen atom, and k is an integer of 0 to 4.}.

[2] The non-aqueous electrolyte solution according to [1], wherein the non-aqueous solvent contains acetonitrile in 20 to 100% by volume.

[3] The non-aqueous electrolyte solution according to [1] or [2], wherein $R^1$ of the compound represented by general formula (1) above is an alkyl group having 1 to 4 carbon atoms, a bis(N,N'-alkyl)aminomethyl group, or a bis(N,N'-alkyl)aminoethyl group.

[4] The non-aqueous electrolyte solution according to any one of [1] to [3], wherein content of the compound represented by general formula (1) above is 0.01 to 10 parts by mass, relative to 100 parts by mass of the non-aqueous electrolyte solution.

[5] The non-aqueous electrolyte solution according to any one of [1] to [4], wherein the fluorine-containing inorganic lithium salt contains $LiPF_6$.

[6] A non-aqueous secondary battery comprising:
a positive electrode having a positive electrode active material layer containing at least one transition metal element selected from Ni, Mn, and Co, on one surface or both surfaces of a current collector;
a negative electrode having a negative electrode active material layer on one surface or both surfaces of another current collector; and
the non-aqueous electrolyte solution according to any one of [1] to [5].

[7] The non-aqueous secondary battery according to [6], wherein the positive electrode active material layer and the negative electrode active material layer face each other, and ratio of the entire area of the surface of the side of the negative electrode active material layer opposing to the positive electrode active material layer, relative to the area of the region where the positive electrode active material layer and the negative electrode active material layer face each other, is larger than 1.0 and below 1.1.

Advantageous Effect of Invention

According to the present invention, the non-aqueous electrolyte solution that contains acetonitrile, having excellent balance between viscosity and the dielectric constant, and the fluorine-containing inorganic lithium salt, wherein generation of complex cations comprising a transition metal and acetonitrile can be suppressed, excellent load characteristics can be exhibited, and increase in internal resistance upon repeated charge-discharge cycles is suppressed, and is superior in cycling performance; and the non-aqueous secondary battery comprising the non-aqueous electrolyte solution can be provided.

DESCRIPTION OF EMBODIMENTS

Explanation will be given in detail below on embodiments for carrying out the present invention (hereafter it is referred to simply as "the present embodiment"). Numerical value range described using "-- to --" in the present description should include numerical values before and after "to".

The non-aqueous electrolyte solution of the present embodiment (hereafter it is also referred to simply as "the electrolyte solution") comprises:

the non-aqueous solvent containing acetonitrile, the fluorine-containing inorganic lithium salt, and the compound represented by the following general formula (1):

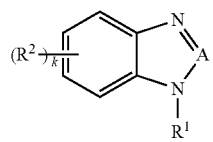

(1)

{wherein A is CH or nitrogen atom, $R^1$ is hydrogen atom, an alkyl group having 1 to 4 carbon atoms, allyl group, propargyl group, phenyl group, benzyl group, pyridyl group, amino group, pyrrolidylmethyl group, trimethylsilyl group, nitrile group, acetyl group, trifluoroacetyl group, chloromethyl group, methoxymethyl group, isocyanomethyl group, methylsulfonyl group, phenylsulfonyl group, azidosulfonyl group, pyridylsulfonyl group, 2-(trimethylsilyl)ethoxycarbonyloxy group, bis(N,N'-alkyl)aminomethyl group, or bis(N,N'-alkyl)aminoethyl group, $R^2$ is an alkyl group having 1 to 4 carbon atoms, a fluorine-substituted alkyl group having 1 to 4 carbon atoms, an alkoxy group having 1 to 4 carbon atoms, a fluorine-substituted alkoxy group having 1 to 4 carbon atoms, nitrile group, nitro group, amino group, or a halogen atom, and k is an integer of 0 to 4.}.

<1. Total Configuration of Non-Aqueous Secondary Battery>

The electrolyte solution of the present embodiment can be used, for example, in a non-aqueous secondary battery. The non-aqueous secondary battery of the present embodiment includes, for example, a lithium ion secondary battery comprising:

a positive electrode containing a positive electrode material which is capable of occluding and releasing lithium ions, as a positive electrode active material, and a negative electrode containing at least one negative electrode material selected from a group consisting of a material which is capable of occluding and releasing lithium ions, and a metal lithium, as a negative electrode active material.

Figure 1:
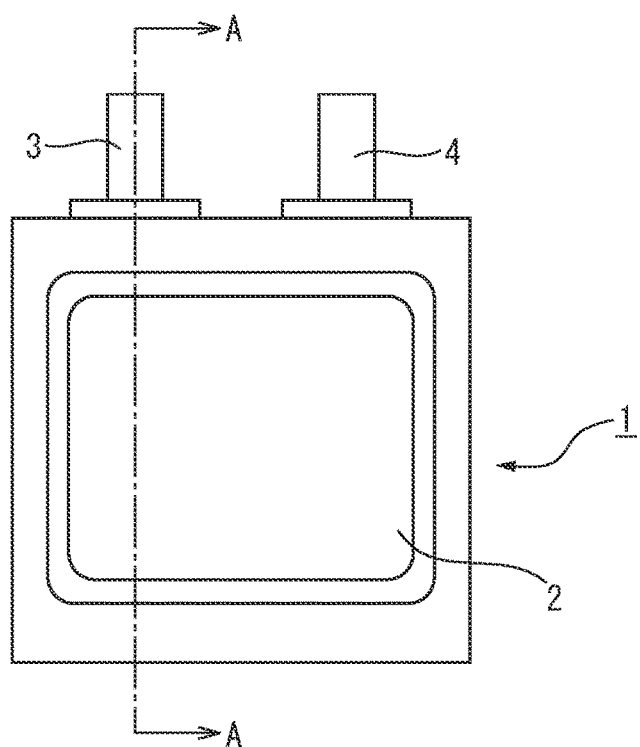
FIG. 1 is a plan view schematically showing one example of the non-aqueous secondary battery in the present embodiment.
Figure 2:
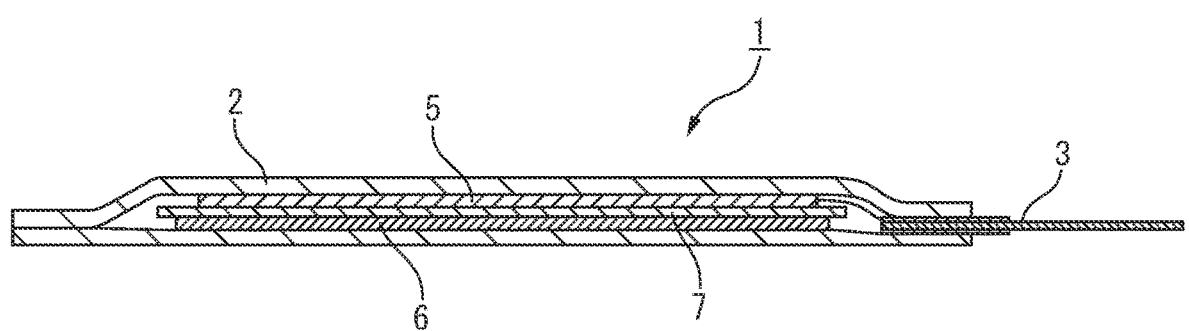
FIG. 2 is a cross-sectional view along the A-A line of the non-aqueous secondary battery of FIG. 1.

The non-aqueous secondary battery of the present embodiment may be specifically the non-aqueous secondary battery shown in FIG. 1 and FIG. 2. FIG. 1 is a plan view schematically showing the non-aqueous secondary battery, and FIG. 2 is a cross-sectional view along the A-A line of FIG. 1.

The non-aqueous secondary battery 1 accommodates a laminated electrode structure in which the positive electrode 5 and negative electrode 6 are laminated via a separator 7, and the non-aqueous electrolyte solution (not shown), within a battery outer package 2 composed of two sheets of aluminum laminated films. The battery outer package 2 is sealed by heat sealing upper and lower aluminum laminated films at the outer peripheral part thereof. The laminated structure, where the positive electrode 5, the separator and the negative electrode 6 are laminated in this order, is impregnated with the non-aqueous electrolyte solution. However, in FIG. 2, each layer composing the battery outer package 2, along with each layer of the positive electrode 5 and negative electrode 6 are not shown in distinction, to avoid a complicated drawing.

The aluminum laminated film composing the battery outer package 2 is preferably a film coated with a polyolefin-based resin on both surfaces of a sheet of aluminum foil.

The positive electrode 5 is connected with the positive electrode external terminal 3 via a lead structure inside the battery 1. The negative electrode 6 is also connected with the negative electrode external terminal 4 via the lead structure inside the battery 1, although not shown. The positive electrode external terminal 3 and the negative electrode external terminal 4 are each pulled out of the battery outer package 2 at one terminal side, so as to be connectable with an external device, etc., and an ionomer part thereof is heat sealed together with one side of the battery outer package 2.

The non-aqueous secondary battery 1 shown in FIGS. 1 and 2 has the laminated electrode structure in which the positive electrode 5 and negative electrode 6 are each one sheet. However, lamination number of the positive electrode 5 and negative electrode 6 may be increased as appropriate depending on capacity designing. In the case of the laminated electrode structure having a plurality of the positive electrode 5 and a plurality of the negative electrode 6, both tabs at the same electrode may be joined together by welding etc., and then may be joined to one lead structure by welding, etc. and may be pulled out of a battery. As the tabs at the same electrode, an aspect composed of an exposed part of the current collector, or an aspect composed of a metal piece welded at the exposed part of the current collector, etc., is possible.

The positive electrode 5 is composed of the positive electrode active material layer prepared from a positive-electrode mixture, and the positive electrode current collector. The negative electrode 6 is composed of the negative electrode active material layer prepared from a negative-electrode mixture, and the negative electrode current collector. The positive electrode 5 and negative electrode 6 are arranged so that the positive electrode active material layer and the negative electrode active material layer face each other via the separator 7.

Hereafter there may be the cases where the positive electrode and the negative electrode are collectively abbreviated as "the electrode", the positive electrode active material layer and the negative electrode active material layer as "the electrode active material layer", the positive electrode mixture and the negative electrode mixture as "the electrode mixture".

As for each member of these, a material equipped in a conventional lithium ion secondary battery may be used, as long as it satisfies each requirement in the present embodiment, and may be, for example, a material described later. Explanation will be given in detail below on each member of the non-aqueous secondary battery.

<2. Electrolyte Solution>

The electrolyte solution of the present embodiment contains the non-aqueous solvent (hereafter it may also be simply referred to as "the solvent"), the fluorine-containing inorganic lithium salt, and the compound represented by general formula (1) above (the nitrogen-containing cyclic compound). The fluorine-containing inorganic lithium salt is not sufficient in heat stability, as well as has a property of easily generating lithium fluoride and hydrogen fluoride by hydrolysis caused by trace amount of moisture in the solvent, although it is superior in ion conductivity. Decomposition of the fluorine-containing inorganic lithium salt decreases ion conductivity of the electrolyte solution containing the fluorine-containing inorganic lithium salt, as well as may cause fatally adverse influence on a battery, such as corrosion of a material of the electrode, the current collector, etc., or decomposition of the solvent, by the lithium fluoride and hydrogen fluoride generated.

It is preferable that the electrolyte solution in the present embodiment does not contain moisture; however, it may contain negligibly trace amount of moisture within a range in which it does not inhibit the present invention from solving the problem. Such a content of moisture is preferably 0 to 100 ppm, relative to the total amount of the electrolyte solution.

<2-1. Non-Aqueous Solvent>

Acetonitrile has high ion conductivity and is capable of increasing diffusibility of lithium ions inside a battery. Accordingly, when the electrolyte solution contains acetonitrile, and in particular, even at the positive electrode where loading amount of the positive electrode active material is increased by thickening the positive electrode active material layer, lithium ions can be diffused well as far as a region near the current collector, where lithium ions are difficult to reach in discharge under high load. Accordingly, sufficient capacity can be brought out even in discharge under high load, and such a non-aqueous secondary battery superior in load characteristics is attainable.

Because ion conductivity of the non-aqueous electrolyte solution is enhanced, as described above, by using acetonitrile in the non-aqueous solvent of the non-aqueous electrolyte solution, rapid charge characteristics of the non-aqueous secondary battery can also be enhanced. In constant current (CC)-constant voltage (CV) charging of the non-aqueous secondary battery, capacity per unit time in CC charging period is larger than charge capacity per unit time in CV charging period. In the case of using acetonitrile as the non-aqueous solvent of the non-aqueous electrolyte solution, a region capable of CC charging can be larger (CC charging time can be longer), as well as charge current can also be higher, resulting in significant reduction in time from charging start to attainment of a full charged state of the non-aqueous secondary battery.

The non-aqueous solvent is not especially limited, as long as it contains acetonitrile, and other non-aqueous solvent may be contained or may not be contained.

"The non-aqueous solvent" referred to in the present embodiment means a component excluding the lithium salt and the nitrogen-containing cyclic compound from the electrolyte solution, when a solvent, the lithium salt and the nitrogen-containing cyclic compound, together with electrode protection additives, described later, are contained in the electrolyte solution, the solvent together with the electrode protection additives are referred to collectively as "the non-aqueous solvent". The lithium salt and the nitrogen-containing cyclic compound, described later, are not implied in the non-aqueous solvent.

The other non-aqueous solvents include alcohols, for example, methanol, ethanol, etc.; an aprotic solvent, etc., and among them, the aprotic solvent is preferable.

Among the other non-aqueous solvents, a specific example of the aprotic solvent includes, for example, a cyclic carbonate represented by ethylene carbonate, propylene carbonate, 1,2-butylene carbonate, trans-2,3-butylene carbonate, cis-2,3-butylene carbonate, 1,2-pentylene carbonate, trans-2,3-pentylene carbonate, cis-2,3-pentylene carbonate, and vinylene carbonate; a cyclic fluorinated carbonate represented by fluoroethylene carbonate, 1,2-difluoroethylene carbonate, and trifluoromethylethylene carbonate; a lactone represented by γ-butyrolactone, γ-valerolactone, γ-caprolactone, δ-valerolactone, δ-caprolactone, and ε-caprolactone; a sulfur compound represented by sulfolane, dimethylsulfoxide, and ethylene glycol sulfite; a cyclic ether represented by tetrahydrofuran, 2-methyltetrahydrofuran, 1,4-dioxane, and 1,3-dioxane; a linear carbonate represented by ethyl methyl carbonate, dimethyl carbonate, diethyl carbonate, methyl propyl carbonate, methyl isopropyl carbonate, dipropyl carbonate, methyl butyl carbonate, dibutyl carbonate, ethyl propyl carbonate, and methyl trifluoroethyl carbonate; a linear fluorinated carbonate represented by trifluorodimethyl carbonate, trifluorodiethyl carbonate, and trifluoroethyl methyl carbonate;

a mononitrile represented by propionitrile, butyronitrile, valeronitrile, benzonitrile, and acrylonitrile; an alkoxy group-substituted nitrile represented by methoxyacetonitrile and 3-methoxypropionitrile; a dinitrile represented by malononitrile, succinonitrile, glutaronitrile, adiponitrile, 1,4-dicyanoheptane, 1,5-dicyanopentane, 1,6-dicyanohexane, 1,7-dicyanoheptane, 2,6-dicyanoheptane, 1,8-dicyanooctane, 2,7-dicyanooctane, 1,9-dicyanononane, 2,8-dicyanononane, 1,10-dicyanodecane, 1,6-dicyanodecane, and 2,4-dimethylglutaronitrile; a cyclic nitrile represented by benzonitrile; a linear ester represented by methyl propionate; a linear ether represented by dimethoxyethane, diethyl ether, 1,3-dioxolane, diglyme, triglyme, and tetraglyme; a fluorinated ether represented by $Rf^4$—$OR^5$ (wherein $Rf^4$ is an alkyl group containing fluorine, $R^5$ is an organic group which may contain fluorine.); ketones represented by acetone, methyl ethyl ketone, and methyl isobutyl ketone, and as well as, halides represented by fluorinated compounds thereof. These may be used as one type alone, or as two or more types in combination.

Among these other non-aqueous solvents, it is preferable that one or more types of the cyclic carbonate and the linear carbonate may be used together with acetonitrile. Here, only one type of those exemplified ones may be selected and used, as the cyclic carbonate and the linear carbonate, or two or more types (for example, two or more types of the exemplified cyclic carbonates, two or more types of the exemplified linear carbonates, or two or more types composed of one or more types of the exemplified cyclic carbonates and one or more types of the exemplified linear carbonates) may be used. Among them, ethylene carbonate, propylene carbonate, vinylene carbonate, or fluoroethylene carbonate is more preferable as the cyclic carbonate, and ethyl methyl carbonate, dimethyl carbonate, or diethyl carbonate is more preferable as the linear carbonate. In addition, it is further preferable to use the cyclic carbonate.

Acetonitrile tends to reductively and electrochemically decompose. Therefore, it is preferable to carry out at least one of mixing acetonitrile with other solvent, and adding the electrode protection additives for protective coating film formation to acetonitrile.

It is preferable that the non-aqueous solvent contains one or more types of cyclic aprotic polar solvents, and more preferably contains one or more types of cyclic carbonates, in order to increase ionization degree of the lithium salt, which contributes to charge-discharge of the non-aqueous secondary battery.

Content of acetonitrile is 20 to 100% by volume, and 30% by volume or more is preferable, and 40% by volume or more is further preferable, relative to total amount of the non-aqueous solvent. It is preferable that this value is 85% by volume or less, and further preferable 66% by volume or less. When content of acetonitrile is 20% by volume or more, relative to total amount of the non-aqueous solvent, there is tendency that ion conductivity increases and high rate characteristics can be exerted, and still more dissolution of lithium salts can be promoted. When content of acetonitrile in the non-aqueous solvent is within the above range, because the nitrogen-containing cyclic compound suppresses increase in internal resistance of a battery, there is tendency that high-temperature cycle characteristics and other electrical characteristics can be further improved, while maintaining superior performance of acetonitrile.

<2-2. Lithium Salt>

The lithium salt in the present embodiment is characterized by containing the fluorine-containing inorganic lithium salt. "The fluorine-containing inorganic lithium salt" means such a lithium salt that does not contain carbon atom in the anion, but contains fluorine atom in the anion, and is soluble to acetonitrile. "The inorganic lithium salt" means such a lithium salt that does not contain carbon atom in the anion, and is soluble to acetonitrile. "The organic lithium salt" means such a lithium salt that that contains carbon atom in the anion, and is soluble to acetonitrile.

The fluorine-containing inorganic lithium salt in the present embodiment forms a passive film on the surface of a metal foil, which is the positive electrode current collector, and suppresses corrosion of the positive electrode current collector. This fluorine-containing inorganic lithium salt is superior also in view of solubility, conductivity and ionization degree. Therefore, it is essentially necessary for the fluorine-containing inorganic lithium salt added as the lithium salt. A specific example of the fluorine-containing inorganic lithium salt includes, for example, $LiPF_6$, $LiBF_4$, $LiAsF_6$, $Li_2SiF_6$, $LiSbF_6$, $Li_2B_{12}F_bH_{12-b}$ (wherein b is an integer of 0 to 3, and preferably an integer of 1 to 3), $LiN(SO_2F)_2$, etc.

These fluorine-containing inorganic lithium salts may be used alone as one type, or as two or more types in combination. As the fluorine-containing inorganic lithium salt, compounds, which are double salts of LiF and Lewis acid, are desirable, and among them, use of the fluorine-containing inorganic lithium salt having phosphorus atom is more preferable, because free fluorine atom tends to be released more easily, and $LiPF_6$ is particularly preferable. Use of the fluorine-containing inorganic lithium salt having boron atom, as the fluorine-containing inorganic lithium salt, is preferable, because excess free acid components, which could incur battery deterioration, tends to be captured more easily, and $LiBF_4$ is particularly preferable from such a view point.

Content of the fluorine-containing inorganic lithium salt in the electrolyte solution of the present embodiment is not especially limited. However, this value is preferably 0.2 mol or more, more preferably 0.5 mol or more, and further preferably 0.8 mol or more, relative to 1 L of the non-aqueous solvent. This value is preferably 15 mol or less, more preferably 4 mol or less, and further preferably 2.8 mol or less, relative to 1 L of the non-aqueous solvent. When content of the fluorine-containing inorganic lithium salt is within the above range, there is tendency that ion conductivity increases and high rate characteristics can be exerted, and high-temperature cycle characteristics and other battery characteristics can be further improved, while maintaining superior performance of acetonitrile.

As the lithium salt in the present embodiment, lithium salt which is generally used in the non-aqueous secondary battery may be secondarily added, other than the fluorine-containing inorganic lithium salt. A specific example of the other lithium salt includes, for example, an inorganic lithium salt in which fluorine is not contained as an anion, such as $LiClO_4$, $LiAlO_4$, $LiAlCl_4$, $LiB_{10}Cl_{10}$, Li chloroborane, etc.; an organic lithium salt, such as $LiCF_3SO_3$, $LiCF_3CO_2$, $Li_2C_2F_4(SO_3)_2$, $LiC(CF_3SO_2)_3$, $LiC_nF_{2n+1}SO_3$ (n≥2), a Li lower aliphatic carboxylate, Li tetraphenylborate, etc.; an organic lithium salt represented by $LiN(SO_2C_mF_{2m+1})_2$ [wherein m is an integer of 1 to 8], such as $LiN(SO_2CF_3)_2$, $LiN(SO_2C_2F_5)_2$, etc.; an organic lithium salt represented by $LiPF_n(C_pF_{2p+1})_{6-n}$ [wherein n is an integer of 1 to 5, and p is an integer of 1 to 8], such as $LiPF_5(CF_3)$, etc.; an organic lithium salt represented by $LiBF_q(C_sF_{2s+1})_{4-q}$ [wherein q is an integer of 1 to 3, and s is an integer of 1 to 8], such as $LiBF_3(CF_3)$, etc.; lithium bis(oxalato) borate (LiBOB) represented by $LiB(C_2O_4)_2$; a halogenated LiBOB; lithium oxalato difluoroborate (LiODFB) represented by $LiBF_2(C_2O_4)$; lithium bis(malonate) borate (LiBMB) represented by $LiB(C_3O_4H_2)_2$; an organic lithium salt, such as lithium tetrafluoro oxalato phosphate represented by $LiPF_4(C_2O_4)$, lithium difluoro bis(oxalato) phosphate represented by $LiPF_2(C_2O_4)_2$, etc.; a lithium salt bonded with a polyvalent anion; organic lithium salts each represented by the following general formulae (2a), (2b), and (2c)

$$LiC(SO_2R^6)(SO_2R^7)(SO_2R^8) \quad (2a)$$

$$LiN(SO_2OR^9)(SO_2OR^{10}) \quad (2b)$$

$$LiN(SO_2R^{11})(SO_2OR^{12}) \quad (2c)$$

{wherein $R^6$, $R^7$, $R^8$, $R^9$, $R^{10}$, $R^{11}$, and $R^{12}$ may each be the same or different, and represent a perfluoroalkyl group having 1 to 8 carbon atoms.}, and one type, or two or more types among them may be used together with the fluorine-containing inorganic lithium salt.

It is preferable to add secondarily an organic lithium salt having oxalate group to the electrolyte solution, so as to improve load characteristics and charge-discharge cycle characteristics of the non-aqueous secondary battery, and it is particularly preferable to add one or more types selected from a group consisting of $LiB(C_2O_4)_2$, $LiBF_2(C_2O_4)$, $LiPF_4(C_2O_4)$, and $LiPF_2(C_2O_4)_2$. This organic lithium salt having oxalate group may be contained in a negative electrode (the negative electrode active material layer), other than added to the non-aqueous electrolyte solution.

Addition amount of the organic lithium salt having oxalate group to the non-aqueous electrolyte solution is preferably 0.005 mole or more, more preferably 0.02 mole or more, and further preferably 0.05 mole or more, as amount per 1 L of the non-aqueous solvent of the non-aqueous electrolyte solution, in view of ensuring effect of use thereof in a better state. However, excessively more amount of the organic lithium salt having the oxalate group in the non-aqueous electrolyte solution could cause deposition. Accordingly, addition amount of the organic lithium salt having the oxalate group to the non-aqueous electrolyte solution is preferably less than 1.0 mole, more preferably less than 0.5 mole, and further preferably less than 0.2 mole, as amount per 1 L of the non-aqueous solvent of the non-aqueous electrolyte solution.

<2-3. Electrode Protection Additives>

In the electrolyte solution in the present embodiment, additives for protecting an electrode may be contained other than the nitrogen-containing cyclic compound.

The electrode protection additives are not especially limited, as long as not inhibiting the solution to problem by the present invention. The additives may be substantially duplicated with a substance carrying a role as a solvent for dissolving the lithium salt (i.e., the non-aqueous solvent). It is preferable that the electrode protection additives are substances contributing to performance enhancement of the electrolyte solution and the non-aqueous secondary battery in the present embodiment; however, such a substance may be encompassed that does not participate directly to an electrochemical reaction.

Specific examples of the electrode protective additives include, for example, a fluoroethylene carbonate represented by 4-fluoro-1,3-dioxolane-2-one, 4,4-difluoro-1,3-dioxolane-2-one, cis-4,5-difluoro-1,3-dioxolane-2-one, trans-4,5-difluoro-1,3-dioxolane-2-one, 4,4,5-trifluoro-1,3-dioxolane-2-one, 4,4,5,5-tetrafluoro-1,3-dioxolane-2-one, and 4,4,5-trifluoro-5-methyl-1,3-dioxolane-2-one; an unsaturated bond-containing cyclic carbonate represented by vinylene carbonate, 4,5-dimethylvinylene carbonate, and vinylethylene carbonate; a lactone represented by γ-butyrolactone, γ-valerolactone, γ-caprolactone, δ-valerolactone, δ-caprolactone, and ε-caprolactone; a cyclic ether represented by 1,4-dioxane; a cyclic sulfur compound represented by ethylene sulfite, propylene sulfite, butylene sulfite, pentene sulfite, sulfolane, 3-methyl sulfolane, 1,3-propane sultone, 1,4-butane sultone, and tetramethylene sulfoxide. These may be used as one type alone, or as two or more types in combination.

Acetonitrile, which is one component of the non-aqueous solvent, tends to be reductively and electrochemically decomposed, therefore, it is preferable that the non-aqueous solvent containing the acetonitrile contains one or more types of cyclic aprotic polar solvents, as additives for protection film formation to the negative electrode, and more preferable to contain one or more types of unsaturated bond-containing cyclic carbonates.

Content of the electrode protection additives in the electrolyte solution in the present embodiment is not especially limited. However, content of the electrode protection additives is preferably 0.1 to 30% by volume, more preferably 2 to 20% by volume, and further preferably 5 to 15% by volume, relative to the total amount of the non-aqueous solvent.

In the present embodiment, the higher content of the electrode protection additives is, the more deterioration of the electrolyte solution can be suppressed. However, the lower content of the electrode protection additives enhances high rate characteristics the more under low-temperature environment of the non-aqueous secondary battery. Therefore, by adjusting content of the electrode protection additives within the above range, there is tendency that superior performance based on high ion conductivity of the electrolyte solution can be exerted at the maximum, without impairing fundamental function as the non-aqueous secondary battery. By preparing the electrolyte solution in such a composition, there is tendency that a further good state of all of cycling performance, high rate performance under low-temperature environment, and other battery characteristics of the non-aqueous secondary battery can be attained.

<2-4. Nitrogen-Containing Cyclic Compound>

The electrolyte solution in the present embodiment is characterized by containing the nitrogen-containing cyclic compound represented by following general formula (1), as the additives:

(1)

{wherein A is CH or nitrogen atom, $R^1$ is hydrogen atom, an alkyl group having 1 to 4 carbon atoms, allyl group, propargyl group, phenyl group, benzyl group, pyridyl group, amino group, pyrrolidylmethyl group, trimethylsilyl group, nitrile group, acetyl group, trifluoroacetyl group, chloromethyl group, methoxymethyl group, isocyanomethyl group, methylsulfonyl group, phenylsulfonyl group, azidosulfonyl group, pyridylsulfonyl group, 2-(trimethylsilyl)ethoxycarbonyloxy group, bis(N,N'-alkyl)aminomethyl group, or bis(N,N'-alkyl)aminoethyl group, $R^2$ is an alkyl group having 1 to 4 carbon atoms, a fluorine-substituted alkyl group having 1 to 4 carbon atoms, an alkoxy group having 1 to 4 carbon atoms, a fluorine-substituted alkoxy group having 1 to 4 carbon atoms, nitrile group, nitro group, amino group, or a halogen atom, and k is an integer of 0 to 4.}.

Specific examples of the nitrogen-containing cyclic compound in the present embodiment will be exemplified below. They may be used as one type alone or as two or more types in combination.

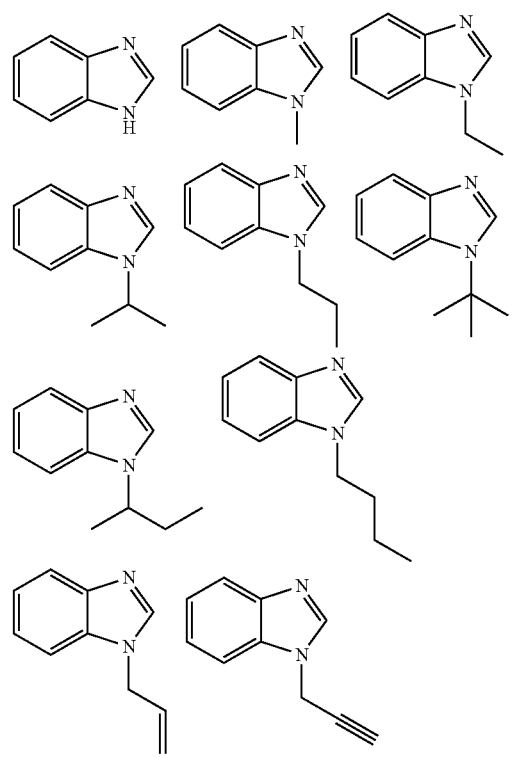

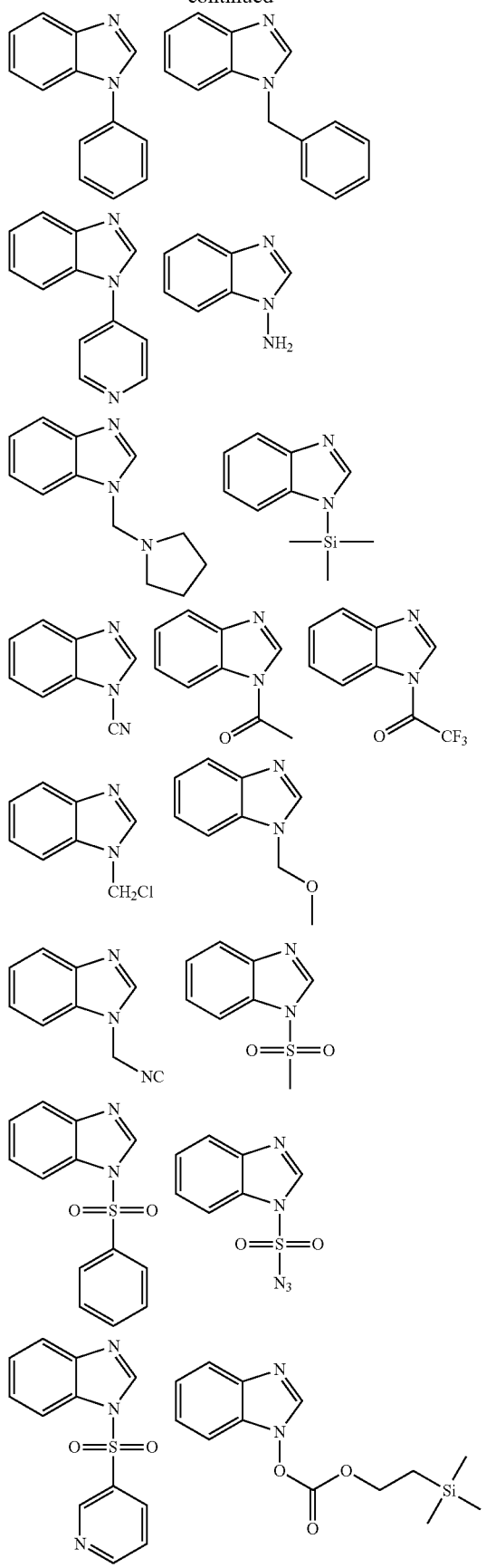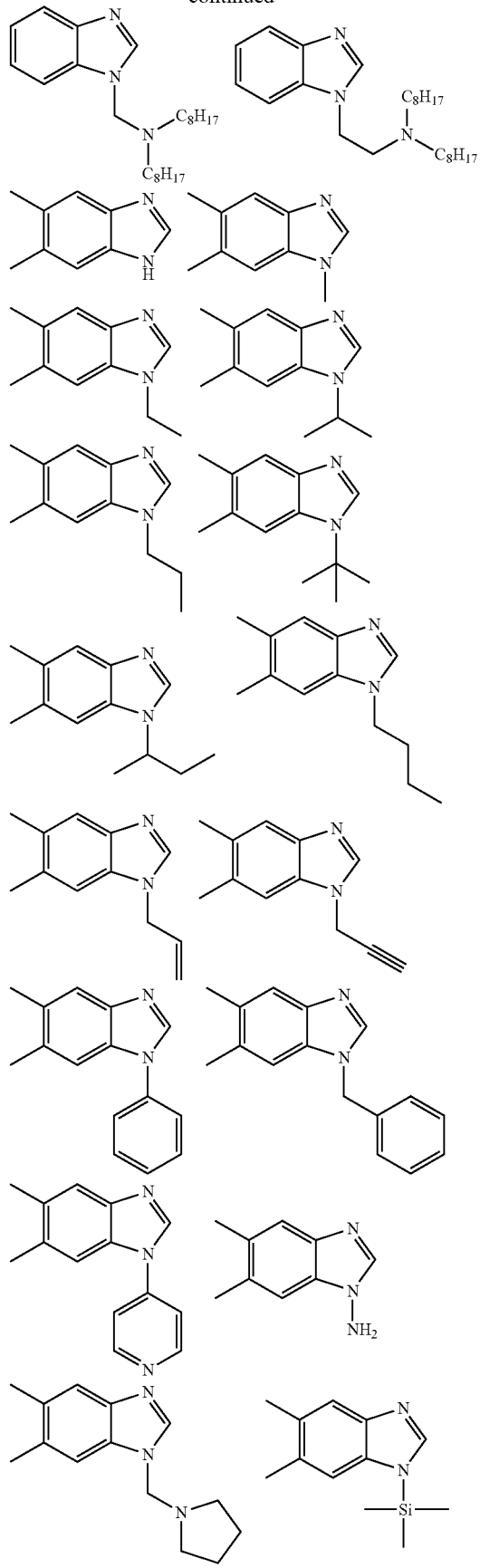

-continued
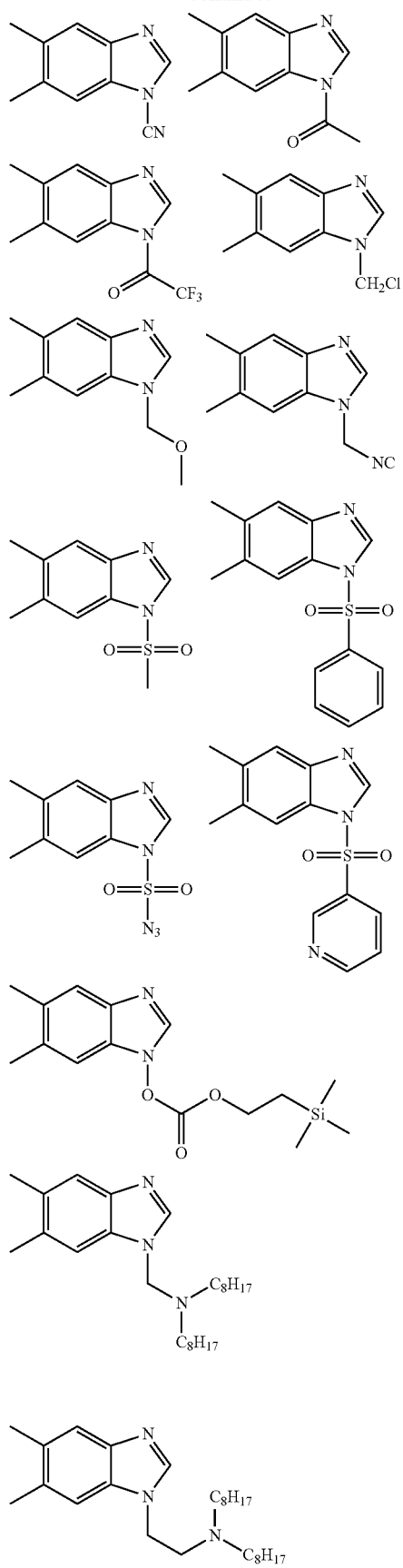
-continued
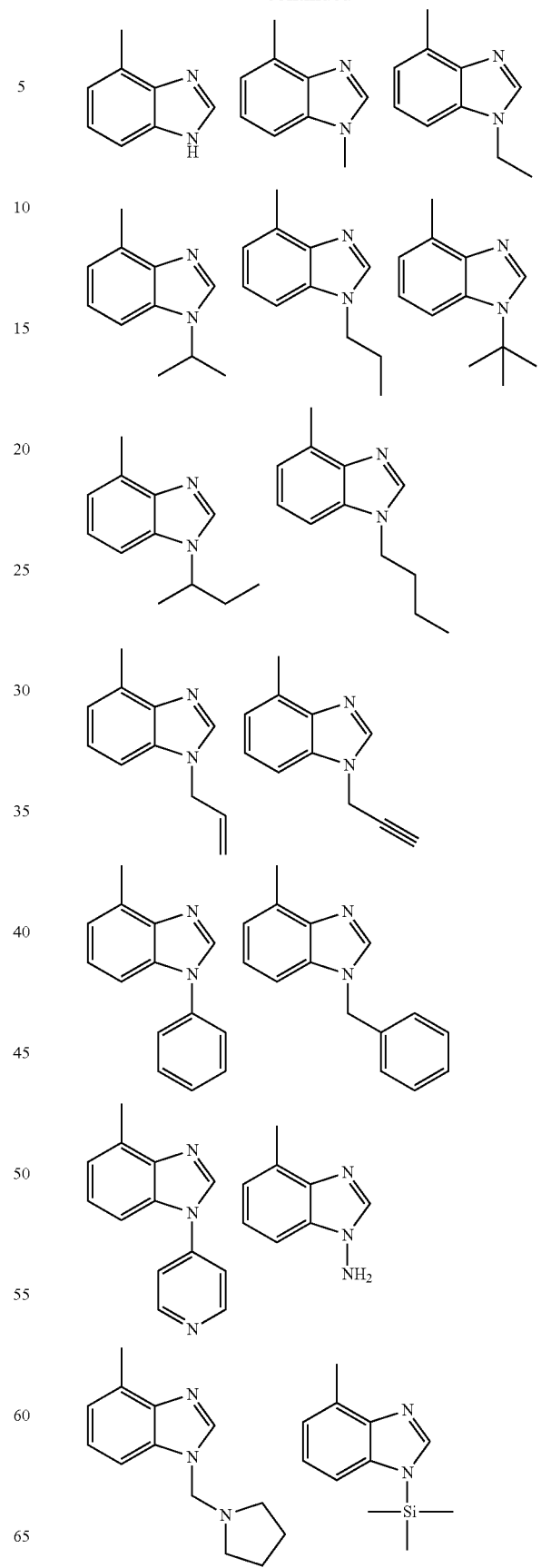

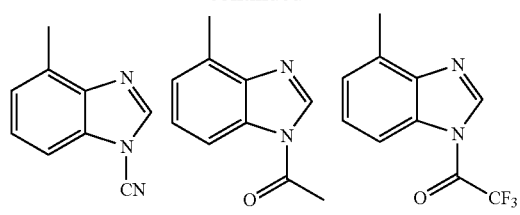
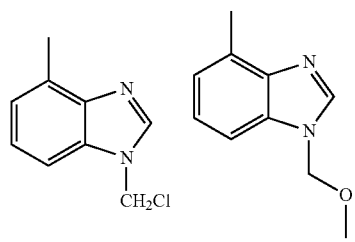
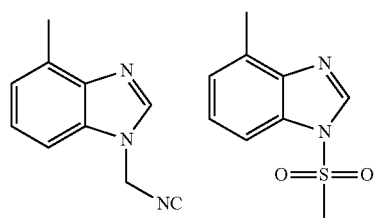
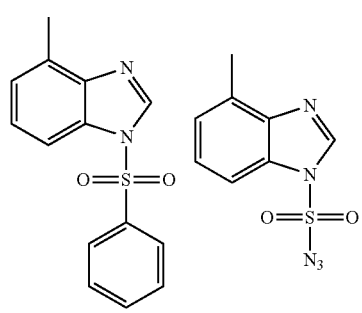
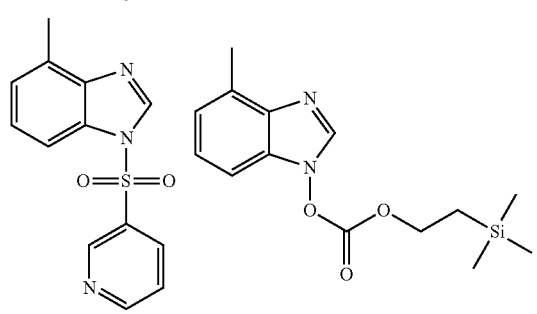
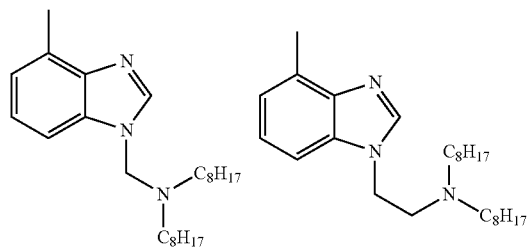
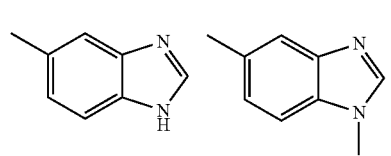
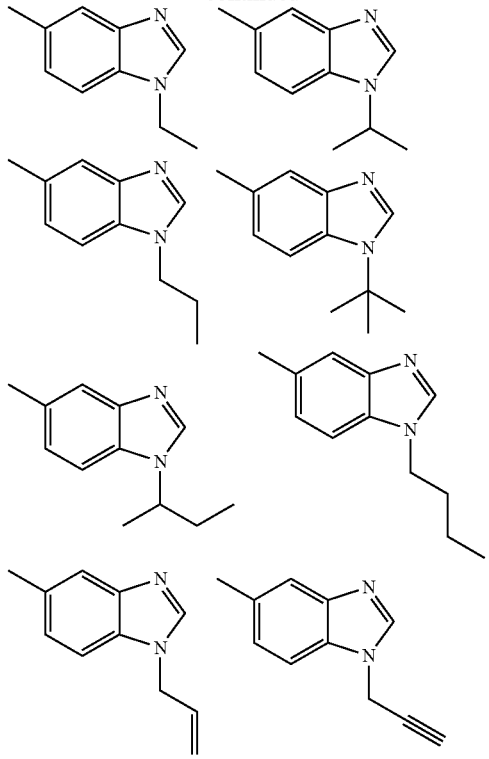
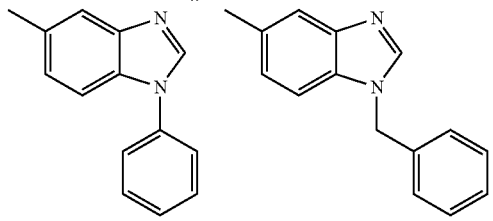
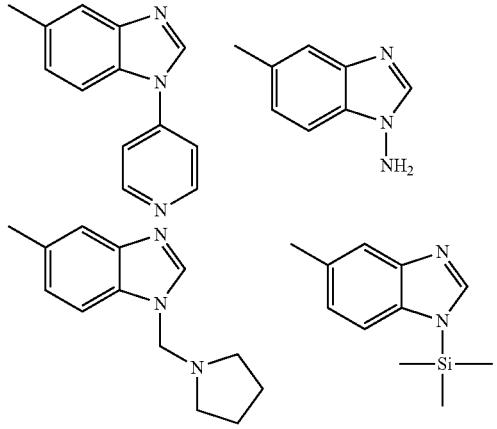
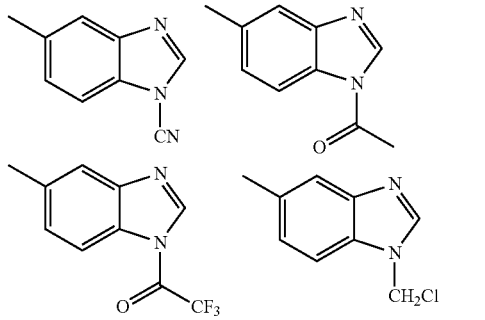

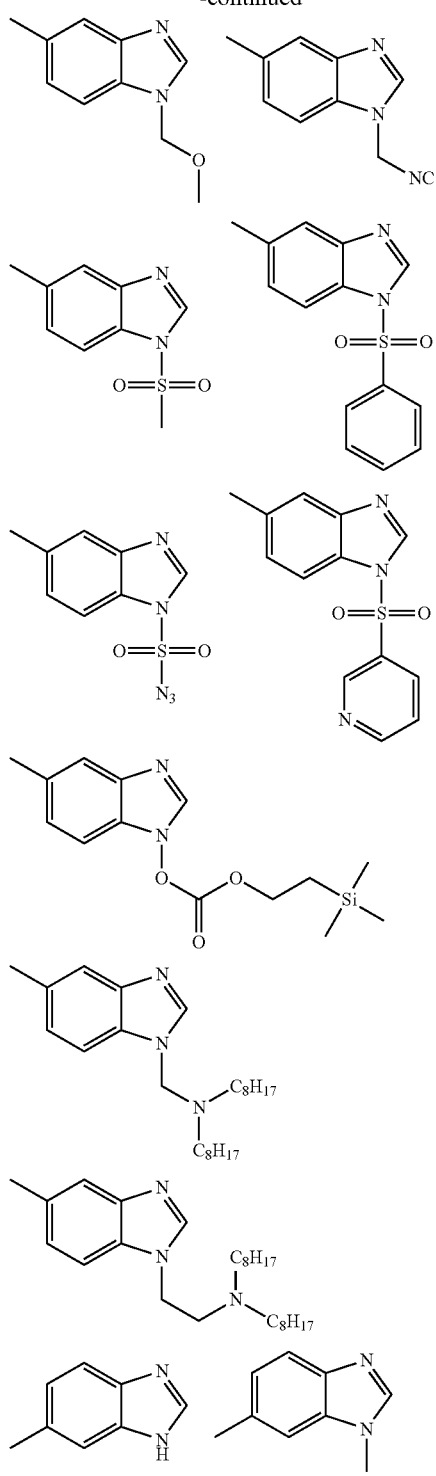
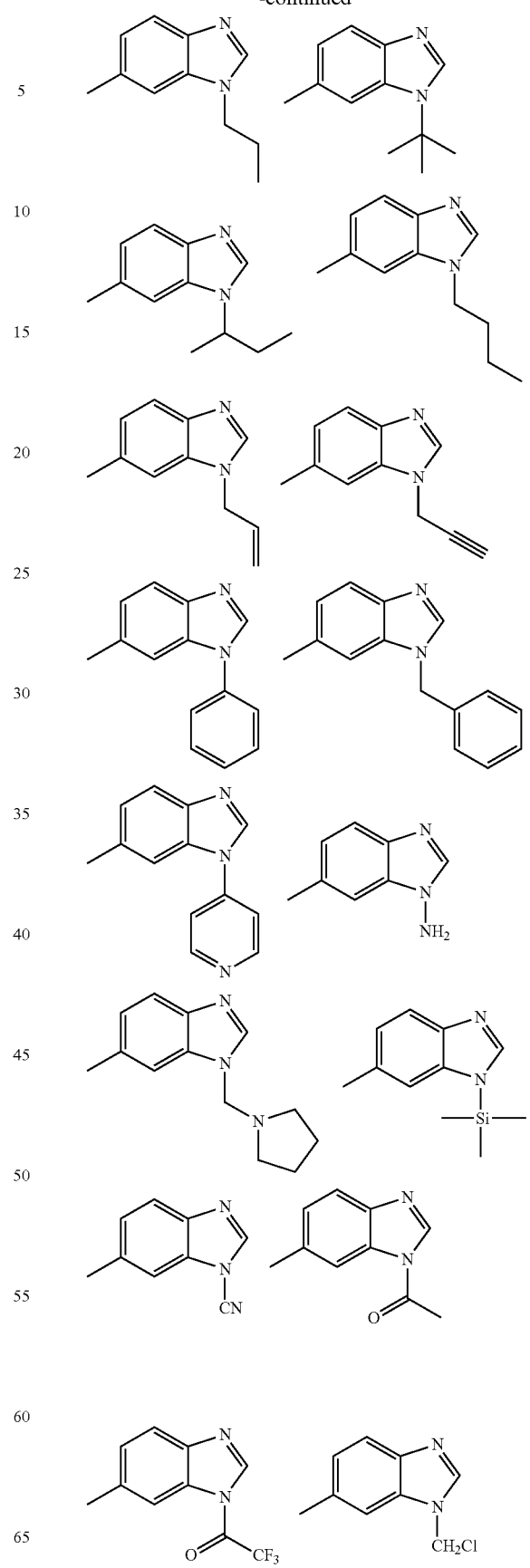

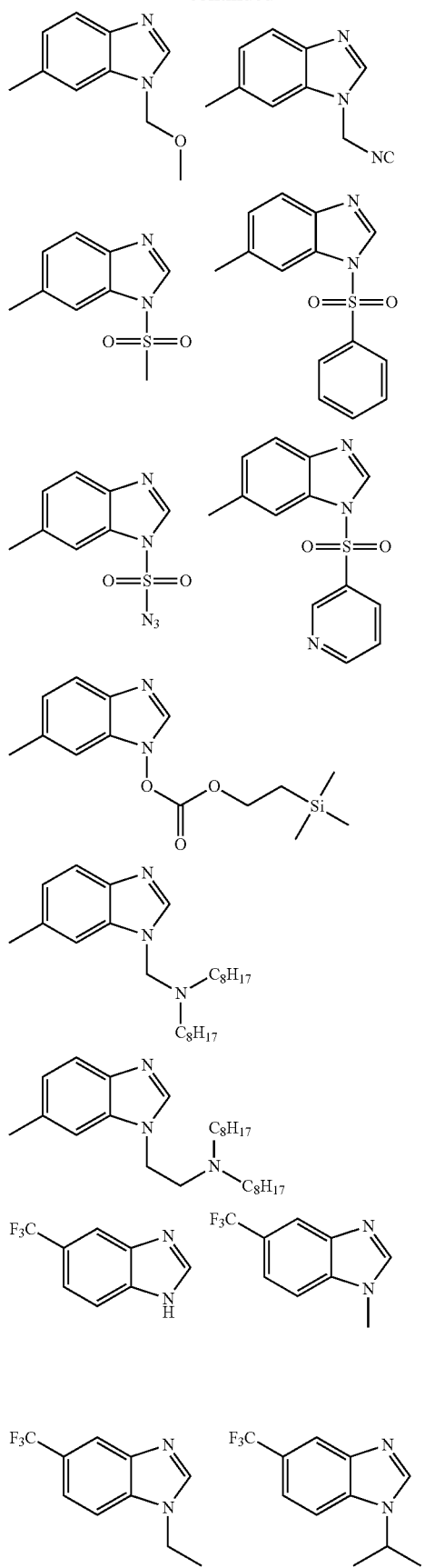
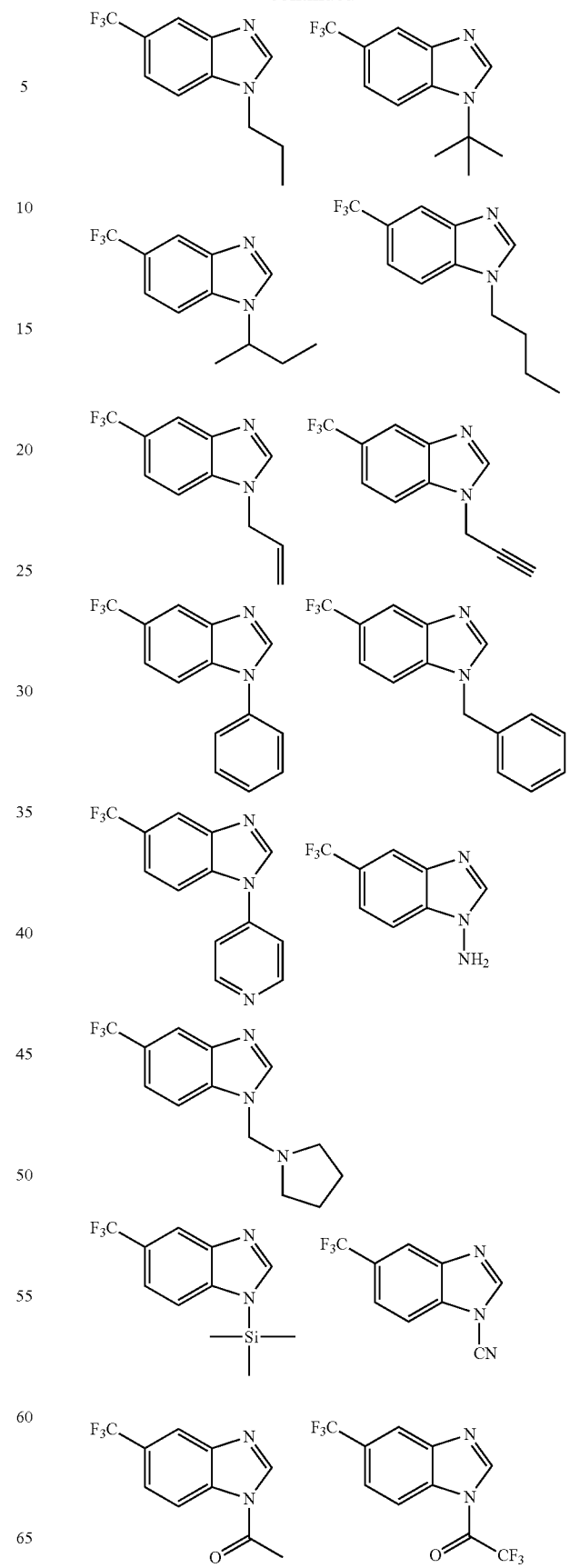

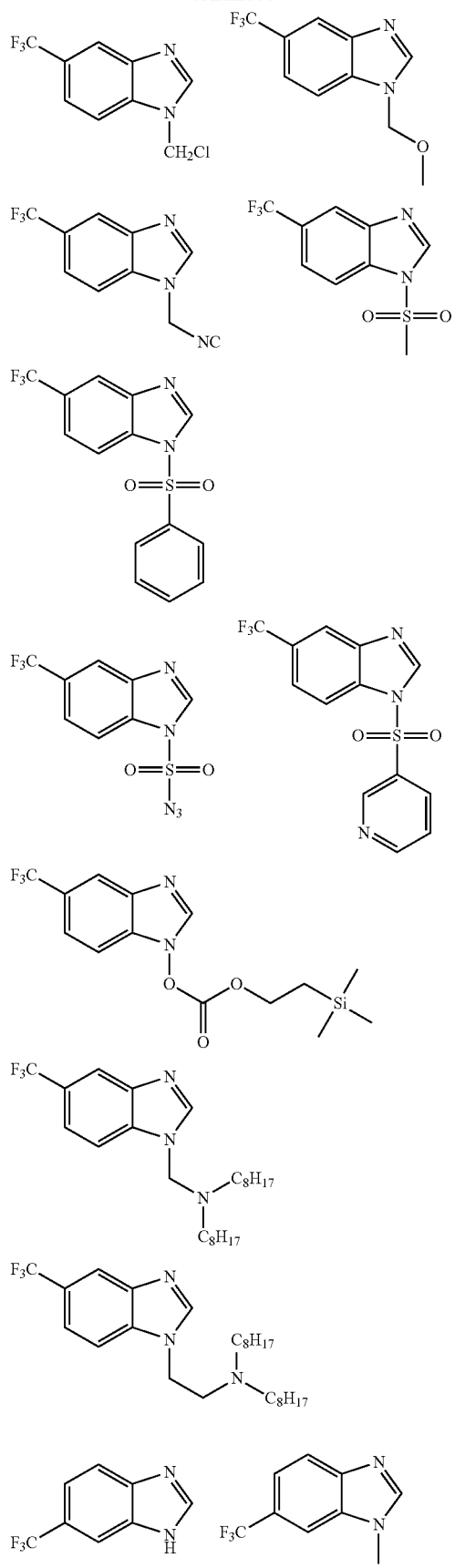

-continued
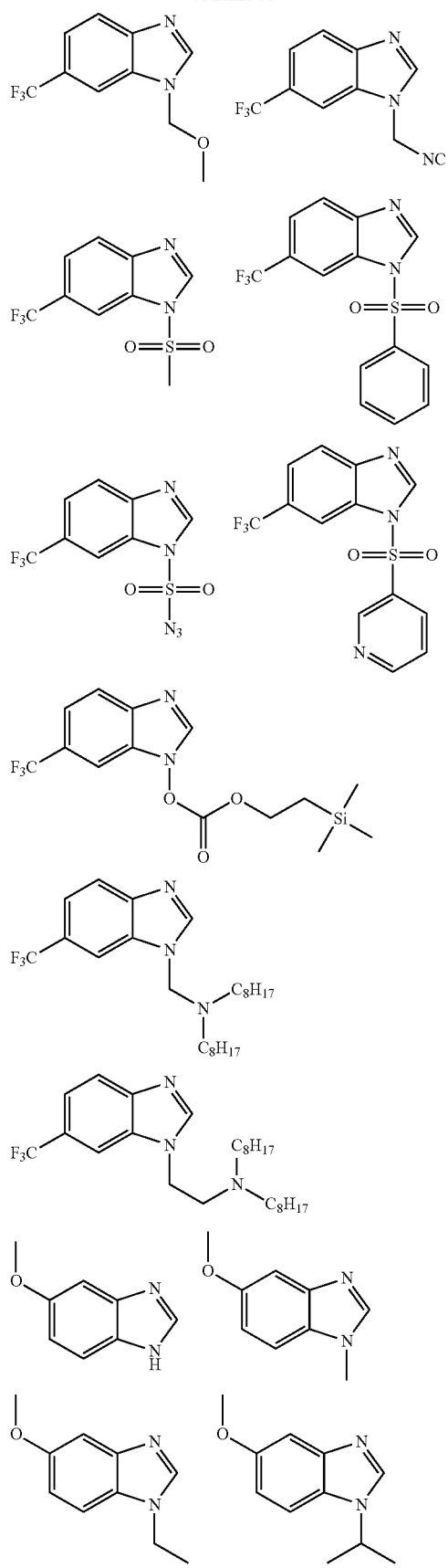
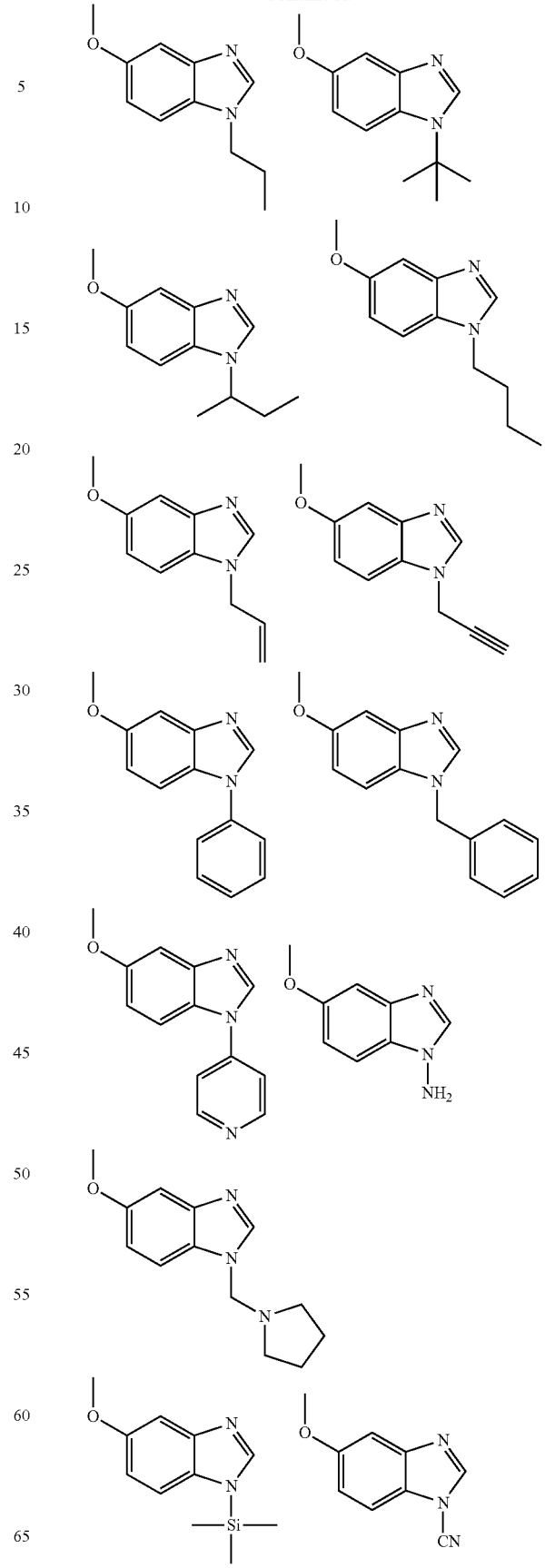

-continued
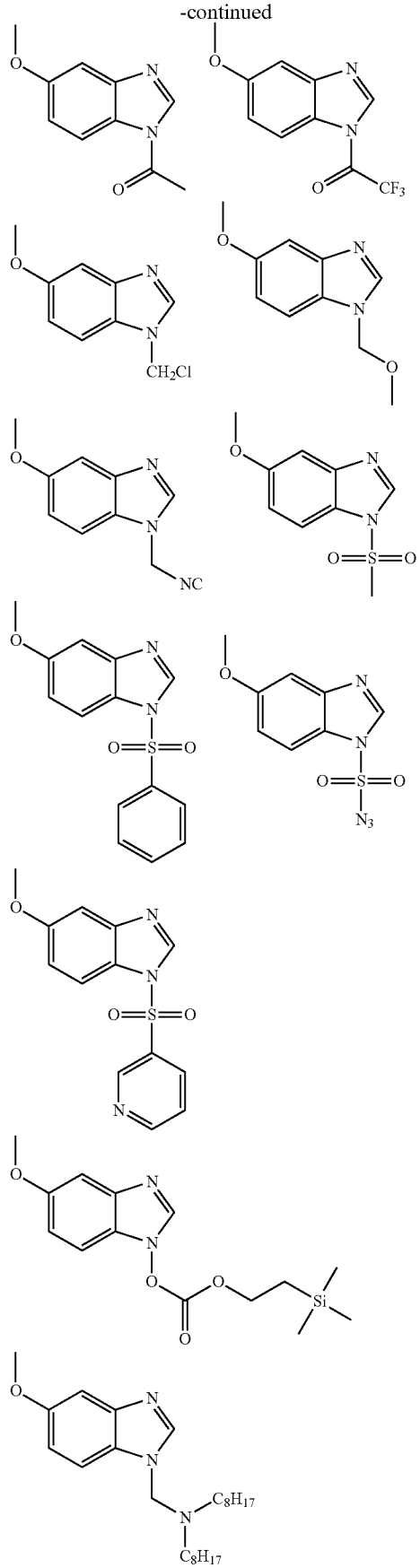
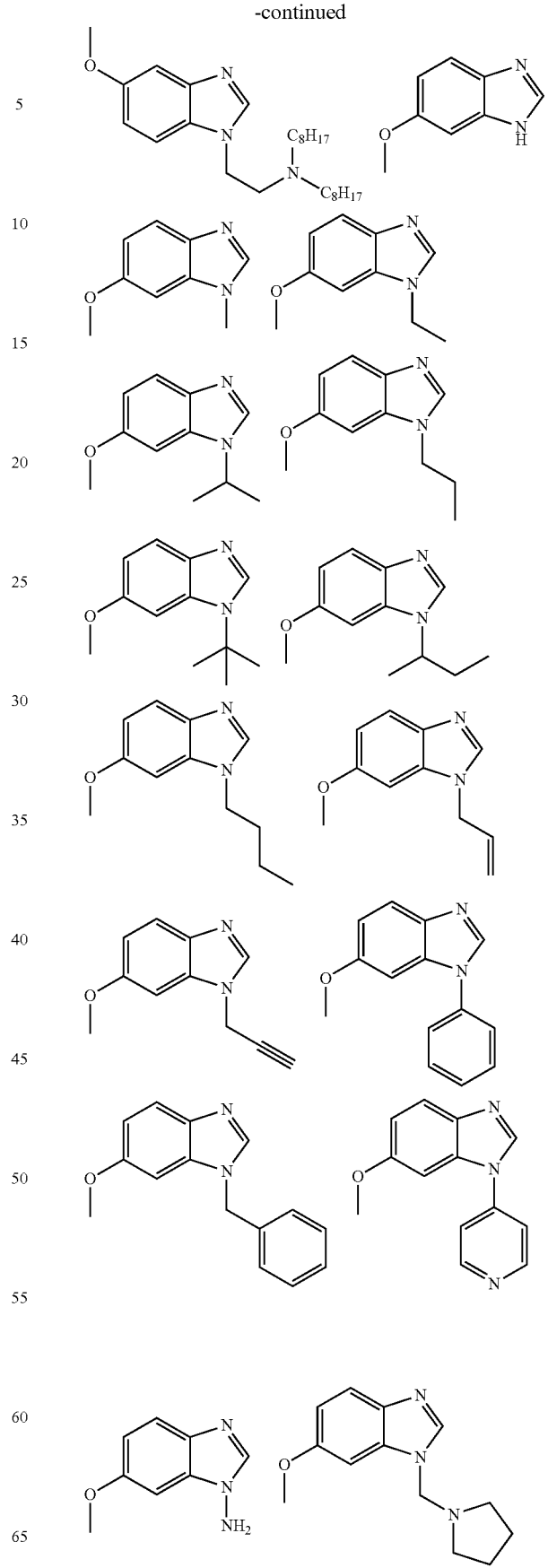

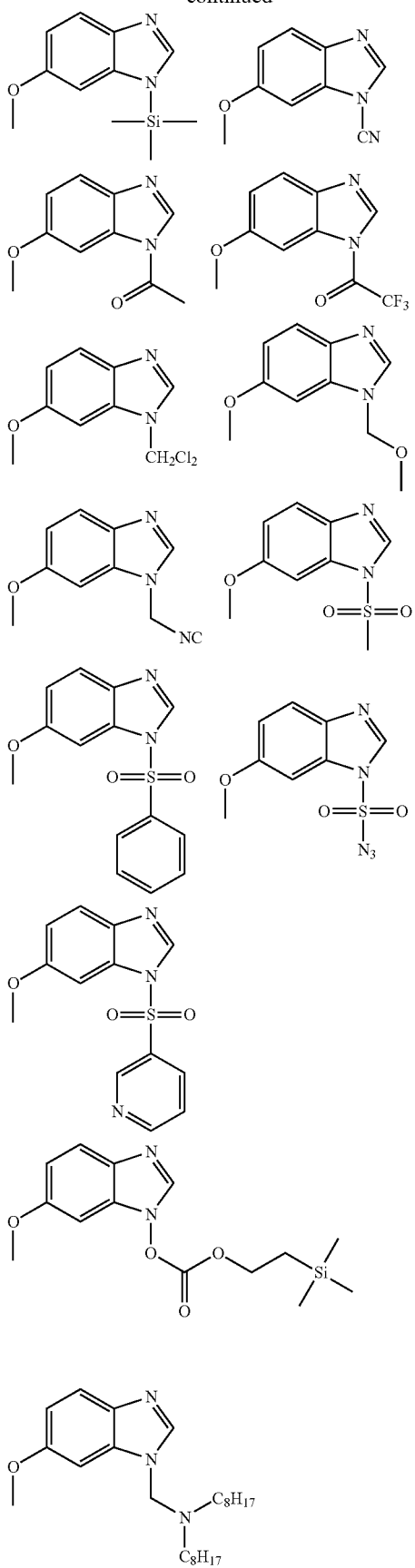

-continued
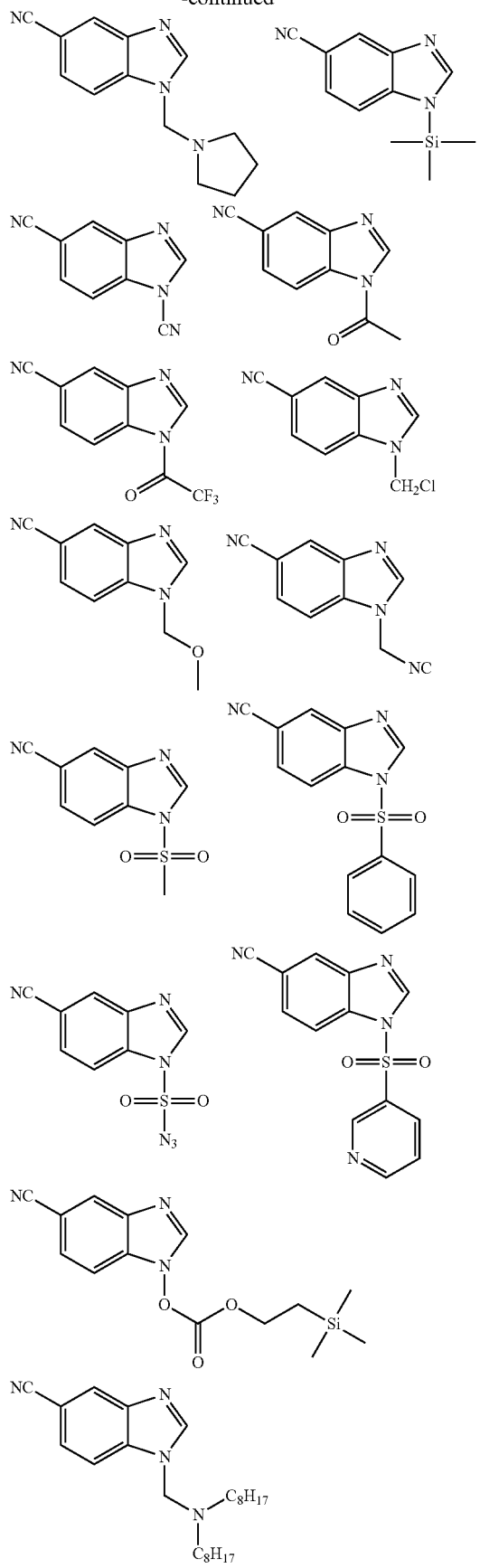
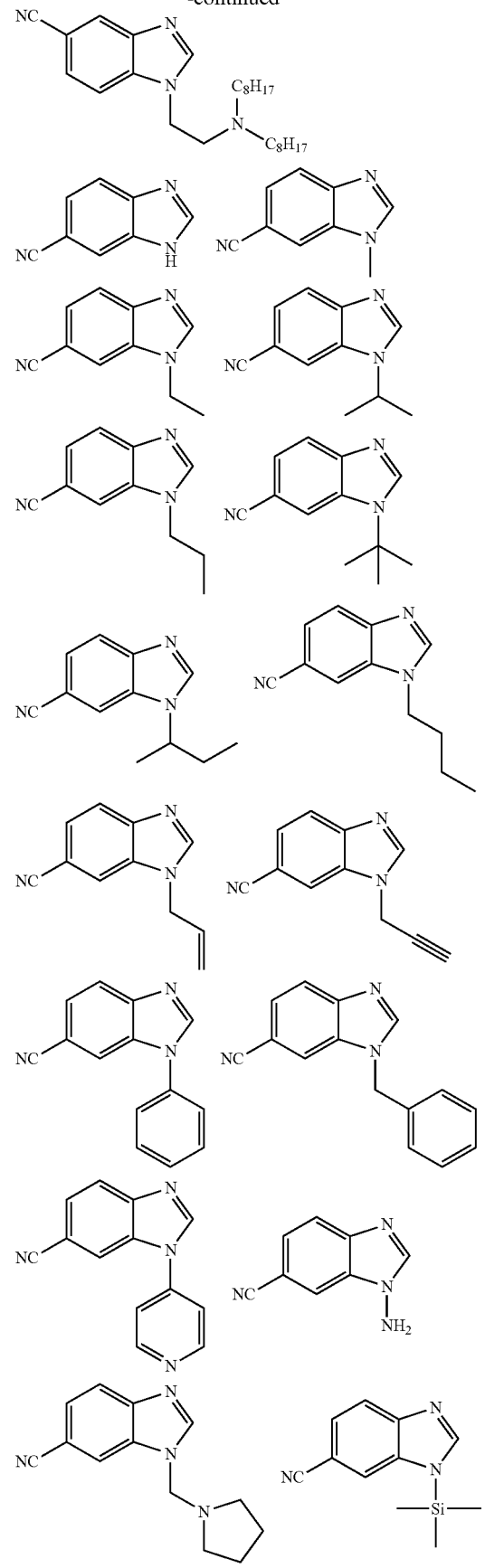

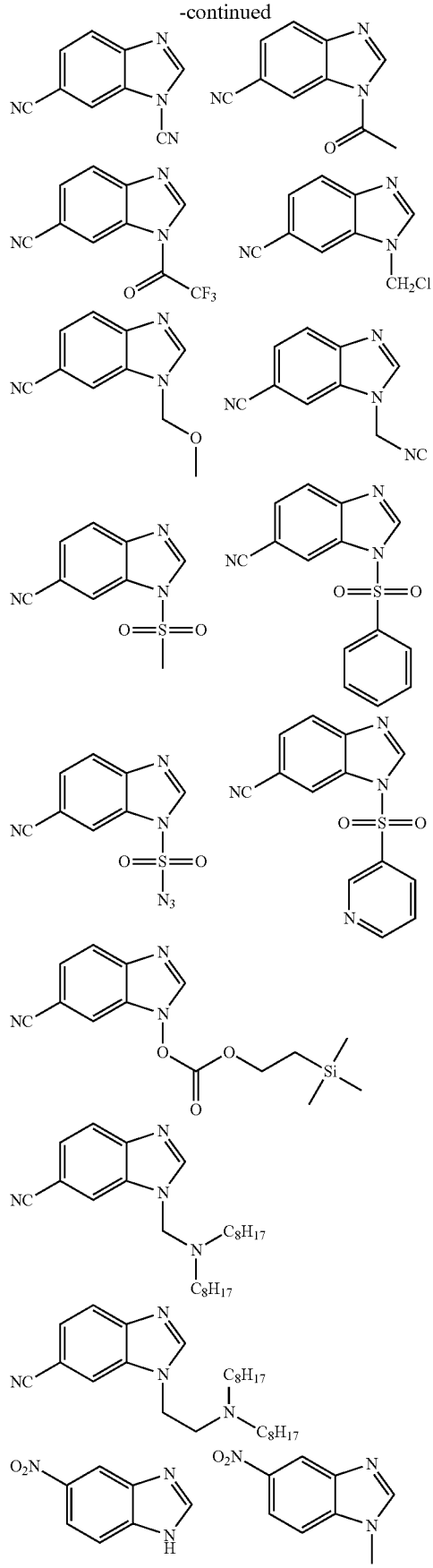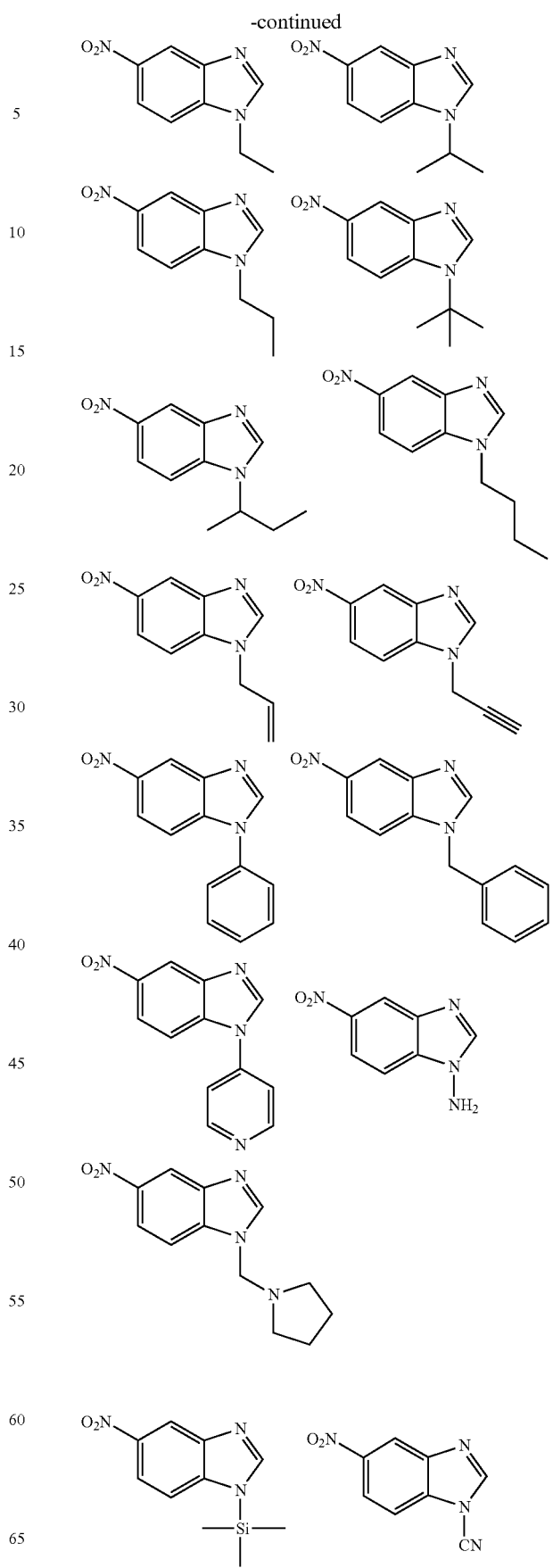

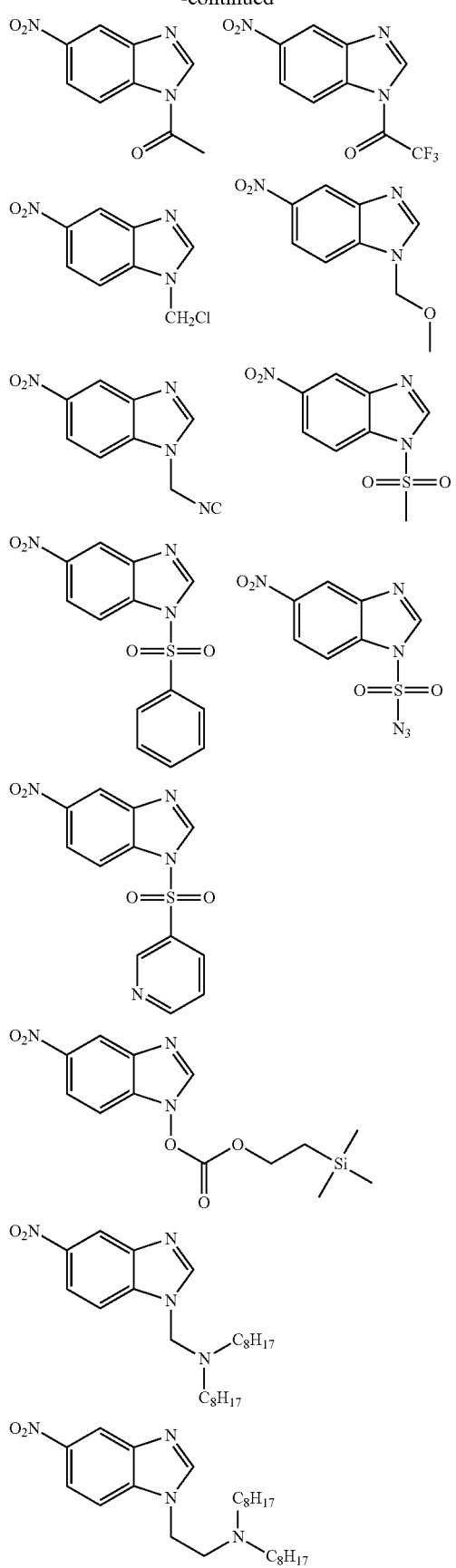
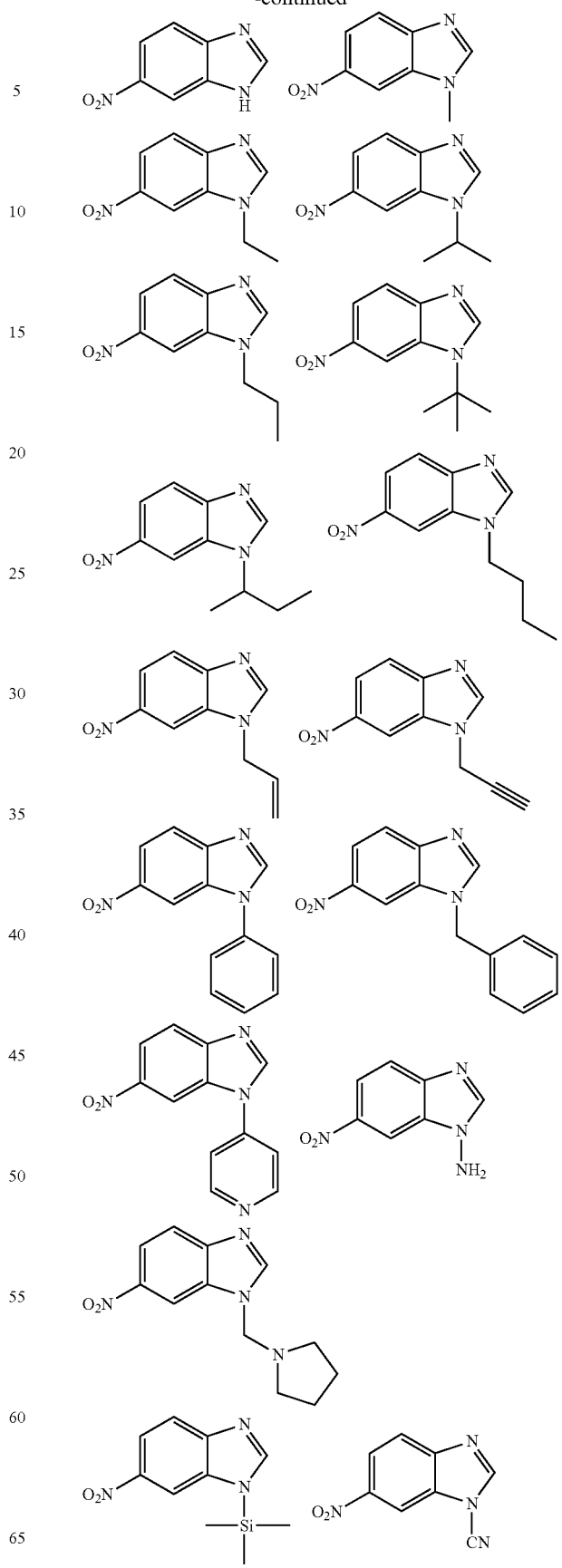

-continued
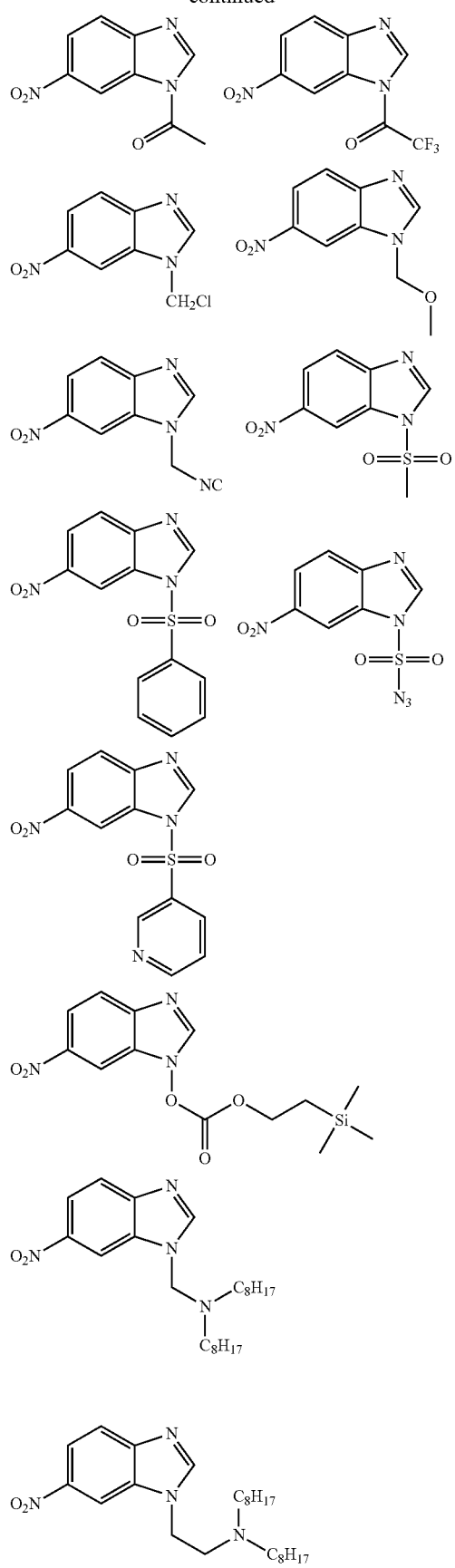
-continued
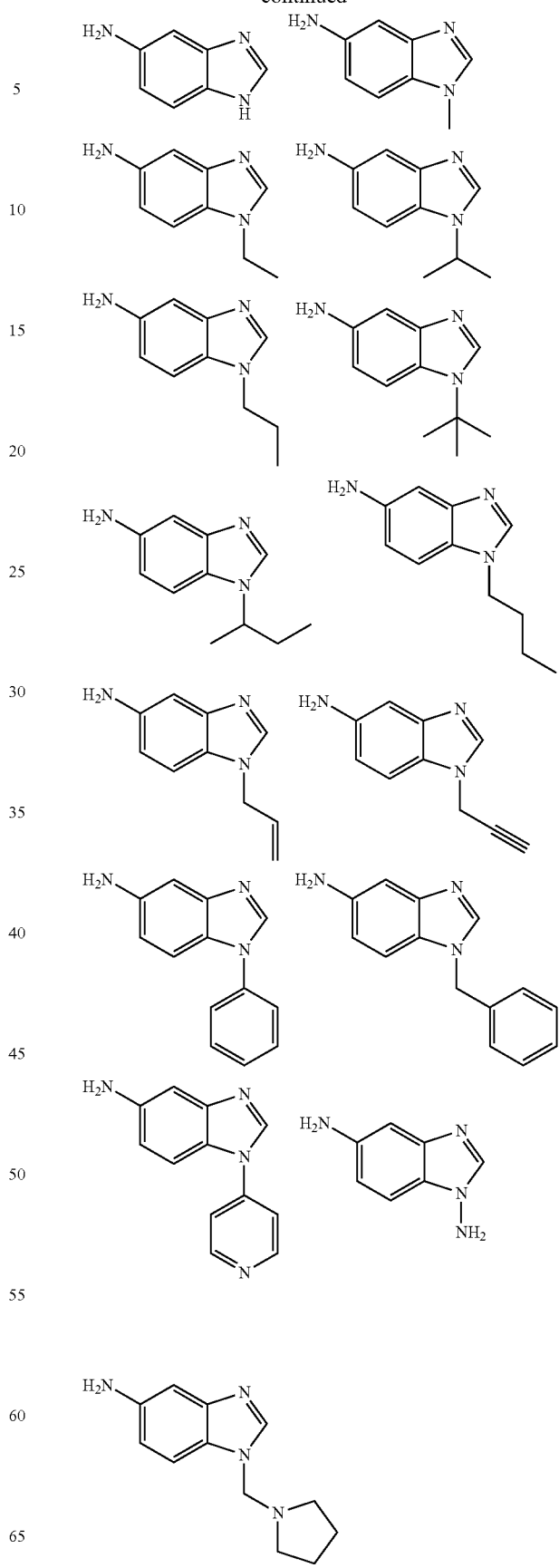

-continued
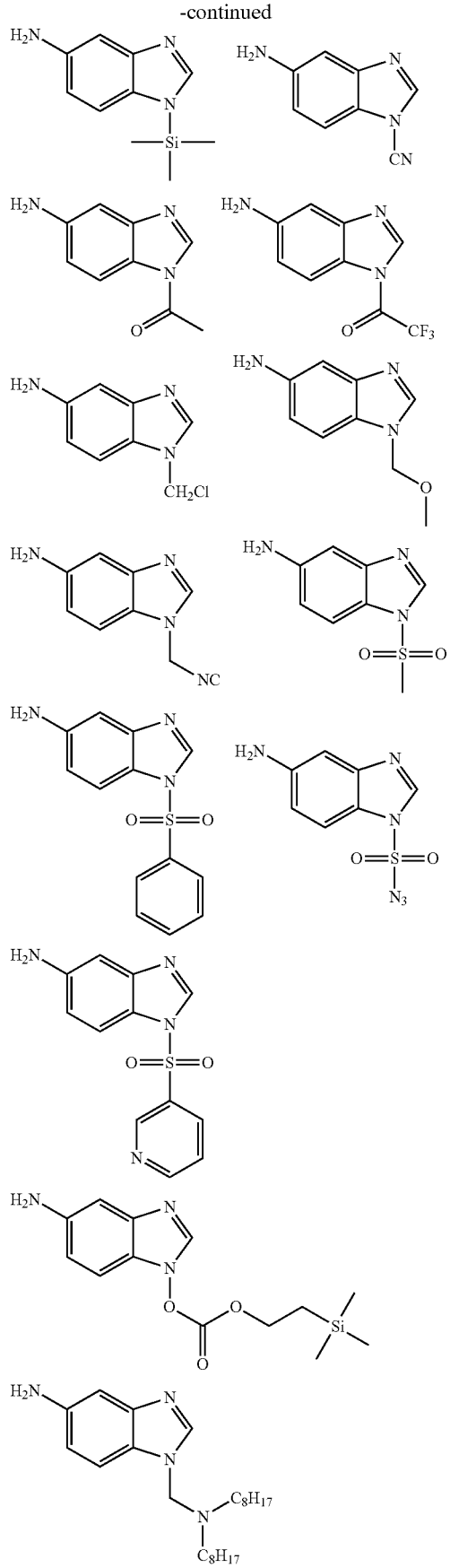
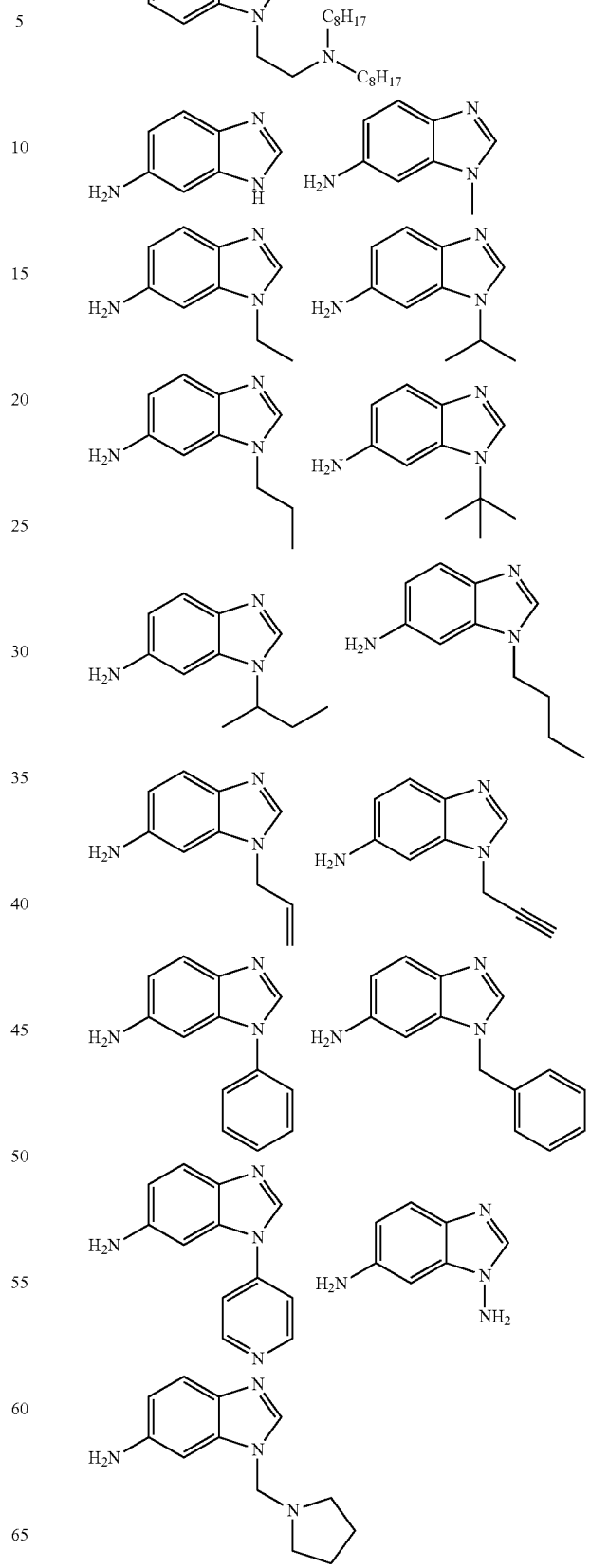

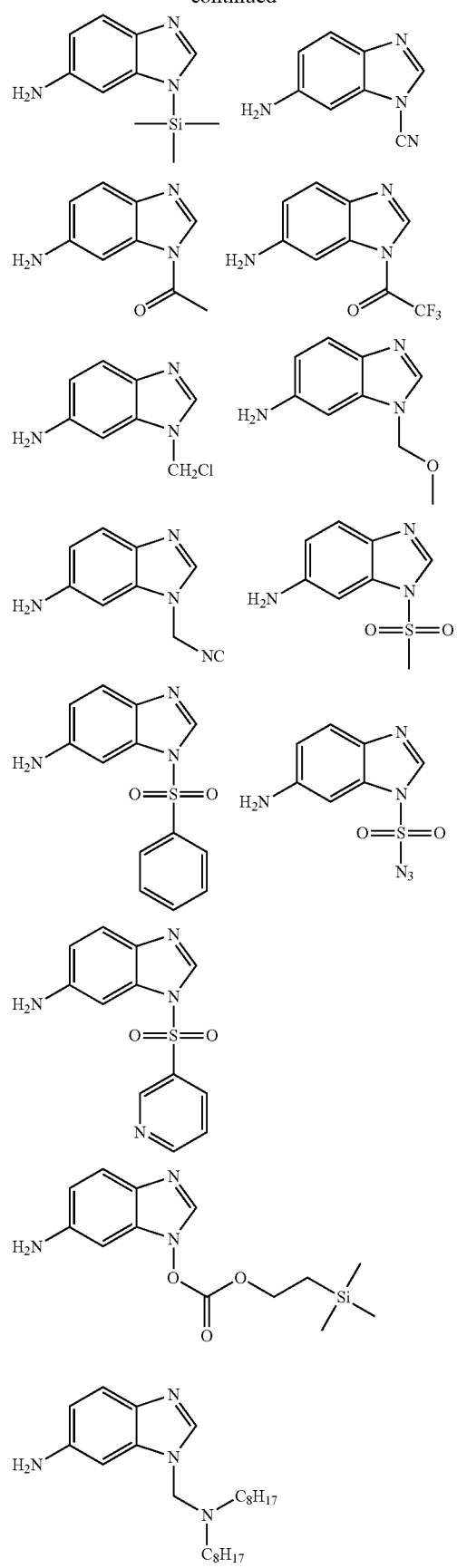
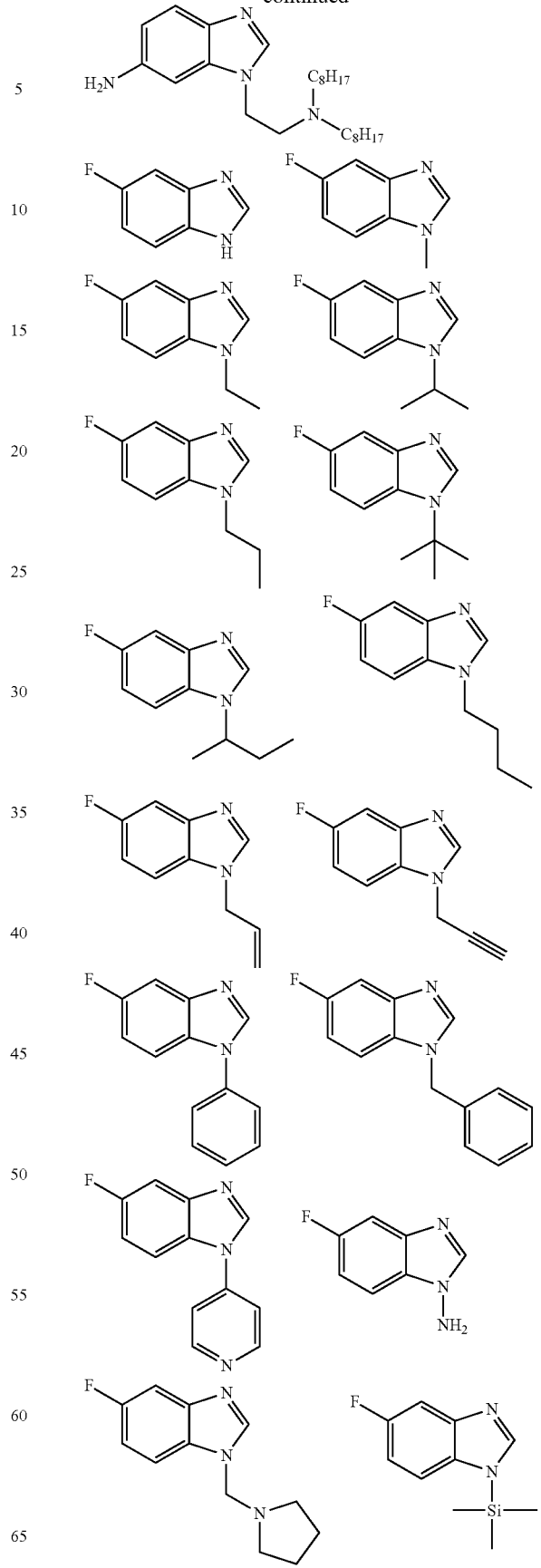

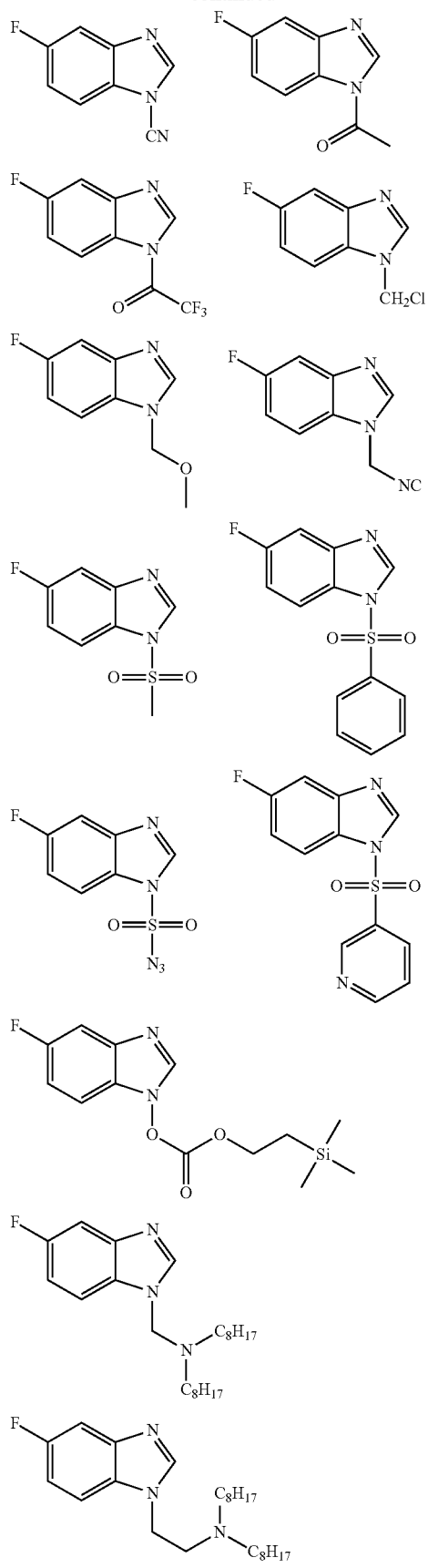
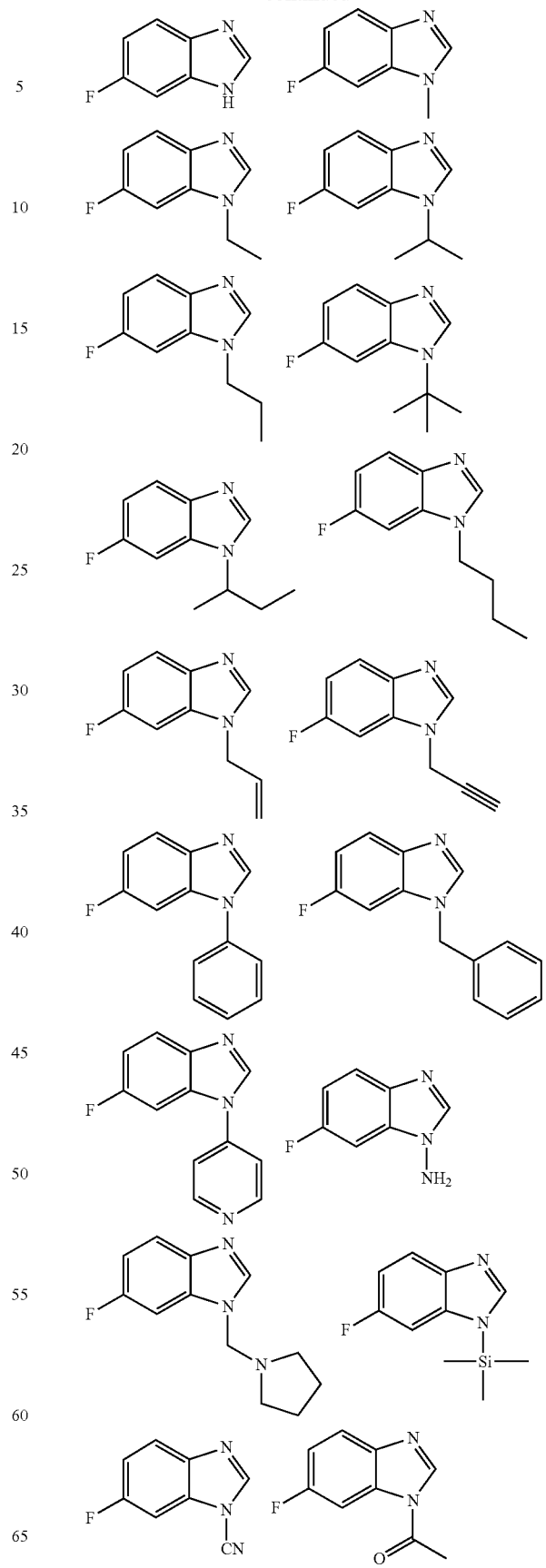

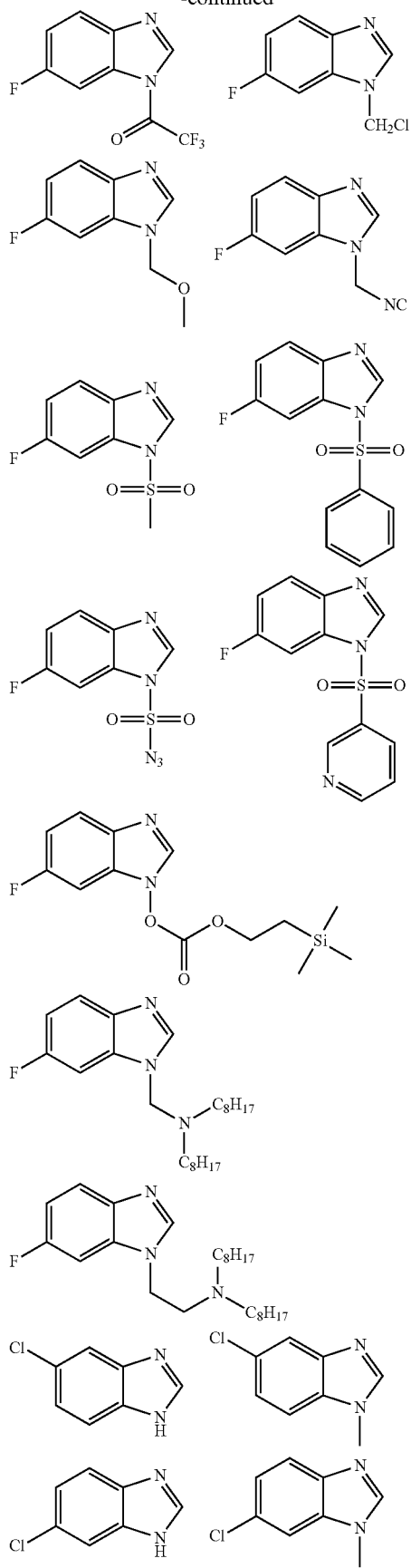
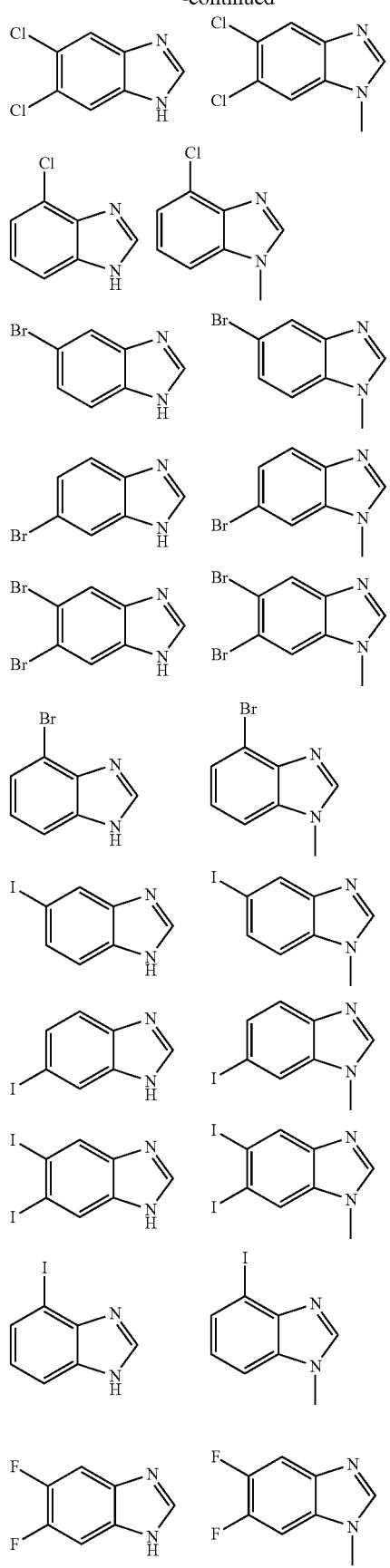

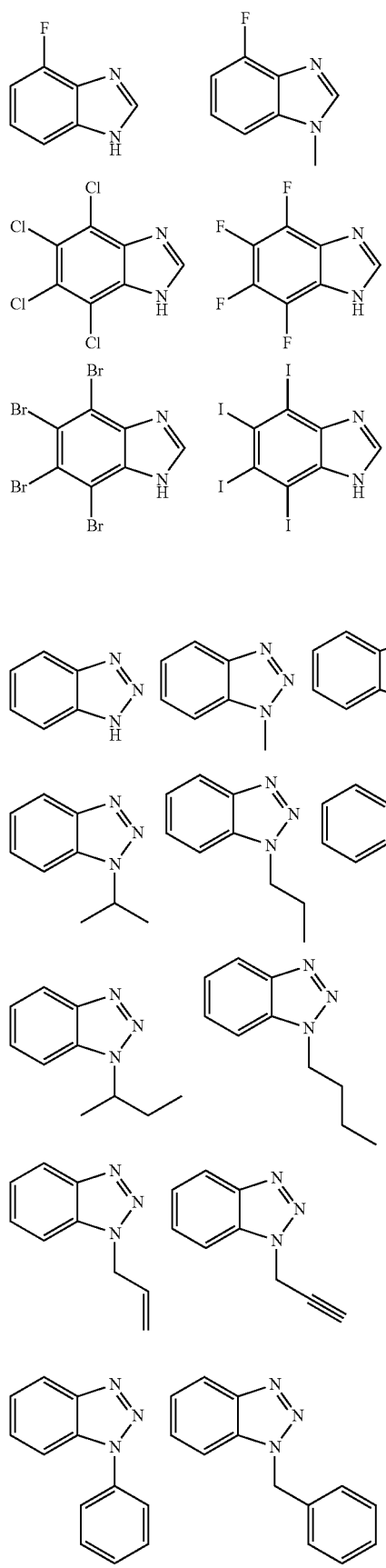
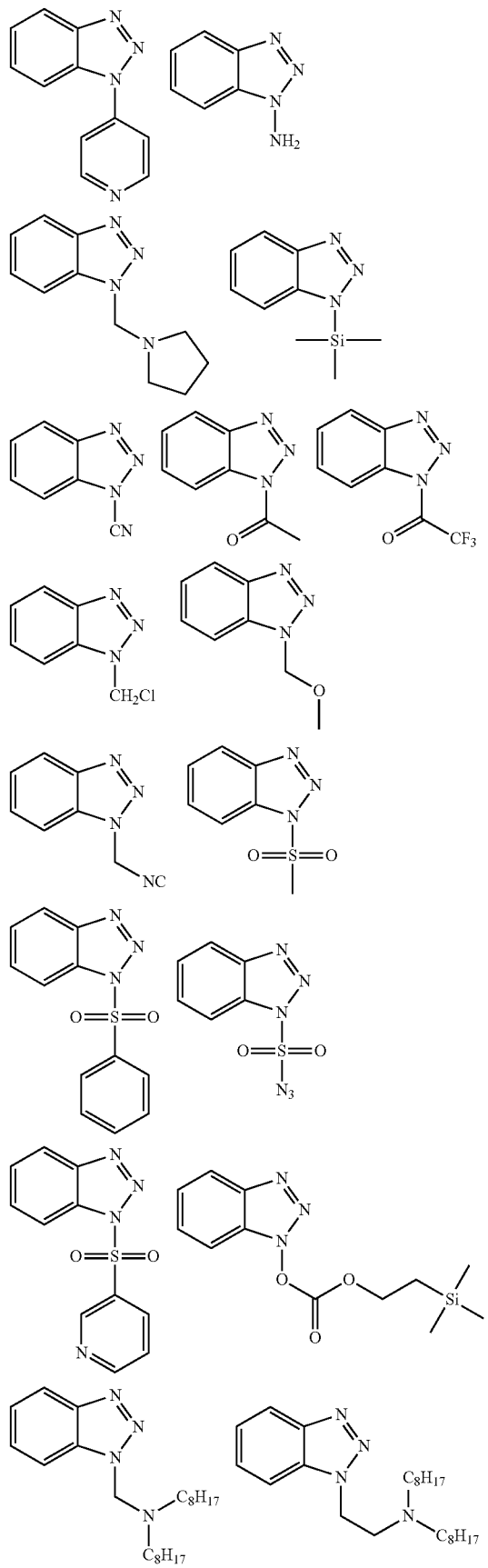

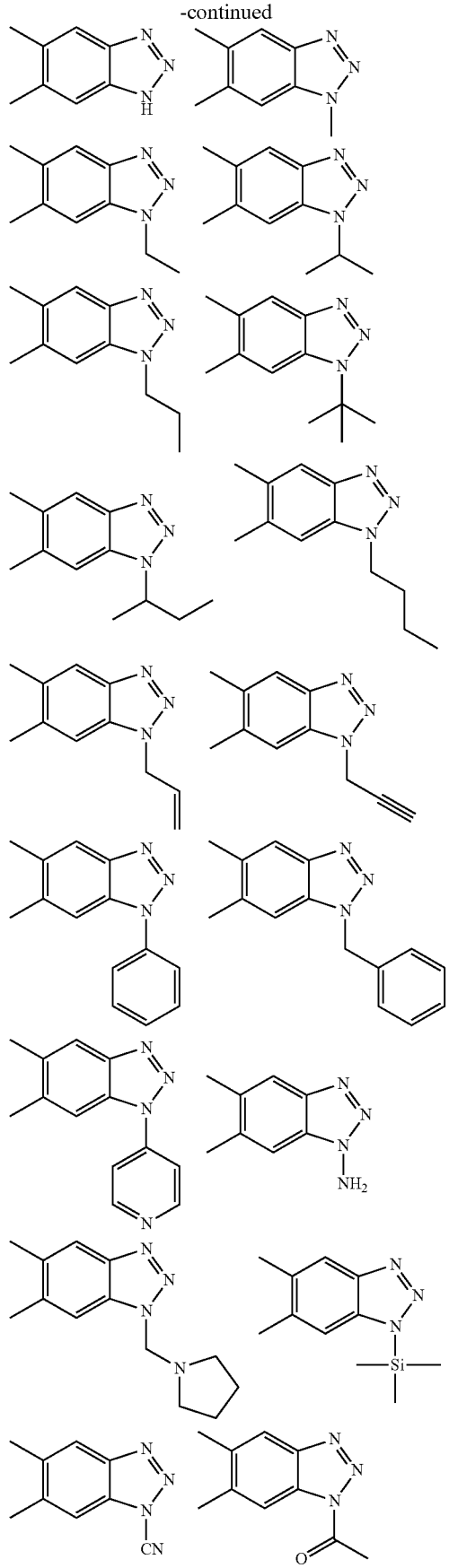
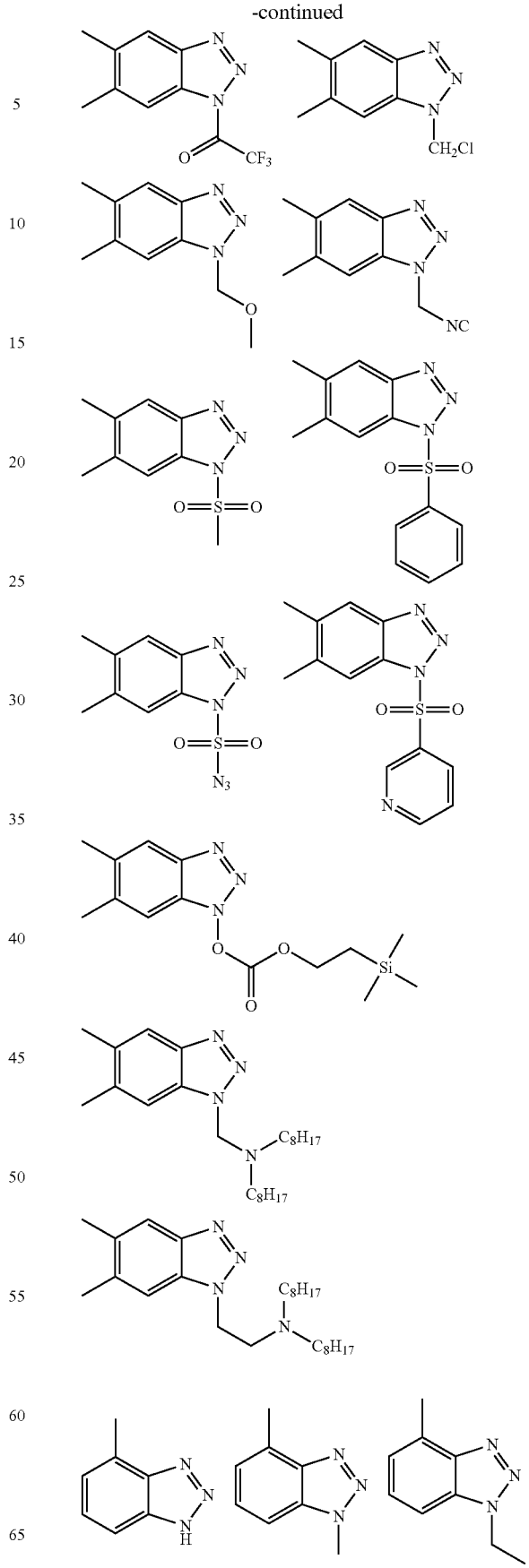

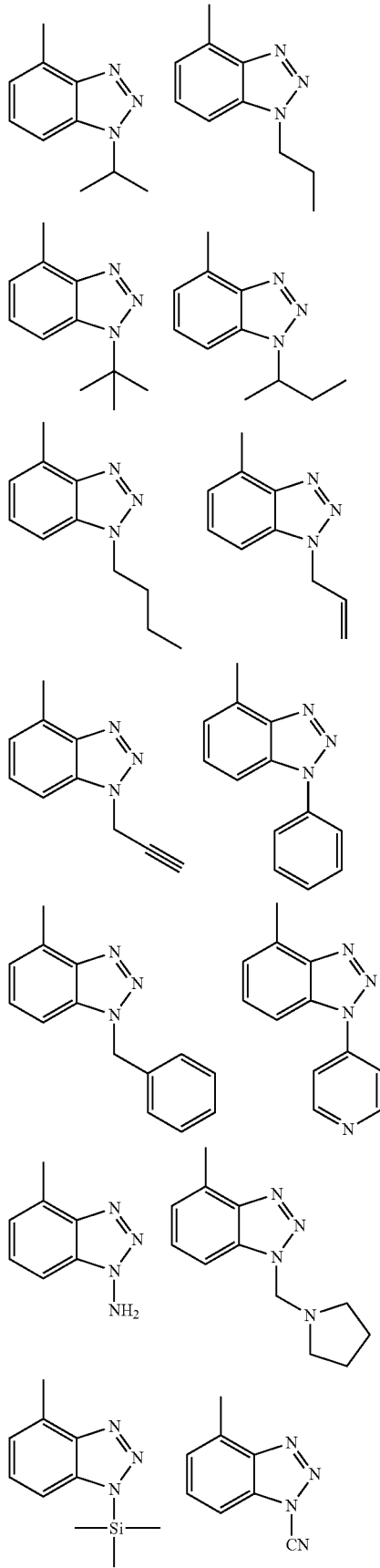
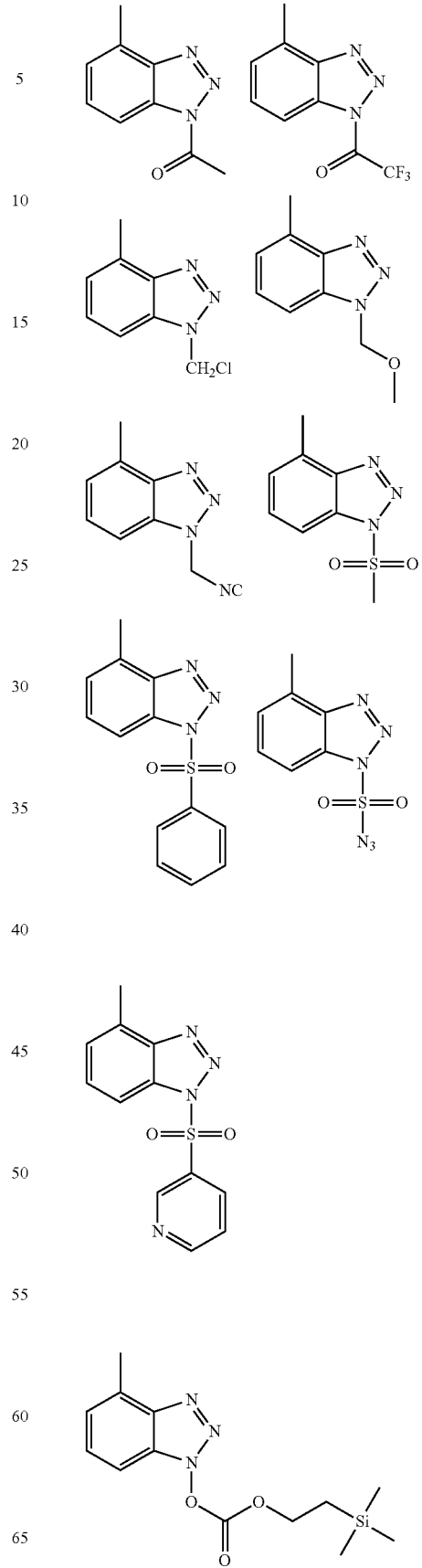

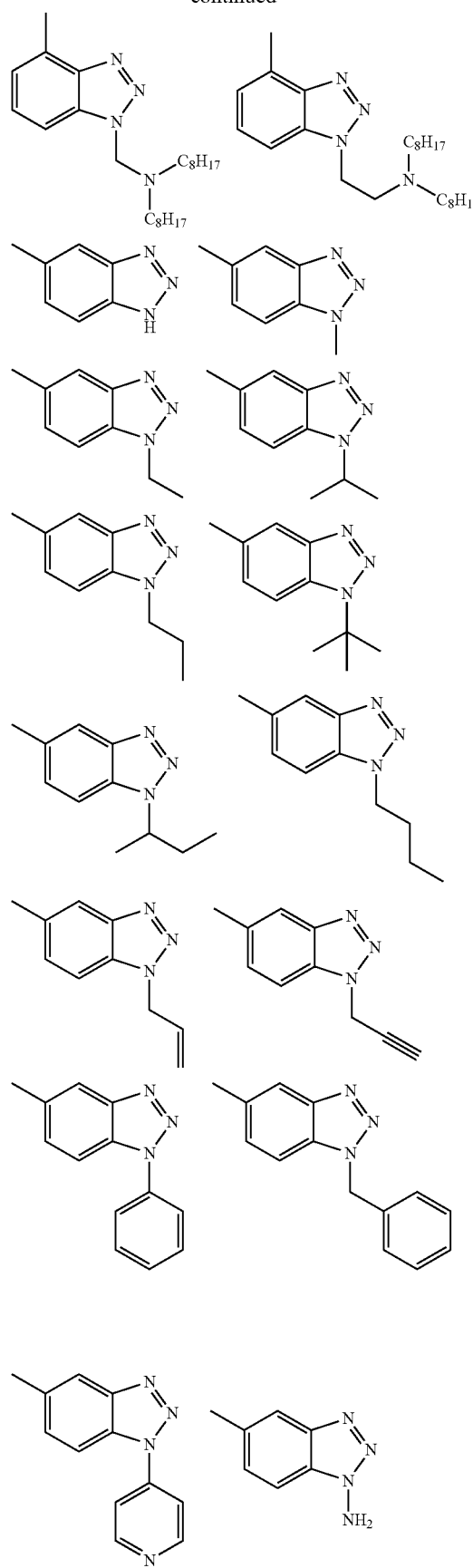
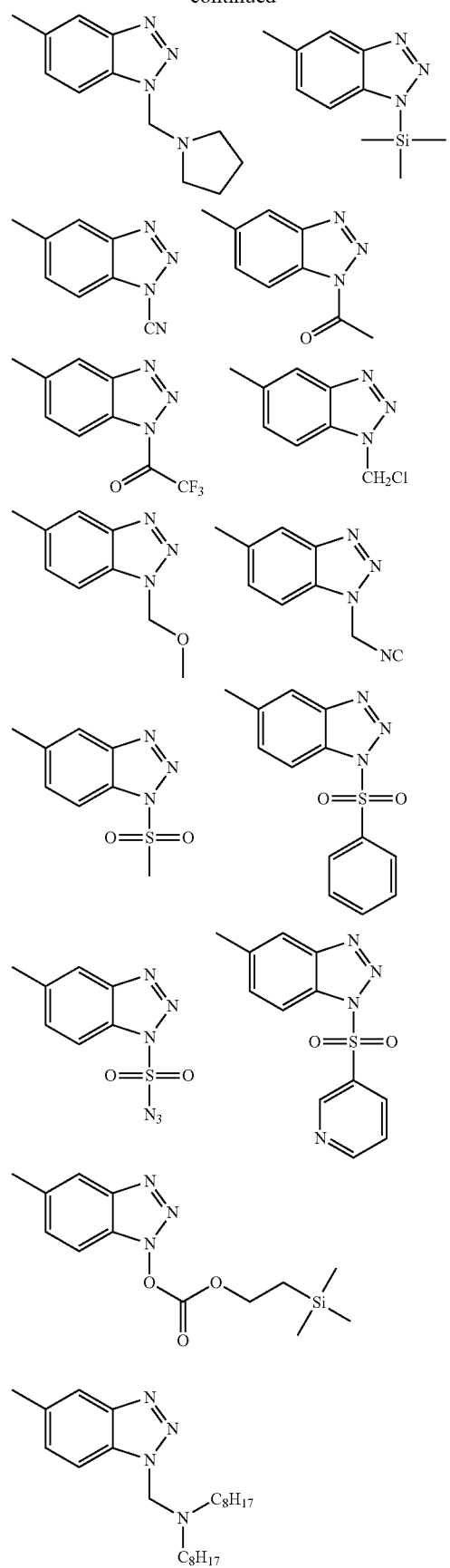

-continued
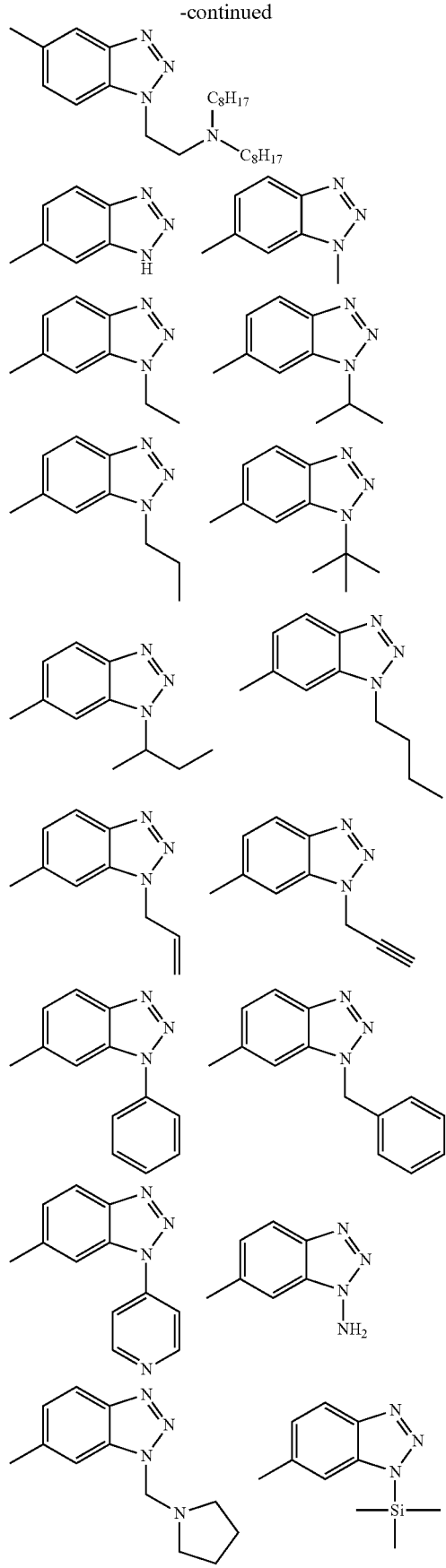
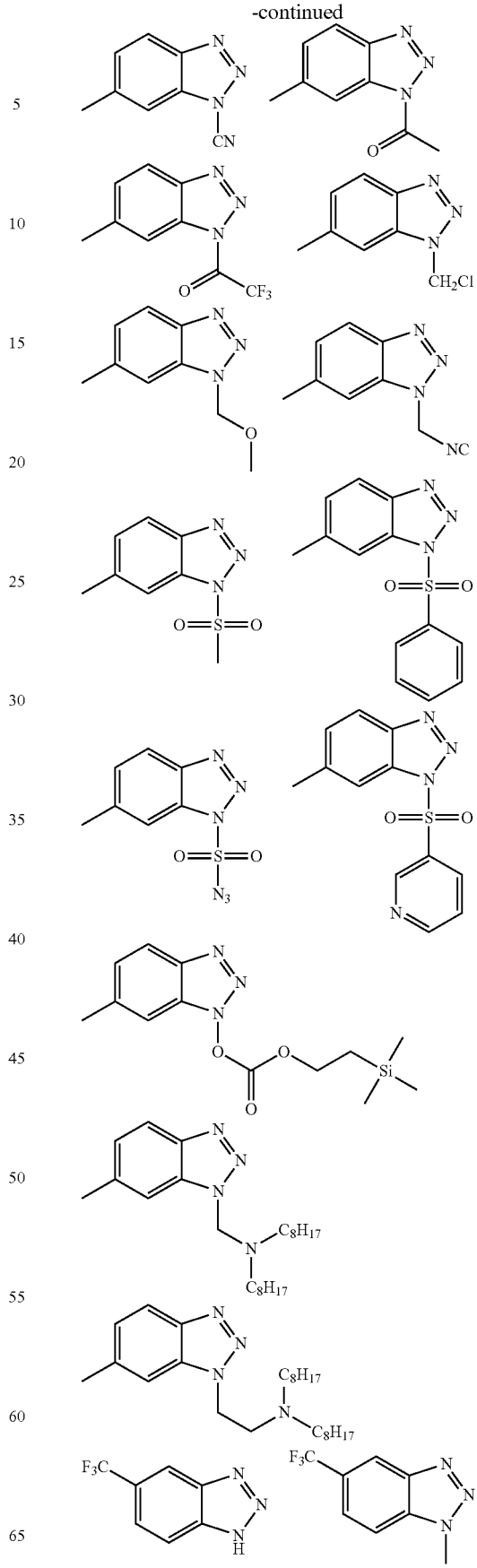

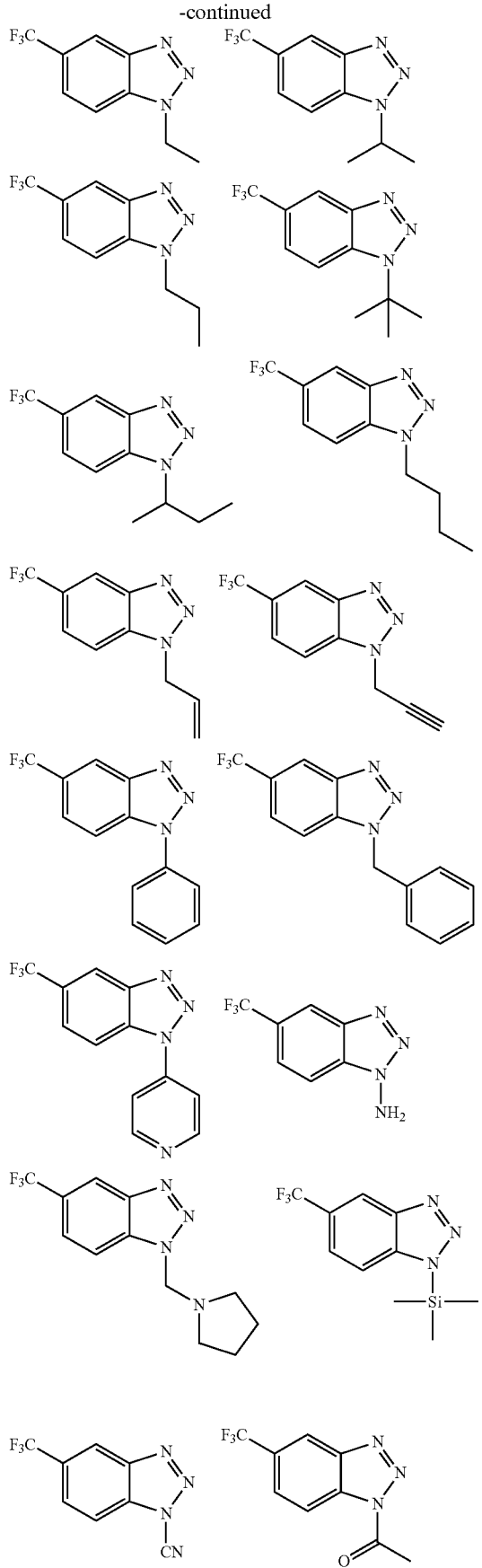
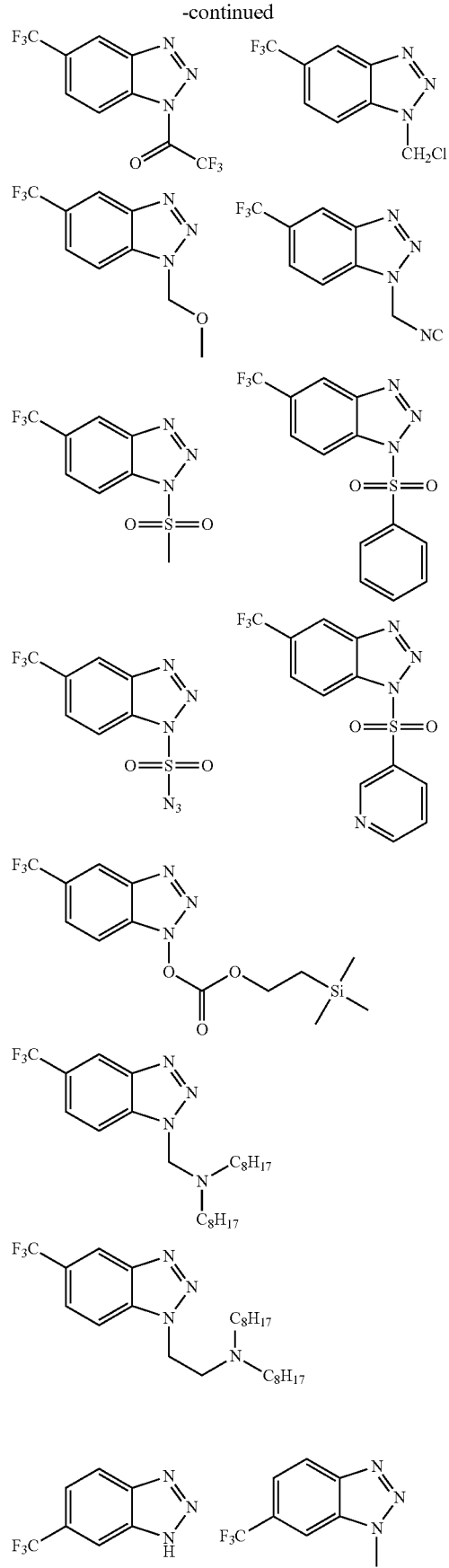

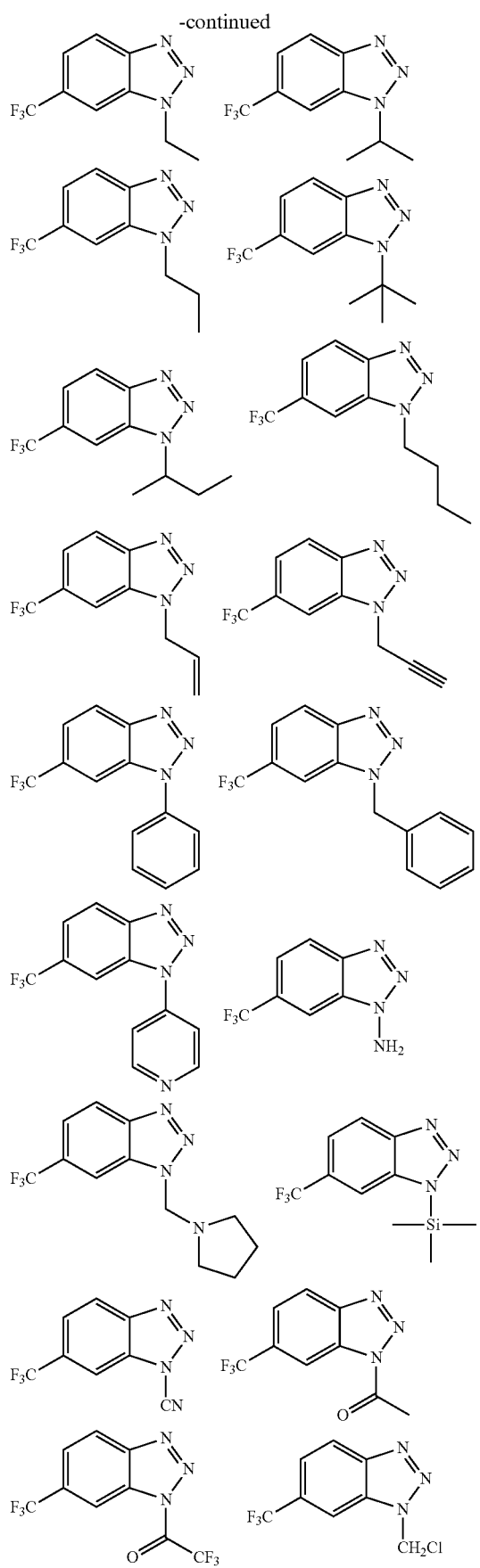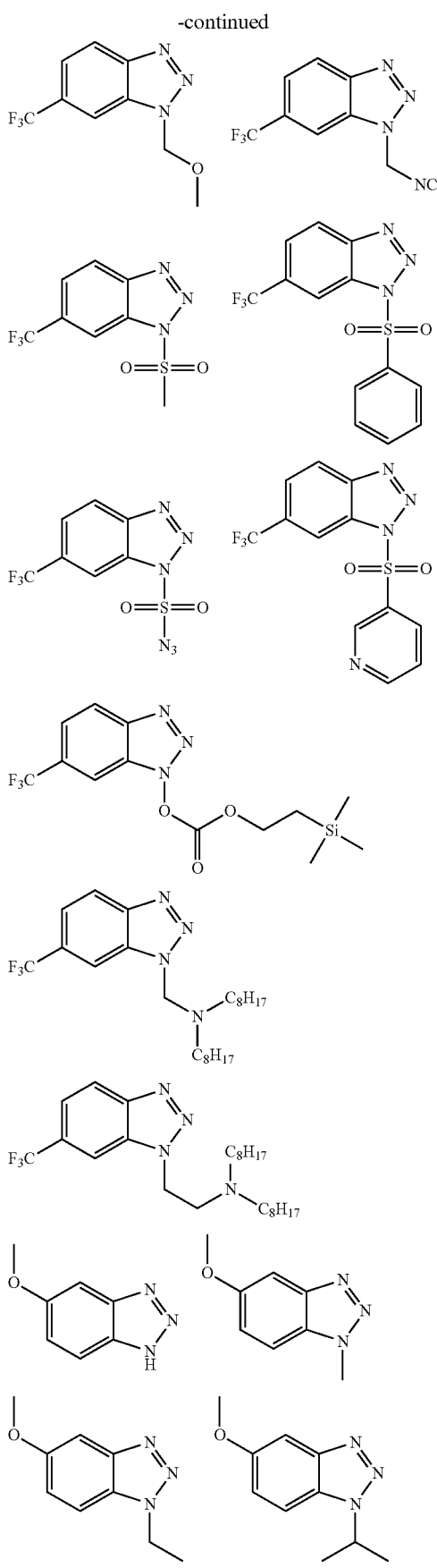

61
-continued
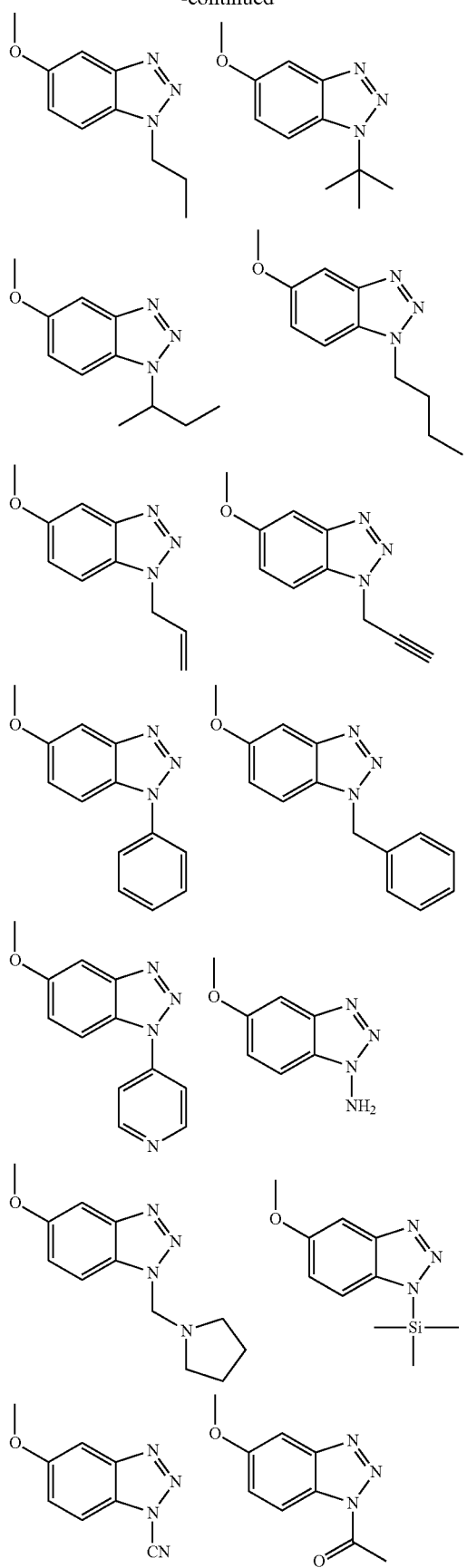
62
-continued
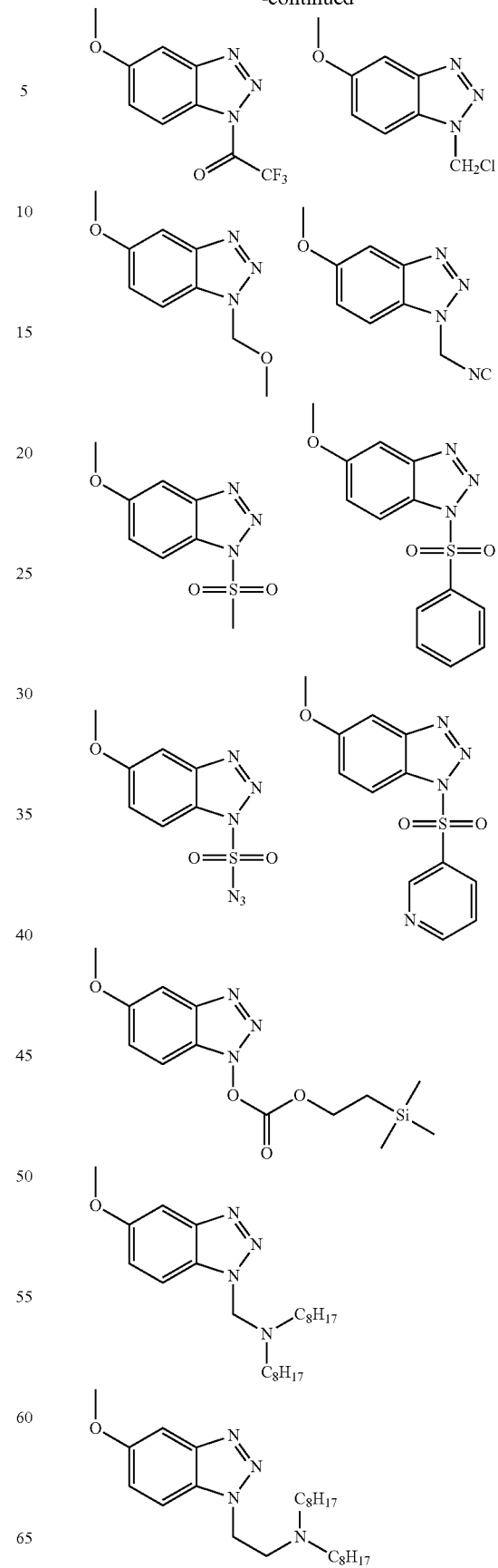

63
-continued
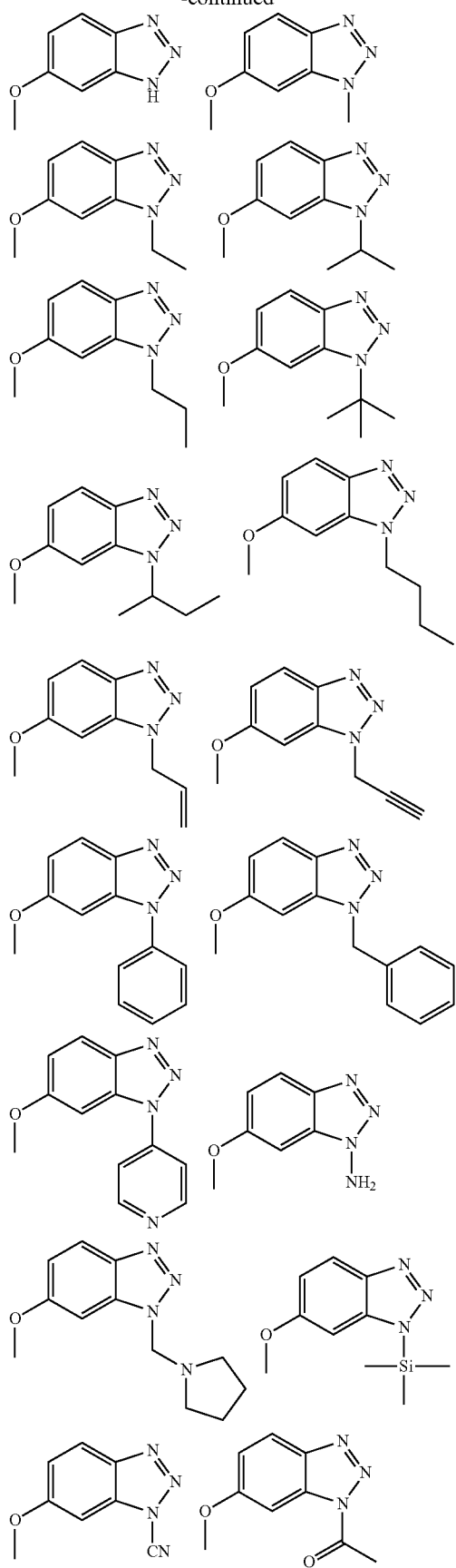
64
-continued
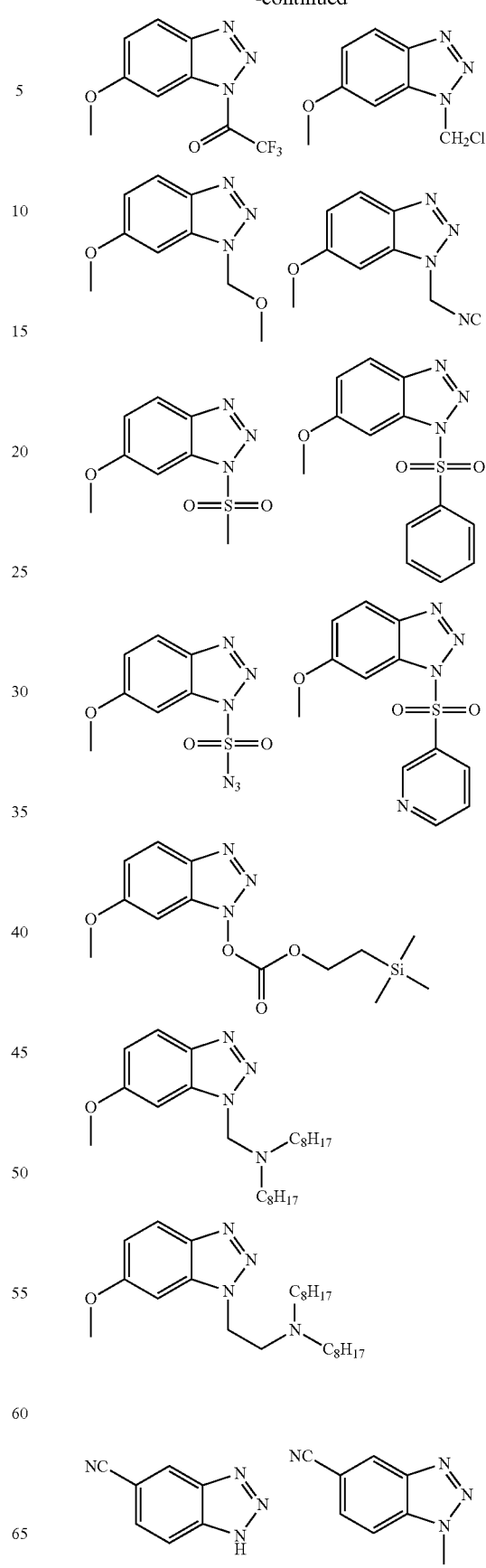

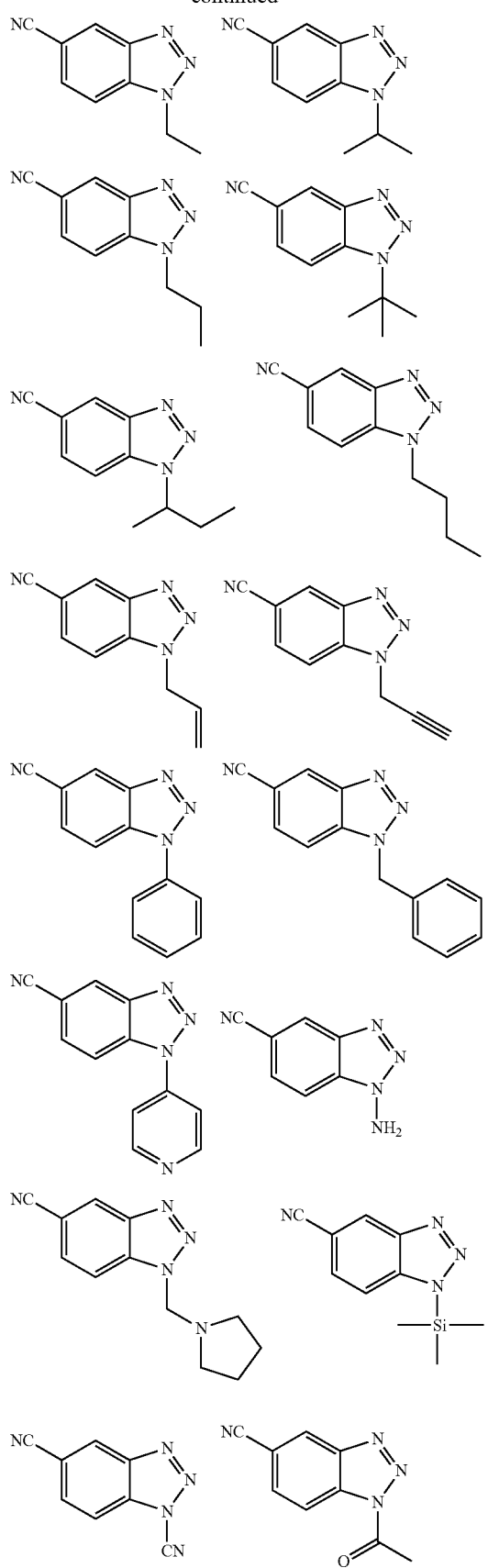
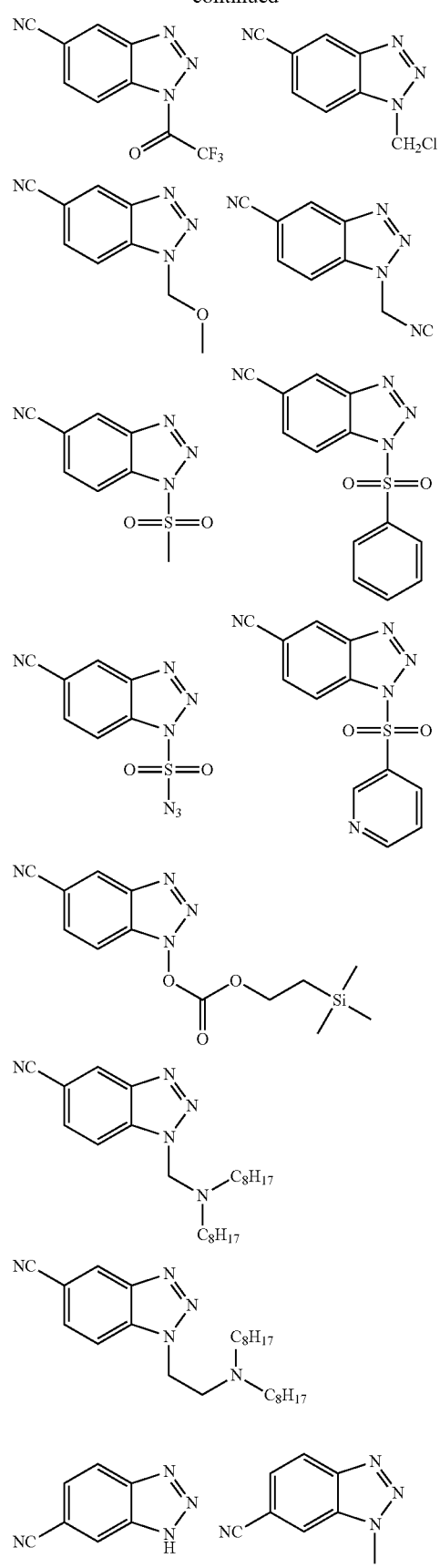

-continued
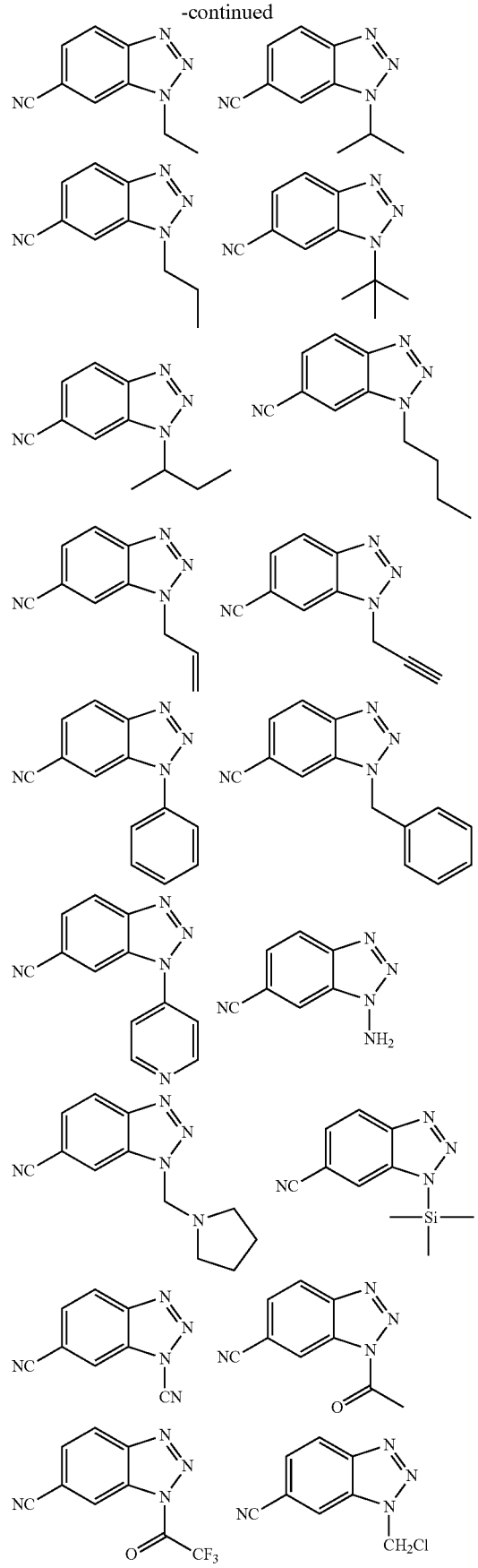
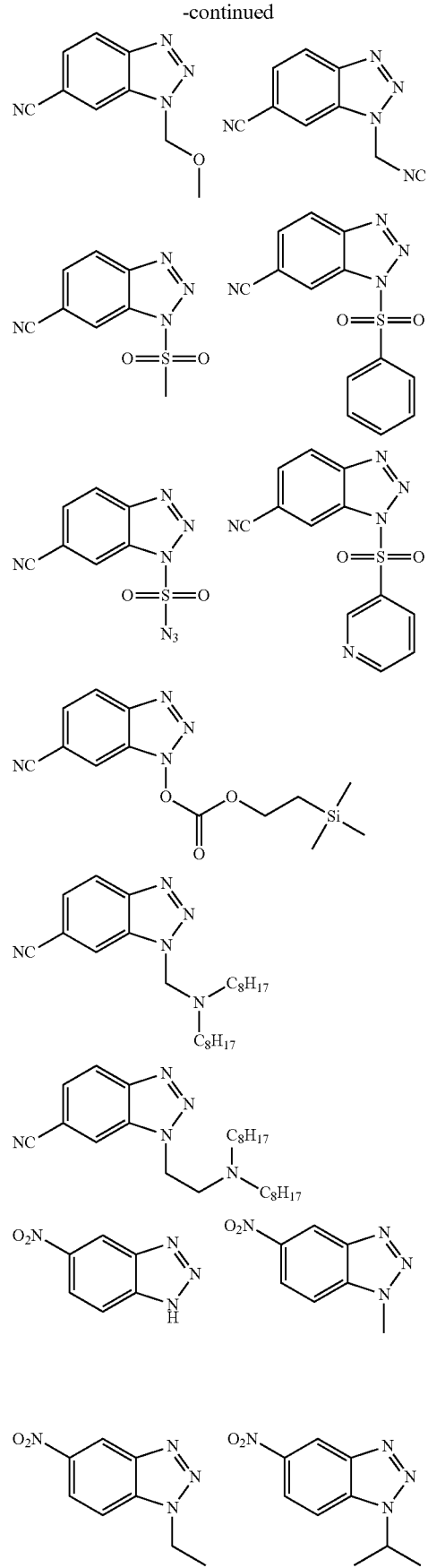

-continued
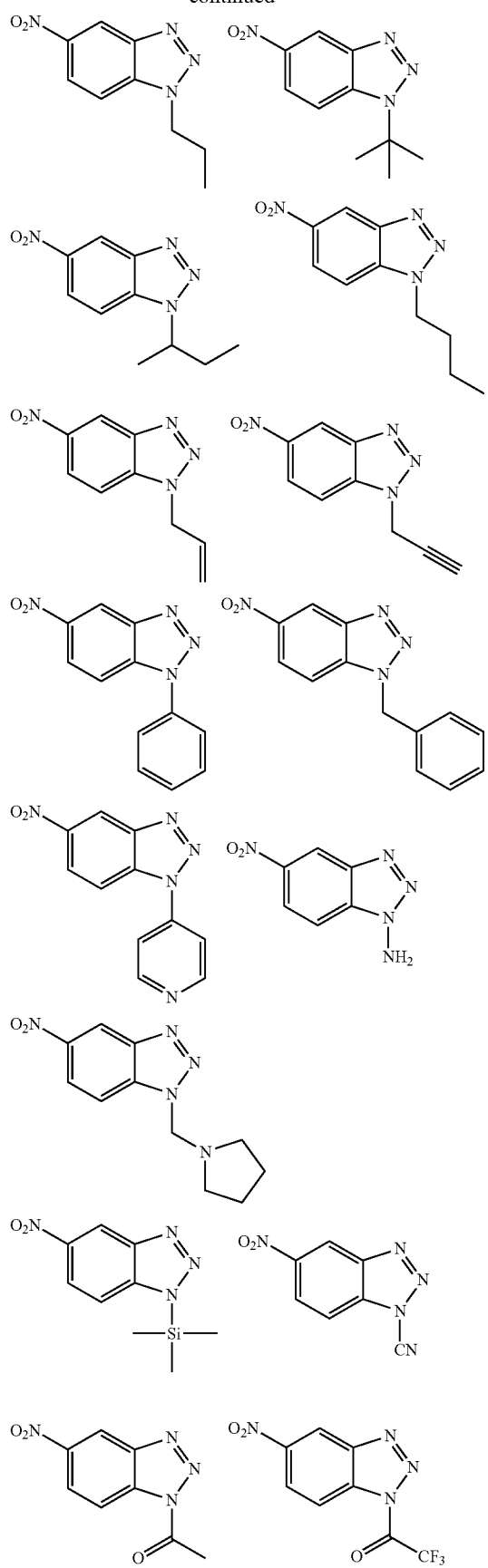
-continued
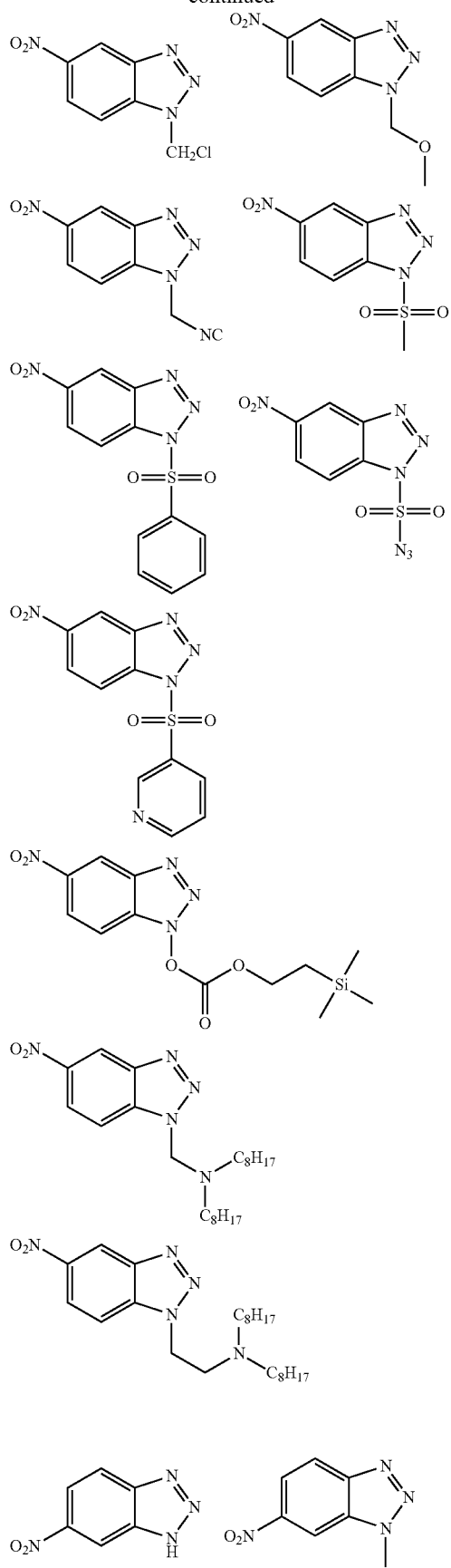

-continued
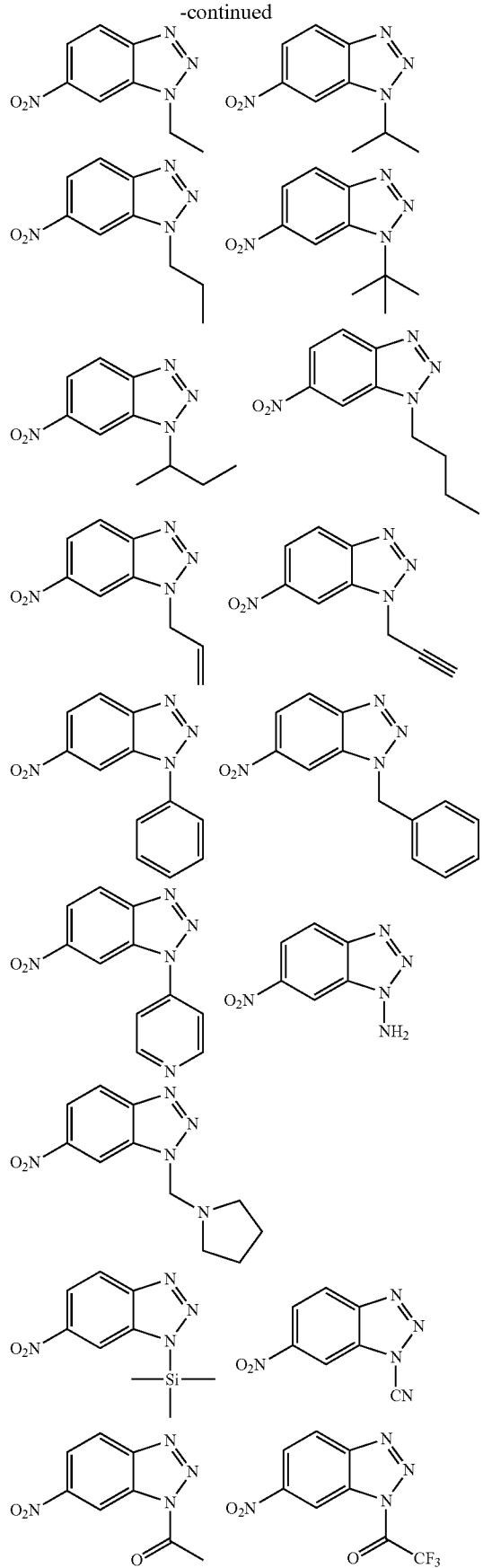
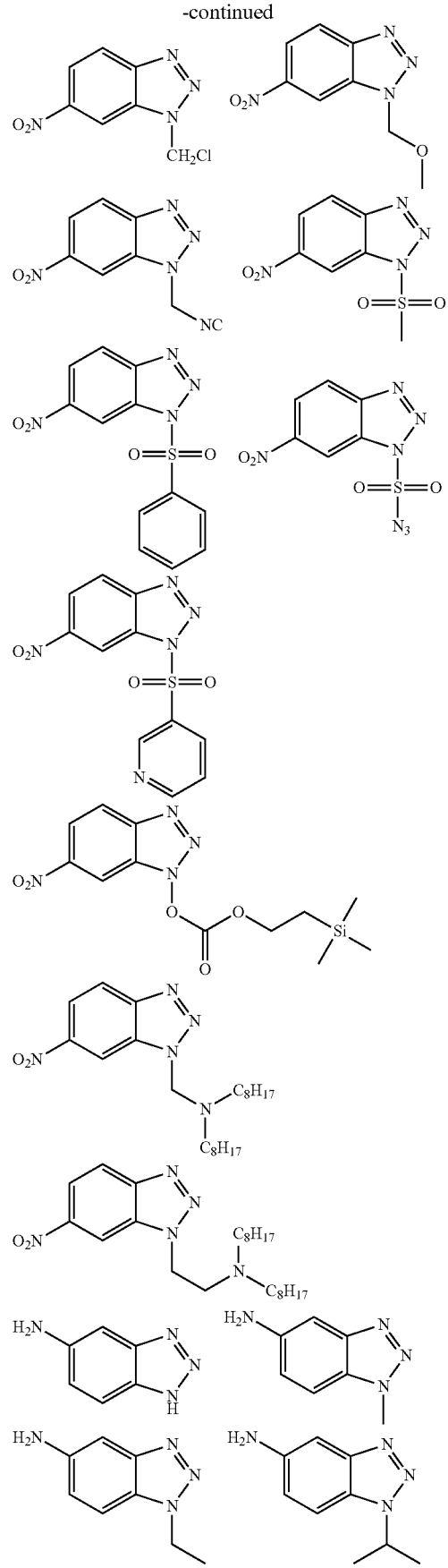

-continued
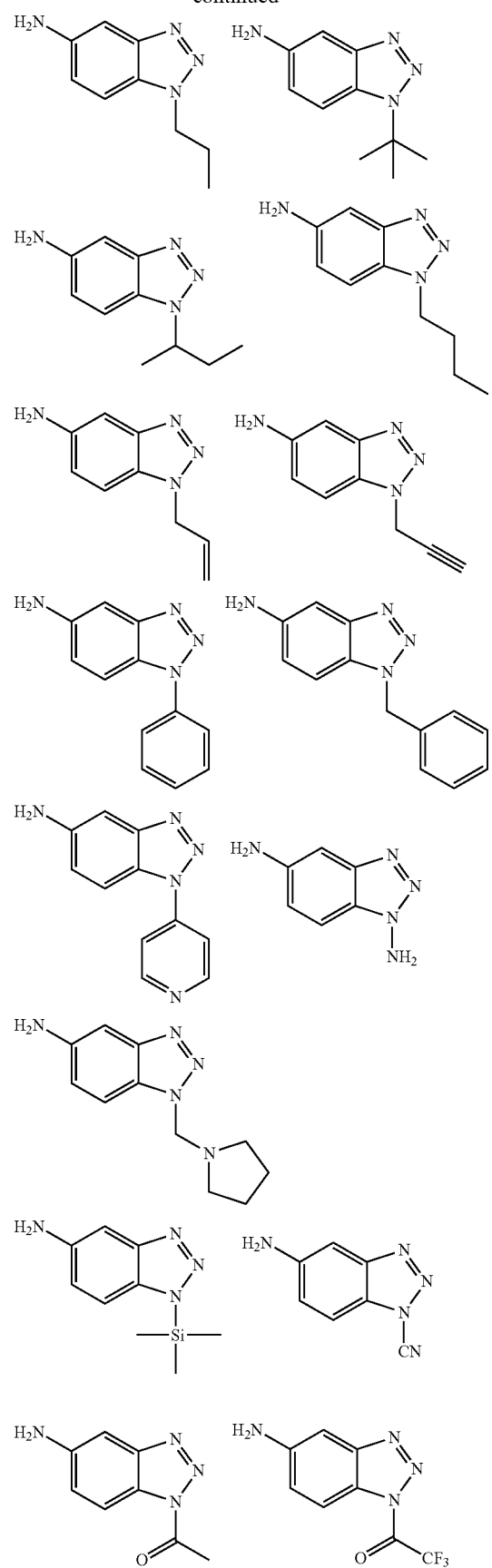
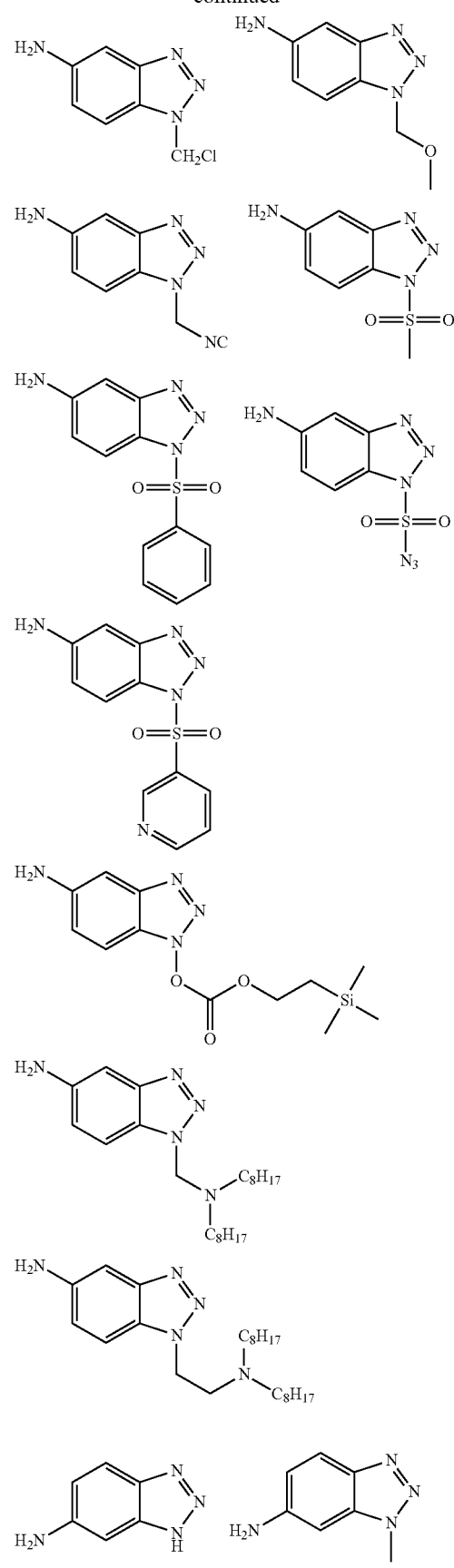

-continued
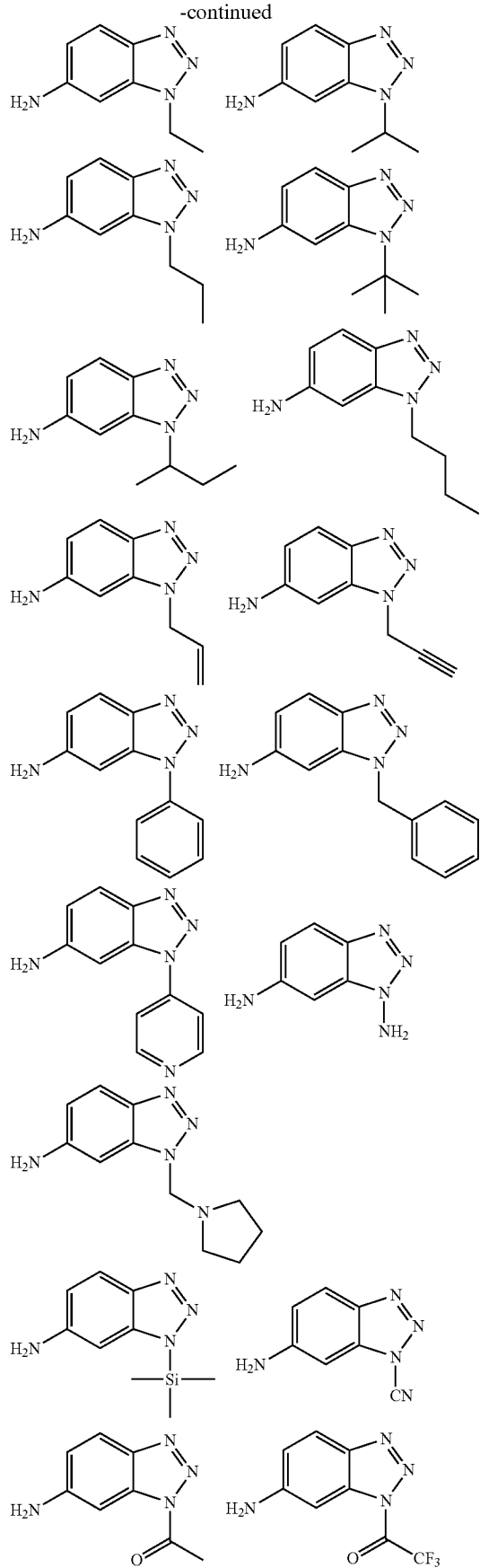
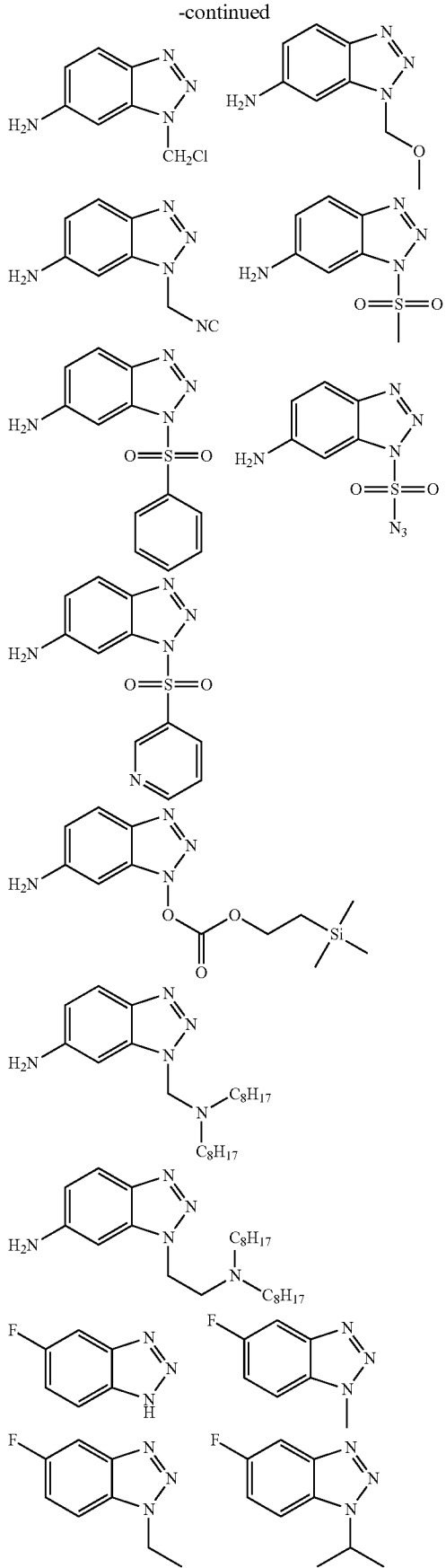

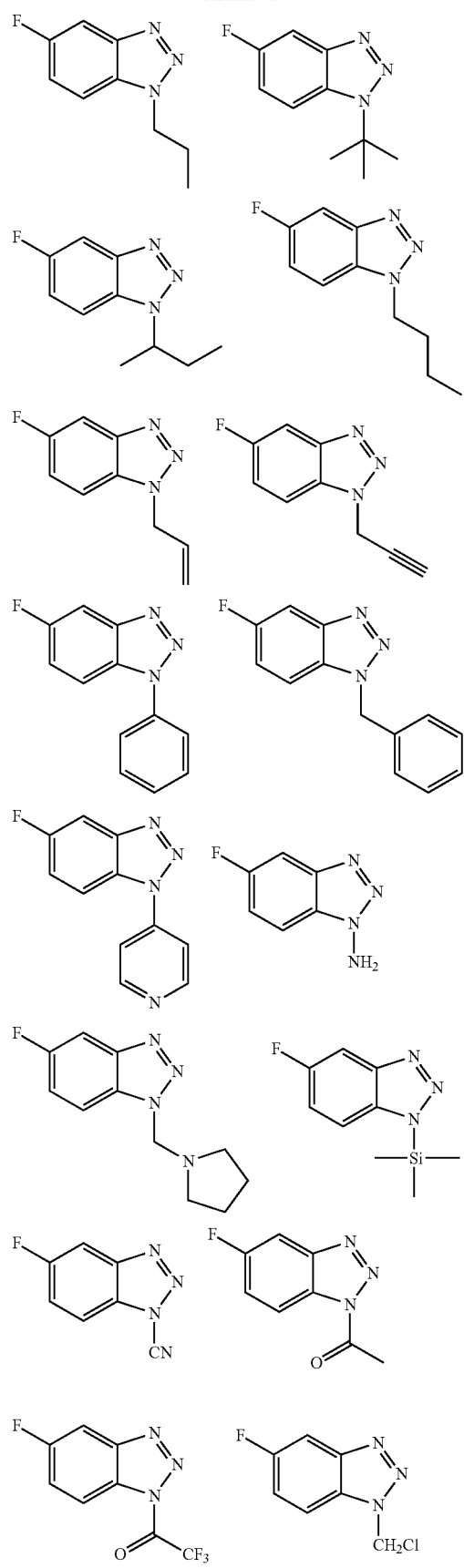
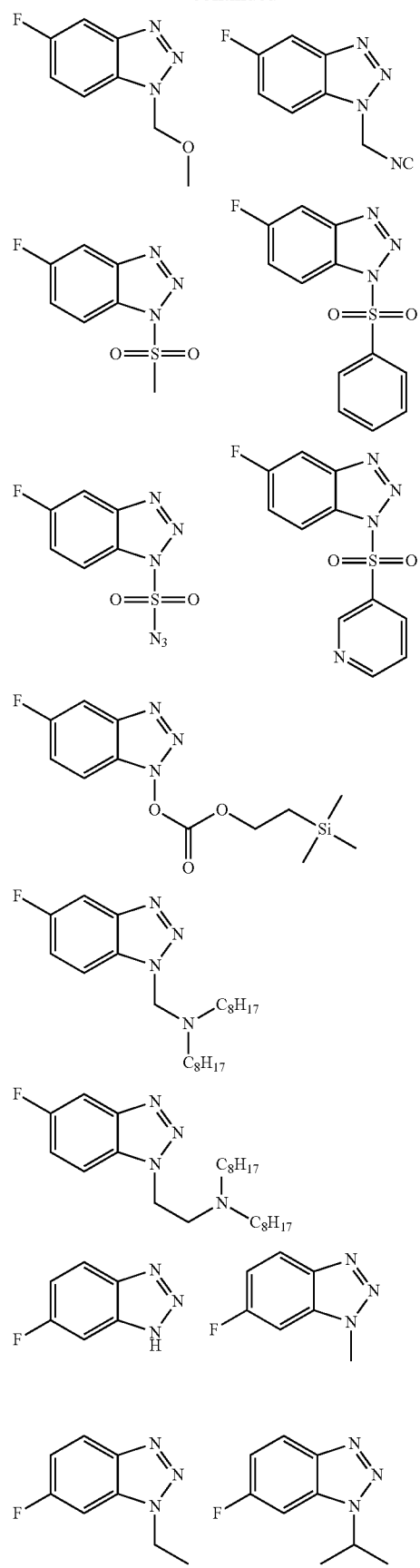

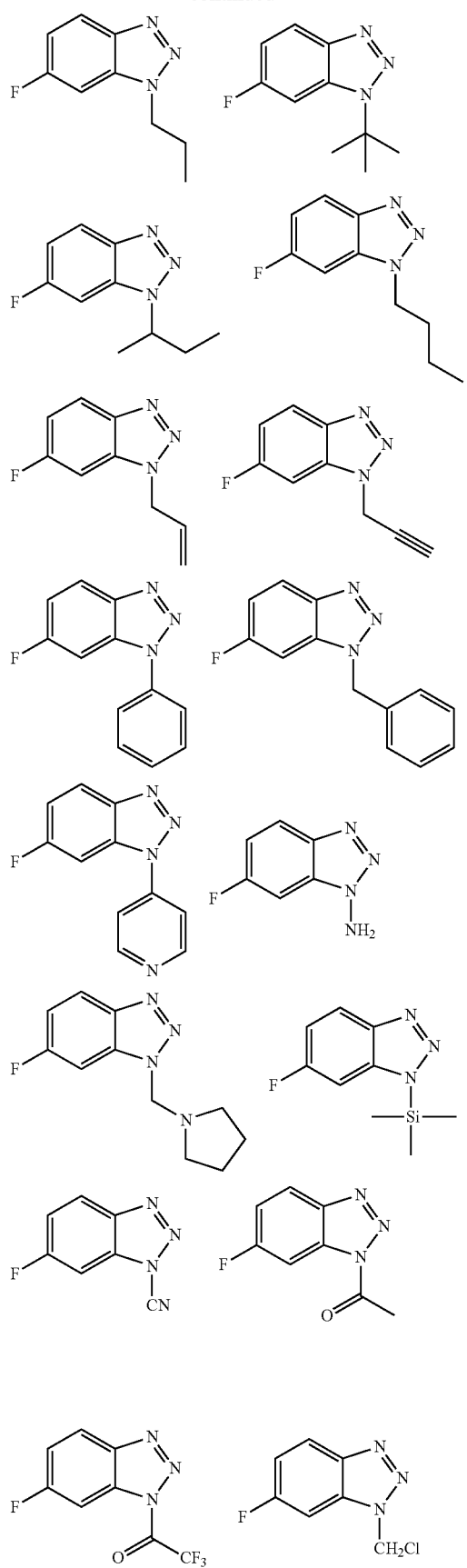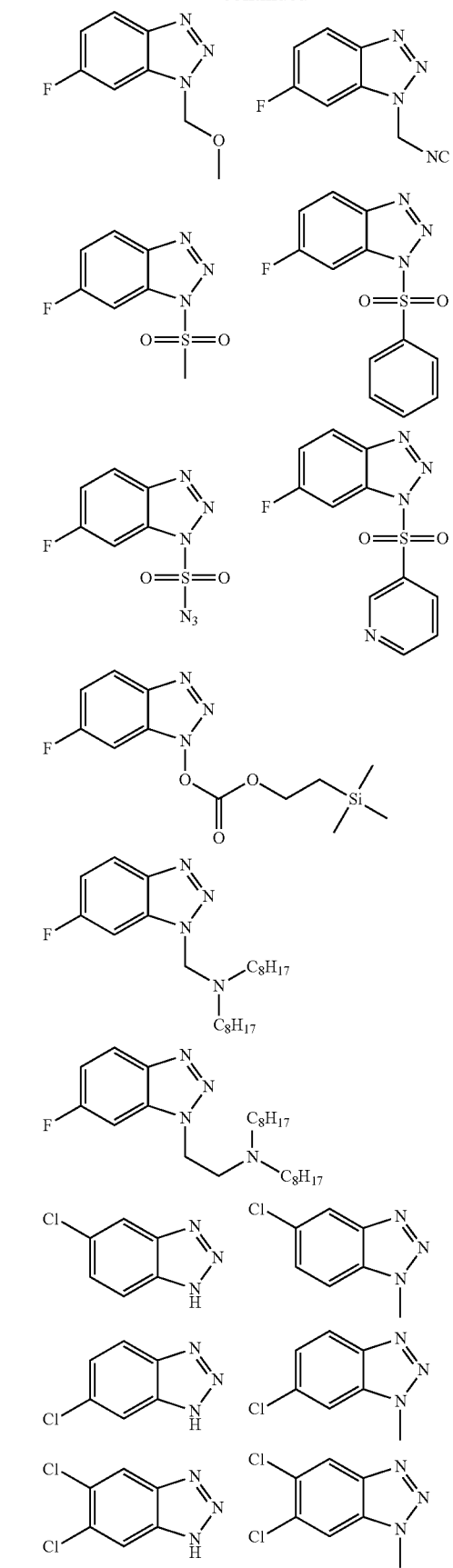

-continued

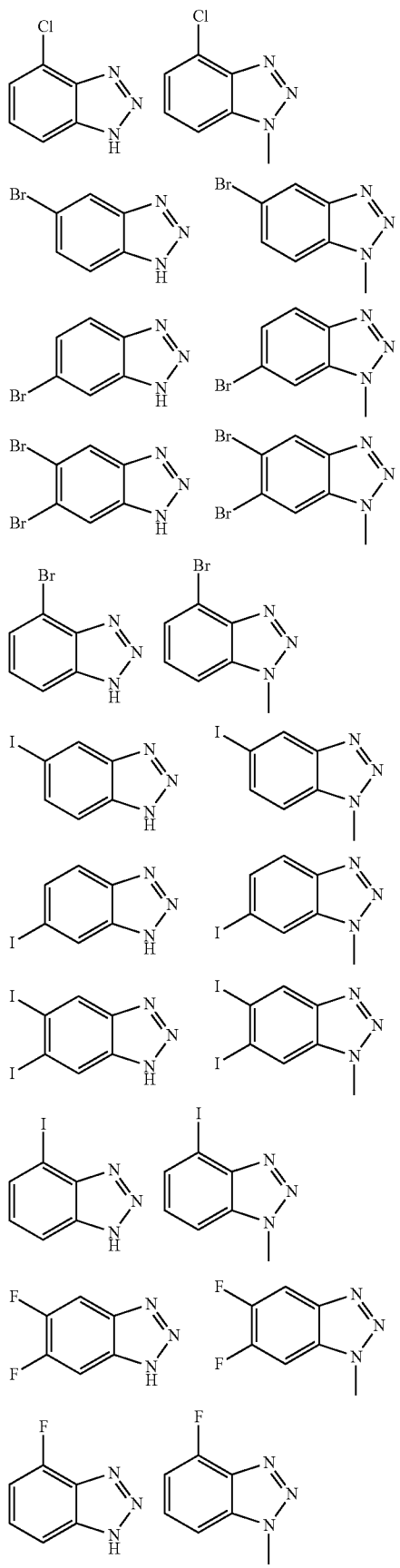

-continued

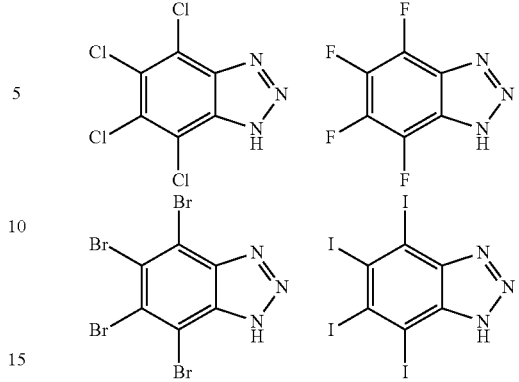

It is preferable that there is no steric hindrance present at the peripheral of nitrogen atom in the nitrogen-containing cyclic compound, in using a compound, which is a double salt of LiF and Lewis acid, as the fluorine-containing inorganic lithium salt. Accordingly, it, is preferable that the fourth site in general formula (1) above is hydrogen atom, and it is more preferable that both of the fourth site and the seventh site are hydrogen atoms. When both of the fourth site and the seventh site in general formula (1) above are hydrogen atoms, substituents at the fifth site and the sixth site in general formula (1) above can be appropriately selected, from the view point of electronic effect exerted on a non-conjugated electron pair present on nitrogen atom. In addition, site numbers of skeleton atoms in the compound represented by general formula (1) above are shown in the following chemical formula as numbers in parentheses.

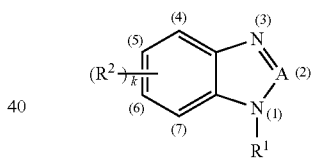

When the non-aqueous electrolyte solution of the present embodiment contains the nitrogen-containing cyclic compounds represented by general formula (1) above, as additives, in the non-aqueous electrolyte solution containing acetonitrile, having excellent balance between viscosity and the dielectric constant, and the fluorine-containing inorganic lithium salt, generation of complex cations composed of a transition metal and acetonitrile can be suppressed, excellent load characteristics can be exhibited, as well as increase in internal resistance upon repeated charge-discharge cycles can be suppressed.

Content of the nitrogen-containing cyclic compound in the electrolyte solution of the present embodiment is not especially limited; however, it is preferably 0.01 to 10% by mass, more preferably 0.02 to 5% by mass, and further preferably 0.05 to 3% by mass, based on the total amount of the electrolyte solution. The nitrogen-containing cyclic compound in the present embodiment suppresses generation of complex cations composed of a transition metal and acetonitrile. Accordingly, the non-aqueous secondary battery containing the nitrogen-containing cyclic compound exerts excellent load characteristics, as well as suppresses increase in internal resistance upon repeated charge-discharge cycles. However, the nitrogen-containing cyclic compound in the present embodiment has not necessarily high solubility caused by influence of a n conjugated plane thereof. Accordingly, by adjusting content of the nitrogen-containing cyclic compound within the range, a generation reaction of the complex cations at the electrode surface can be suppressed, and increase in internal resistance associated with charge-discharge can be decreased, without impairing fundamental function as the non-aqueous secondary battery. By preparing the electrolyte solution in such a composition as above, there is tendency that a further good state of all of cycling performance, high rate performance under low-temperature environment, and other battery characteristics of the resulting non-aqueous secondary battery can be attained.

<2-5. Other Optional Additives>

In the present embodiment, with the object of improving charge-discharge cycle characteristics, enhancement of high-temperature storability, safety (for example, overcharge prevention, etc.), etc., of the non-aqueous secondary battery, optional additives selected from, for example, an acid anhydride, a sulfonate ester, diphenyl disulfide, cyclohexylbenzene, biphenyl, fluorobenzene, tert-butylbenzene, a phosphate ester, [e.g., ethyl diethyl phosphono acetate (EDPA): $(C_2H_5O)_2(P=O)-CH_2(C=O)OC_2H_5$, tris(trifluoroethyl) phosphate (TFEP): $(CF_3CH_2O)_3P=O$, triphenyl phosphate (TPP): $(C_6H_5O)_3P=O$, etc.], etc., and derivatives of these compounds may also be appropriately contained in the non-aqueous electrolyte solution. Particularly, the phosphate ester has action of suppressing a side reaction during storage, and is thus effective.

<3. Positive Electrode>

The positive electrode 5 is composed of the positive electrode active material layer 5A prepared from the positive electrode mixture, and the positive electrode current collector 5B. The positive electrode 5 is not especially limited, as long as being the one acting as the positive electrode of the non-aqueous secondary battery, and may be the known one.

The positive electrode active material layer 5A contains the positive electrode active material, and if necessary, further contains a conductive auxiliary agent and a binder.

It is preferable that the positive electrode active material layer 5A contains a material capable of occluding and releasing lithium ions, as the positive electrode active material. It is preferable that the positive electrode active material layer 5A contains the conductive auxiliary agent and the binder, as needed, together with the positive electrode active material. Using such a material is preferable, because it has tendency of enabling to acquire high voltage and high energy density.

The positive electrode active material includes, for example, a lithium-containing compound each represented by the following general formulae (3a) and (3b):

(3a)

(3b)

{wherein M represents one or more types of metal elements containing at least one type of a transition metal element, x represents number of 0 to 1.1, and y represents number of 0 to 2.}, and the other lithium-containing compound.

The lithium-containing compounds represented by each of general formulae (3a) and (3b) include, for example, lithium/cobalt oxide represented by $LiCoO_2$; lithium/manganese oxide represented by $LiMnO_2$, $LiMn_2O_4$, and $Li_2Mn_2O_4$; lithium/nickel oxide represented by $LiNiO_2$; a lithium-containing composite metal oxide represented by $Li_zMO_2$ (M contains at least one type of transition metal elements selected from Ni, Mn, and Co, and represents two or more types of metal elements selected from Ni, Mn, Co, Al, and Mg, and z represents number over 0.9, and less than 1.2.), etc.

A lithium-containing compound other than the lithium-containing compounds each represented by general formulae (3a) and (3b) is not especially limited, as long as it contains lithium. Such a lithium-containing compound includes, for example, a composite oxide containing lithium and, a transition metal element; a metal chalcogenide having lithium; a phosphate-metal compound having lithium and a transition metal element; and a silicate-metal compound containing lithium and a transition metal element (for example, $Li_tM_uSiO_4$, wherein M has the same definition as that in general formula (3a), t represents number of 0 to 1, and u represents number of 0 to 2). From the standpoint of obtaining higher voltage, as such a lithium-containing compound, in particular, the composite oxide containing lithium and at least one type of a transition metal element selected from the group consisting of cobalt (Co), nickel (Ni), manganese (Mn), iron (Fe), copper (Cu), zinc (Zn), chromium (Cr), vanadium (V), and titanium (Ti); and the phosphate-metal compound are preferable.

As the lithium-containing compound, more specifically, the composite oxide containing lithium and a transition metal element, or the metal chalcogenide having lithium and a transition metal element, and the phosphate-metal compound having lithium are more preferable, including, for example, the compounds each represented by the following general formulae (4a) and (4b):

(4a)

(4b)

{wherein D represents oxygen or a chalcogen element, $M^I$ and $M^{II}$ each represent one or more types of a transition metal element, value of v and w are different depending on a charge-discharge state of a battery, and v represents number of 0.05 to 1.10, and w represents number of 0.05 to 1.10.}.

The lithium-containing compound represented by general formula (4a) above has a layer-like structure, and the compound represented by general formula (4b) above has an olivine structure. With the object of stabilizing the structure, etc., these lithium-containing compounds may be the one in which a part of the transition metal elements is substituted with Al, Mg, or other transition metal element, the one in which these metal elements are contained in grain boundaries, the one in which a part of oxygen atoms is substituted with fluorine atom etc., the one in which at least a part of the surface of the positive electrode active material is covered with other positive electrode active material, etc.

The positive electrode active material in the present embodiment may use only such a lithium-containing compound as above, and may use other positive electrode active materials in combination with the lithium-containing compound.

The other positive electrode active material includes, for example, a metal oxide having a tunnel structure and a layer-like structure, or the metal chalcogenide; sulfur; a conductive polymer, etc. The metal oxide having the tunnel structure and the layer-like structure, or the metal chalcogenide includes, for example, an oxide, sulfide, selenide, etc., of a metal other than lithium, represented by $MnO_2$, $FeO_2$, $FeS_2$, $V_2O_5$, $V_6O_{13}$, $TiO_2$, $TiS_2$, $MoS_2$, and $NbSe_2$. The conductive polymer is represented by, for example, polyaniline, polythiophene, polyacetylene, and polypyrrol.

The other positive electrode active material may be used as one type alone, or as two or more types in combination, and is not especially limited. However, it is preferable that the positive electrode active material layer contains at least one type of a transition metal element selected from Ni, Mn and Co, since they reversibly and stably enable occlusion and release of lithium ions, and achieve high energy density.

When the lithium-containing compound and other positive electrode active material are used in combination, as the positive electrode active materials, use ratio of the lithium-containing compound is preferably 80% by mass or more, more preferably 85% by mass or more, relative to the total parts of the positive electrode active material including the lithium-containing compound and the other positive electrode active material.

The conductive auxiliary agent includes, for example, graphite, carbon black represented by acetylene black, and Ketjen black, as well as carbon fiber. Containing ratio of the conductive auxiliary agent is preferably 10 parts by mass or less, more preferably 1 to 5 parts by mass, relative to 100 parts by mass of positive electrode active material.

The binder includes, for example, polyvinylidene fluoride (PVDF), polytetrafluoroethylene (PTFE), polyacrylic acid, styrene-butadiene rubber, and fluorocarbon-rubber. Containing ratio of the binder is preferably 6 parts by mass or less, more preferably 0.5 to 4 parts by mass, relative to 100 parts by mass of the positive electrode active material.

The positive electrode active material layer 5A is formed by coating the positive electrode mixture-containing slurry, in which the positive electrode mixture, obtained by mixing the positive electrode active material and, if necessary, the conductive auxiliary agent and the binder, are dispersed in a solvent, to the positive electrode current collector 5B, drying it (i.e., removal of solvent), and pressing it if necessary. Such a solvent is not especially limited, and the conventionally known one can be used, including, for example, N-methyl-2-pyrrolidone, dimethylformamide, dimethylacetamide, water, etc.

The positive electrode current collector 5B is composed of a metal foil, for example, an aluminum foil, a nickel foil, a stainless foil, etc. The positive electrode current collector 5B may be carbon coated on the surface, or may be fabricated to a mesh-like structure. Thickness of the positive electrode current collector 5B is preferably 5 to 40 μm, more preferably 7 to 35 μm, and further preferably 9 to 30 μm.

<4. Negative Electrode>

The negative electrode 6 is composed of the negative electrode active material layer 6A prepared from the negative electrode mixture, and the negative electrode current collector 6B. The negative electrode 6 is not especially limited, as long as it functions as the negative electrode of the non-aqueous secondary battery, and may be the known one.

In view of capability of increasing battery voltage, it is preferable that the negative electrode active material layer 6A contains a material in which lithium ions can be occluded at a potential less than 0.4 V vs. Li/Li$^+$ as the negative electrode active material. It is preferable that the negative electrode active material layer 6A contains the conductive auxiliary agent and the binder, if necessary, together with the negative electrode active material.

The negative electrode active material includes, for example, metal lithium, a metal oxide, a metal nitride, a lithium alloy, a tin alloy, a silicon alloy, an intermetallic compound, an organic compound, an inorganic compound, a metal complex, an organic polymer compound, etc., other than carbon materials represented by amorphous carbon (hard carbon), artificial graphite, natural graphite, graphite, pyrolytic carbon, coke, glassy carbon, a baked product of an organic polymer compound, meso carbon microbeads, carbon fiber, activated carbon, graphite, carbon colloid, and carbon black.

The negative electrode active material may be used as one type alone, or as two or more types in combination.

The conductive auxiliary agent includes graphite, carbon black, represented by, for example, acetylene black and Ketjen black, as well as carbon fiber. It is preferable that containing ratio of the conductive auxiliary agent is 20 parts by mass or less, and more preferably 0.1 to 10 parts by mass, relative to 100 parts by mass of the negative electrode active material.

The binder includes, for example, PVDF, PTFE, polyacrylic acid, styrene-butadiene rubber, and fluorocarbon rubber. It is preferable that containing ratio of the binder is 10 parts by mass or less, more preferably 0.5 to 6 parts by mass, relative to 100 parts by mass of the negative electrode active material.

The negative electrode active material layer 6A is formed by coating the negative electrode mixture-containing slurry, in which the negative electrode mixture obtained by mixing the negative electrode active material and, if necessary, the conductive auxiliary agent and the binder are dispersed in a solvent, to the negative electrode current collector 6B, drying it (i.e., removal of solvent), and pressing it if necessary. The solvent is not especially limited, and the conventionally known one may be used. It includes, for example, N-methyl-2-pyrrolidone, dimethylformamide, dimethylacetamide, water, etc.

The negative electrode current collector 6B is composed of a metallic foil, for example, a copper foil, a nickel foil, a stainless foil, etc. In addition, the negative electrode current collector 6B may be carbon coated on the surface, and may be fabricated into a mesh shape. Thickness of the negative electrode current collector 6B is preferably 5 to 40 μm, more preferably 6 to 35 μm, and further preferably 7 to 30 μm.

<5. Separator>

It is preferable that the non-aqueous secondary battery 1 in the present embodiment is equipped with a separator 7 between the positive electrode 5 and the negative electrode 6, in view of imparting safety, such as prevention of short circuit between the positive electrode 5 and the negative electrode 6, shut down, etc. As the separator 7, the same as used, in a known non-aqueous secondary battery may be used, and an insulating thin film having high ion transmittance and superior mechanical strength is preferable. The separator 7 includes, for example, woven fabric, non-woven fabric, a microporous membrane made of a synthetic resin, etc., and among them, the microporous membrane made of the synthetic resin is preferable.

As the microporous membrane made of the synthetic resin, a polyolefin-based microporous membrane, such as the microporous membrane containing, for example, polyethylene or polypropylene, as a main component, or the microporous membrane containing, for example, both of these polyolefins, as the main components, is suitably used. The non-woven fabric includes a porous membrane, for example, made of glass, made of ceramics, made of a heat resistant resin, such as a polyolefin, a polyester, a polyamide, a liquid crystalline polyester, an aramide, etc.

The separator 7 may be the one composed of a single layer of or a multi-layer lamination of one type of the microporous membrane, or the one laminated two or more types of the microporous membranes. The separator 7 may be the one composed of a single layer or a multi-layer lamination using a mixed resin material obtained by melt kneading two or more types of resin materials.

<6. Battery Outer Package>

Composition of a battery outer package 2 of the non-aqueous secondary battery 1 in the present embodiment is not especially limited; however, for example, either of the battery outer package of a battery can and an outer packaging structure using laminated film can be used. As the battery can, a metal can, for example, made of steel or aluminum can be used. As the outer packaging structure using laminated film, for example, a laminated film composed of three-layer composition of a molten resin/a metal film/a resin can be used.

The outer packaging structure using laminated film can be used as the outer packaging structure in such a state that the two sheets of molten resin sides are laminated facing inside, or the molten resin side is folded so as to attain a state facing inside, and the end parts are in a encapsulated state by heat seal. In using the outer packaging structure using laminated film, a positive electrode lead structure 3 (or a positive electrode terminal and a lead tab connecting with the positive electrode terminal) may be connected to the positive electrode current collector 5B, and a negative electrode lead structure 4 (or a negative electrode terminal and a lead tab connecting with the negative electrode terminal) may be connected to the negative electrode current collector 6B. In this case, the outer packaging structure using laminated film may be encapsulated in such a state that terminal parts of the positive electrode lead structure 3 and the negative electrode lead structure 4 (or the lead tab connected to each of the positive electrode terminal and the negative electrode terminal) are pulled out to the external part of the outer packaging structure.

<7. Preparation Method for Battery>

The non-aqueous secondary battery 1 in the present embodiment is prepared by a known method, using the non-aqueous electrolyte solution, the positive electrode 5 having the positive electrode active material layer on one surface or both surfaces of the current collector, the negative electrode 6 having the negative electrode active material layer on one surface or both surfaces of the current collector, and the battery outer package 2, as well as the separator 7, as needed.

Firstly, a laminated structure made of the positive electrode 5, the negative electrode 6, as well as the separator 7, as needed, is formed. For example, the following aspects are possible:

An aspect of forming a laminated structure having wound components, by winding a long positive electrode 5 and negative electrode 6, by interposition of the long separator between the positive electrode 5 and the negative electrode 6;

An aspect of forming a laminated structure having stacking components, by alternatingly laminating, via the separator sheet, a positive electrode sheet and a negative electrode sheet, obtained by cutting the positive electrode 5 and the negative electrode 6 into a plurality of sheets having a constant area and shape;

An aspect of forming a laminated structure having stacking components, by alternatingly inserting the positive electrode sheet and the negative electrode sheet between long separators themselves, which had been wound in a zigzag shape.

Next, the non-aqueous secondary battery in the present embodiment can be prepared by accommodating the laminated structure inside the battery outer package 2 (a battery case), pouring the electrolyte solution pertaining to the present embodiment inside the battery case, immersing the laminated structure in the electrolyte solution, and encapsulating it.

Alternatively, the non-aqueous secondary battery 1 can be prepared by preparing, in advance, a gel state electrolyte membrane by impregnating the electrolyte solution in a substrate composed of a polymer material, forming the laminated structure having a laminated structure using a sheet-like positive electrode 5, the negative electrode 6, and the electrolyte membrane, as well as the separator 7, as needed, and then accommodating the laminated structure inside the battery outer package 2.

Shape of the non-aqueous secondary battery 1 in the present embodiment is not especially limited, and for example, a cylinder shape, an elliptical shape, a square tube type, a button shape, a coin shape, a flat shape, a laminate shape, etc., are suitably adopted.

In the present embodiment, when the non-aqueous electrolyte solution using acetonitrile is used, lithium ions released from the positive electrode at the first-time charging of the non-aqueous secondary battery may diffuse throughout the negative electrode, caused by high ion conductivity thereof. In the non-aqueous secondary battery, it is general that area of the negative electrode active material layer is designed larger as compared with the positive electrode active material layer. However, when lithium ions are diffused and occluded even at the area not facing the positive electrode active material layer in the negative electrode active material layer, the lithium ions remain at the negative electrode without being released at the first-time charging. Accordingly, extent of contribution of thus not released lithium ions results in irreversible capacity. From this reason, in the non-aqueous secondary battery using the non-aqueous electrolyte solution containing acetonitrile, there may be the case where the first-time charge-discharge efficiency decreases.

On the other hand, when area of the positive electrode active material layer is larger than or the same as that of the negative electrode active material layer, current concentration tends to occur at the edge part of the negative electrode active material layer, during charging, and lithium dendrite tends to generate.

Ratio of the entire area of the side of the negative electrode active material layer, relative to the area of the region where the positive electrode active material layer and the negative electrode active material layer face each other, is not especially limited; however, from the above reason, it is preferably larger than 1.0 and below 1.1, more preferably larger than 1.002 and below 1.09, further preferably larger than 1.005 and below 1.08, and particularly preferably larger than 1.01 and below 1.08. The first-time charge-discharge efficiency can be improved by making ratio of the whole area of the negative electrode active material layer smaller, relative to the area of the region, where the positive electrode active material layer and the negative electrode active material layer are opposing, in the non-aqueous secondary battery using the non-aqueous electrolyte solution containing acetonitrile.

Making the ratio of the entire area of the negative electrode active material layer small, relative to the area of the region where the positive electrode active material layer and the negative electrode active material layer face each other, means to limit ratio of area of the portion of the negative electrode active material layer not opposing to the positive electrode active material layer. In this way, it is possible to maximally reduce amount of lithium ions occluded at the portion of the negative electrode active material layer not opposing to the positive electrode active material layer, in lithium ions released from the positive electrode at the first-time charging (i.e., the amount of lithium ions is irreversible without being released from the negative electrode at the first-time charging). Accordingly, by designing ratio of the whole area of the negative electrode active material layer within the range, relative to the area of the region, where the positive electrode active material layer and the negative electrode active material layer are opposing, first-time charge-discharge efficiency of a battery can be enhanced, and further generation of the lithium dendrite can be suppressed, while maintaining enhancement of load characteristics of a battery by using acetonitrile.

Figure 3:
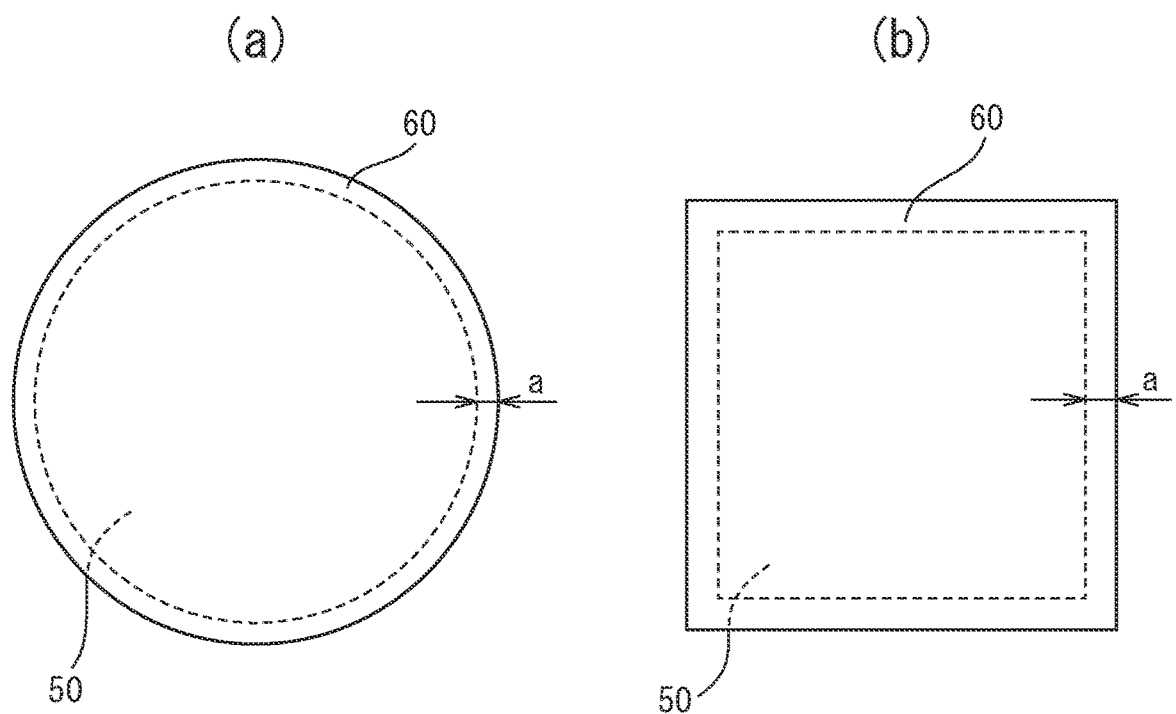
FIG. 3 is a drawing explaining "width of a non-opposing Part of a negative electrode active material layer" in a laminated electrode structure.
Figure 4:
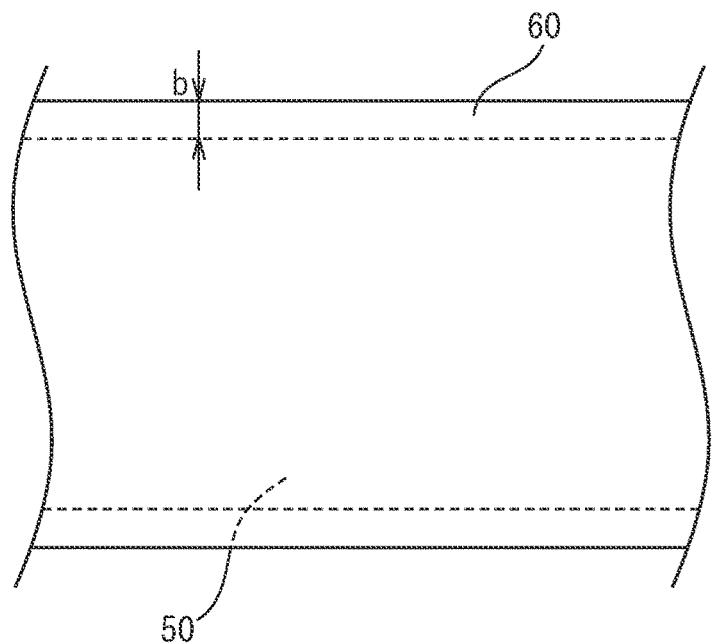
FIG. 4 is a drawing explaining "width of a non-opposing part of a negative electrode active material layer" in a wound-type electrode structure.

FIG. 3 and FIG. 4 show drawings to explain the "width of the non-opposing part of the negative electrode active material layer", in the configuration of the present embodiment where the whole surface of the positive electrode active material layer opposes to the negative electrode active material layer. FIG. 3 is a drawing explaining the case where the electrode structure composed of the positive electrode, the negative electrode and the separator is the laminated electrode structure (the electrode structure composed by only laminating these). FIG. 3(a) shows the case where the positive electrode having a circular positive electrode active material layer 50 in a plan view, and the negative electrode having a circular negative electrode active material layer 60 in a plan view face each other. FIG. 3(b) shows the case where the positive electrode having a square positive electrode active material layer 50 in a plan view, and the negative electrode having a square negative electrode active material layer 60 in a plan view face each other. FIG. 4 is a drawing explaining the case where the electrode structure composed of the positive electrode, the negative electrode and the separator is a wound-type electrode structure formed by winding the laminated structure of these in a vortex state. In these drawings, the current collector of each of the positive electrode and the negative electrode, along with the separator are not shown, in order to easily understand positional relation between the positive electrode active material layer 50 and the negative electrode active material layer 60. In FIG. 4, a part of the opposing area of the positive electrode active material layer 50 and the negative electrode active material layer 60 in the wound-type electrode structure is shown in a plain view.

In FIG. 3, the front side of the drawings (the upper side in a vertical direction to a paper face) is the negative electrode active material layer 60, and the one shown by a dotted line at the depth side is the positive electrode active material layer 50. The "width of the non-opposing part of the negative electrode active material layer" in the laminated electrode structure means distance between the outer peripheral edge of the negative electrode active material layer 60 and the outer peripheral edge of the positive electrode active material layer 50, in a plan view (length "a" in the Fig.).

In FIG. 4 also, similarly as in FIG. 3, the front side of the FIG. 4 is the negative electrode active material layer 60, and the one shown by the dotted line at the, depth side is the positive electrode active material layer 50. A belt-shaped positive electrode and a belt-shaped negative electrode are used in formation of the wound-type electrode structure. This "width of the non-opposing part of the negative electrode active material layer" means distance between the external edge of the negative electrode active material layer 60 and the external edge of the positive electrode active material layer 50, in a direction orthogonal to a longer direction of the belt-shaped positive electrode and the belt-shaped negative electrode (length "b" in the FIG. 4).

In the case where arrangement of electrodes is designed such that an overlapped portion of the outer peripheral edge of the negative electrode active material layer and the outer peripheral edge of the positive electrode active material layer is present, or a too small width portion is present at the non-opposing part of the negative electrode active material layer, deterioration of charge-discharge cycle characteristics in the non-aqueous secondary battery could occur by generation of positional displacement of the electrodes in battery assembling. Accordingly, it is preferable that, in the electrode structure in the non-aqueous secondary battery, the positions of the electrodes are fixed using, in advance, tapes, such as a polyimide tape, a polyphenylene sulfide tape, a PP tape, or adhesives, etc.

The non-aqueous secondary battery 1 in the present embodiment is capable of functioning as a battery by the first-time charging. A method for the first-time charging is not especially limited. However, it is preferable that the first-time charging is carried out at 0.001 to 0.3 C, more preferable carried out at 0.002 to 0.25 C, and further preferable carried out at 0.003 to 0.2 C, in considering that the non-aqueous secondary battery 1 is stabilized by decomposition of a part of the electrolyte solution in the first-time charging, and to make effectively exerted this stabilization effect. It also provides a preferable result that the first-time charging is carried out via constant-voltage charging on the way. Constant current under which rated capacity is discharged for one hour is defined as 1 C. By setting a retention time longer in a voltage range (where the lithium salt is involved in an electrochemical reaction), SEI (Solid Electrolyte Interface) is formed on the electrode surface, suppression effect of increase in internal resistance including the positive electrode 5 is provided, as well as good effect is provided also to the members other than the negative electrode 6 (for example, the positive electrode 5, the separator 7, etc.) in some form or other, without firmly immobilizing reaction Products only at the negative electrode 6. Accordingly, it is very effective to carry out the first-time charging in consideration of the electrochemical reaction of the lithium salt dissolved in the non-aqueous electrolyte solution.

The non-aqueous secondary battery 1 in the present embodiments can be also used as a battery pack where a plurality of the non-aqueous secondary batteries 1 are connected in series or in parallel. It is preferable that use voltage range per one battery is 2 to 5 V, more preferable 2.5 to 5 V and particularly 2.75 to 5 V, in view of management of a charge-discharge state of the battery pack.

Explanation was given above on the aspects for carrying out the present invention; however, the present invention should not be limited to the embodiments. Various modifications of the present invention are possible within a range not to depart from the gist thereof.

EXAMPLES

Explanation will be given in detail below on the present invention, based on Examples; however, the present invention should not be limited to these Examples.

Various types of evaluations were carried out as follows.
(1) Positive Electrode Immersion Test An aluminum laminate bag was fabricated to a size of 2.7 cm×6 cm. Into this bag, the positive electrode cut out to a size of 23 mm×17 mm, as described later, was included, and then 0.5 mL of the non-aqueous electrolyte solution prepared in each Example and Comparative Example was poured under inert atmosphere. At this time, it was confirmed that electrode surface was immersed in the electrolyte solution. After pouring the solution, the aluminum laminated bag was sealed, maintained at 60° C. in a longitudinally standing state, and stored for 10 days. After the storage, observation of the electrolyte solution and the surface of the positive electrode inside the bag was carried out. The case, where a gel-like substance, having a salt of complex cations composed of a transition metal and acetonitrile as a main component, was not confirmed both in the electrolyte solution and at the surface of the positive electrode, was judged test result "good", and the case, where the gel-like substance was confirmed either of in the electrolyte solution and at the surface of the positive electrode, was judged test result "poor".

(2-1) Preparation of Single Layered Laminate-Type Battery
(2-1-1) Preparation of Positive Electrode (P1)

A composite oxide of lithium, nickel, manganese and cobalt ($LiNi_{1/3}Mn_{1/3}Co_{1/3}O_2$, density: 4.70 g/cm$^3$) having a number average particle diameter of 11 μm, as a positive electrode active material, acetylene black powder (density: 1.95 g/cm$^3$), having a number average particle diameter of 48 nm, as a conductive auxiliary agent, and polyvinylidene fluoride (PVdF; density: 1.75 g/cm$^3$), as a binder, were mixed in a mass ratio of 93:4:3 to obtain a positive electrode mixture. To the resulting positive electrode mixture, N-methyl-2-pyrrolidone was added, as a solvent, and further mixed to prepare positive electrode mixture-containing slurry. This positive electrode mixture-containing slurry was coated on one surface of an aluminum foil having a thickness of 20 μm, and a width of 200 mm, as a positive electrode current collector, by adjusting a base weight to 22 mg/cm$^2$, by a doctor blade method, and the solvent was dried and removed. After that, the positive electrode (P1) composed of the positive electrode active material layer and the positive electrode current collector was obtained by rolling them using a roll press, so as to attain a density of the positive electrode active material layer of 2.8 g/cm$^3$.

(2-1-2) Preparation of Negative Electrode (N1)

Graphite carbon powder (trade name "MCMB25-28", produced by Osaka Gas Chemical Co., Ltd.), having a number average particle diameter of 25 μm, as a negative electrode active material, acetylene black, having a number average particle diameter of 48 nm, as a conductive auxiliary agent, and polyvinylidene fluoride (PVdF; density: 1.75 g/cm$^3$), as a binder, were mixed in a solid content mass ratio of 93:2:5. To the resulting mixture, N-methyl-2-pyrrolidone was added, and further mixed to prepare slurry containing the negative electrode mixture. This negative electrode mixture-containing slurry was coated on one surface of a copper foil having a thickness of 10 μm, and a width of 200 mm, as the negative electrode current collector, by adjusting a base weight to 12 mg/cm$^2$, by a doctor blade method and the solvent was removed by drying. After that, the negative electrode (N1) composed of the negative electrode active material layer and the negative electrode current collector was obtained by rolling them using a roll press, so as to attain a density of the negative electrode active material layer of 1.5 g/cm$^3$.

(2-1-3) Preparation of Single-Layered Laminate-Type Battery (for Evaluation)

Two sheets of laminated films (without drawing, thickness: 120 μm, size: 31 mm×37 mm), where an aluminum layer and a resin layer were laminated, were overlapped with the aluminum layer side outward, and three sides thereof were sealed to prepare a laminated cell outer package. The positive electrode (P1) prepared as above was cut out to a size of 14.0 mm×20.5 mm, and the negative electrode (N1) prepared as above was cut out to a size of 14.5 mm×20.5 mm. Subsequently, a polyethylene microporous membrane (membrane thickness: 20 μm, size: 16 mm×22 mm) was prepared, as a separator, and the laminated structure, where the positive electrode (P1) and the negative electrode (N1) were overlapped at both sides of the separator, was arranged inside the laminated cell outer package. Next, the electrolyte solution prepared in each Example and Comparative Example was poured inside the cell outer package, and the laminated structure was soaked in the electrolyte solution. Then, the remaining one side of the laminated cell outer package was sealed to prepare a non-aqueous secondary battery (a single-layered laminate-type battery, hereafter it may also be referred to simply as "battery".). By maintaining this at 25° C. for 24 hours and sufficiently soaking the electrolyte solution to the laminated structure, a single-layered laminate-type battery (SL1), providing 1 C=9 mA, was obtained.

Here, 1 C means current value where a full charged state battery is expected to discharge completion for one hour in discharging under constant current. As for the single-layered laminate-type battery prepared above, it means current value where from a 4.2 V full charged state to discharge completion for one hour by discharging to 2.7 V, under constant current, is expected.

(2-2) Preparation of Multi-Layered Laminate-Type Battery
(2-2-1) Preparation of Positive Electrode (P2)

$LiNi_{0.5}Co_{0.2}Mn_{0.3}O_2$, in 96.8 parts by mass, as a positive electrode active material, 2 parts by mass of acetylene black, as a conductive auxiliary agent, 1 part by mass of polyvinylidene fluoride, as a binder, and 0.2 part by mass of polyvinyl pyrrolidone, as a dispersing agent, were mixed, and further suitable amount of N-methyl pyrrolidone was added to the mixture, to carry out mixing and dispersing the mixture using a planetary mixer so as to obtain a positive electrode mixture-containing slurry. This positive electrode mixture-containing slurry was coated on both surfaces of a sheet of aluminum foil (current collector) having a thickness of 15 μm, vacuum dried at 120° C. for 12 hours to form a positive electrode mixture layers at both surfaces of the sheet of aluminum foil. Then, after adjusting density of the positive electrode mixture layer to 3.15 g/cm$^3$ by carrying out press processing, it was cut into a predetermined size to obtain a belt-shaped positive electrode. In coating the positive electrode mixture-containing paste on the sheet of aluminum foil, a non-coated region was formed, so that a part of the aluminum foil is exposed. At this time, the rear area corresponding to the coated region at the front surface was also the coated region. Thickness of the positive electrode mixture layer of the resulting positive electrode (thickness per one surface of the sheet of aluminum foil, as the positive electrode current collector) was 63 μm, and coated amount (coated amount per one surface of the sheet of aluminum foil, as the positive electrode current collector) was 15.0 mg/cm$^2$.

Figure 5:
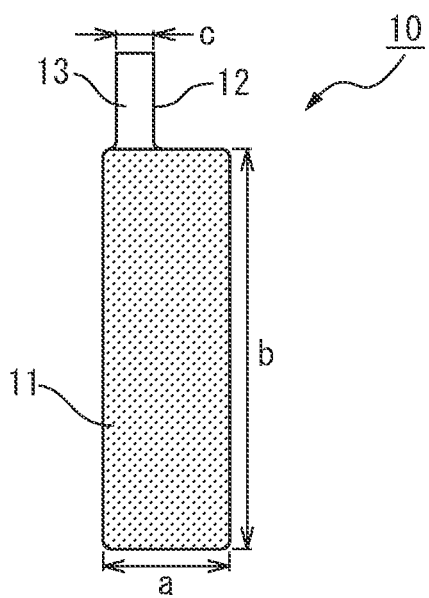
FIG. 5 is a schematic plan view explaining a positive electrode for a battery.

The belt-shaped positive electrode was cut out using a Thomson blade, so that the exposed part of the aluminum foil (positive electrode current collector) is partially protruded, and a formed part of the positive electrode mixture layer is nearly square shape having a curved shape at the four corners to obtain the positive electrode for a battery (P2) having the positive electrode mixture layer on both surfaces of the positive electrode current collector. Here the protruded and exposed part of the aluminum foil functions as a tab part. FIG. 5 shows a plan view schematically representing the positive electrode for a battery. However, size ratio of the positive electrode shown in FIG. 5 is not necessarily coincident with the practical product, to make a structure of the positive electrode easily understandable.

The positive electrode 10 is a shape having the tab part 13, cut out so that a part of the exposed part of the positive electrode current collector 12 is protruded, and a shape of the formation part of the positive electrode mixture layer 11 is nearly square having a curved shape at the four corners, and each length of a, b, and c in the Fig. is 80 mm, 200 mm, and 20 mm, respectively.

(2-2-2) Preparation of Negative Electrode (N2)

Graphite, in 97.5 parts by mass, as a negative electrode active material; and 1.5 parts by mass of carboxymethyl cellulose, and 1.0 part by mass of styrene-butadiene latex, as a binder; were mixed, and further suitable amount of water was added to the mixture and sufficiently mixed to prepare a negative electrode mixture-containing slurry. The negative electrode mixture-containing slurry was coated on both surfaces of a sheet of copper foil (current collector) having thickness of 10 µm, and dried to form a negative electrode mixture layers at both surfaces of the sheet of copper foil. Then, after adjusting density of the negative electrode mixture layer to 1.55 g/cm$^3$ by carrying out press processing, it was cut into a predetermined size to obtain a belt-shaped negative electrode. In coating the negative electrode mixture-containing paste on the sheet of copper foil, a non-coated region was formed, so that a part of the copper foil is exposed. At this time, the rear area corresponding to the coated region at the front surface was also the coated region. Thickness of the negative electrode mixture layer of the resulting negative electrode (thickness per one surface of the sheet of copper foil, as the negative electrode current collector) was 69 µm, and coated amount (coated amount per one surface of the sheet of copper foil, as the negative electrode current collector) was 9.0 mg/cm$^2$.

The belt-shaped negative electrode was cut out using a Thomson blade, so that the exposed part of the copper foil (negative electrode current collector) is partially protruded, and a formed part of the negative electrode mixture layer is nearly square shape having a curved shape at the four corners to obtain the negative electrode for a battery (N2) having the negative electrode mixture layer on both surfaces of the negative electrode current collector. Here, the protruded and exposed part of the copper foil functions as a tab part.

Figure 6:
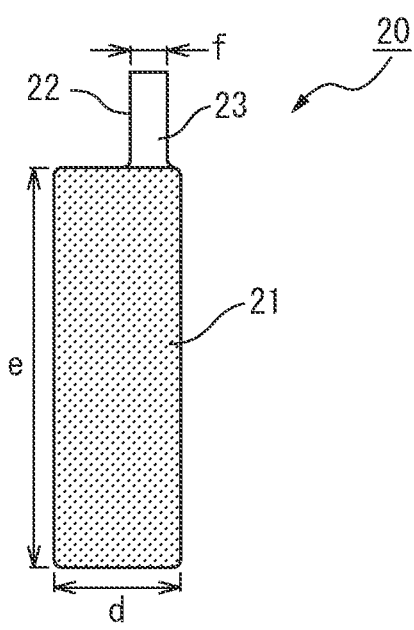
FIG. 6 is a schematic plan view explaining a negative electrode for a battery.

FIG. 6 shows a plan view schematically representing the negative electrode for a battery. However, size ratio of the negative electrode shown in FIG. 6 is not necessarily coincident with the practical product, to make a structure of the negative electrode easily understandable.

The negative electrode 20 is a shape having the tab part 23, cut out so that a part of the exposed part of the negative electrode current collector 22 is protruded, and a shape of the formation part of the negative electrode mixture layer 21 is nearly square having a curved shape at the four corners, and each length of d, e, and f in the Fig. is 85 mm, 205 mm, and 20 mm, respectively.

(2-2-3) Preparation of Multi-Layered Laminate-Type Battery

A laminated electrode structure was formed using 20 pieces of the positive electrodes for a battery (P2) formed with the positive electrode mixture layer on both surfaces of the positive electrode current collector, and 21 pieces of the negative electrodes for a battery (N2) formed with the negative electrode mixture layer on both surfaces of the negative electrode current collector. The laminated electrode structure uses the negative electrode for a battery, as both of the upper and lower ends, and alternatively arranges the positive electrode for a battery and the negative electrode for a battery between the upper and lower ends by interposing a separator (a separator made of a microporous polyethylene film; a thickness of 20 µm), and tab parts of both positive electrodes and tab parts of both negative electrodes were each welded.

Next, an aluminum laminated film having a thickness of 150 µm, a width of 130 mm, and a height of 230 mm, was shaped to have a pit such that the laminated electrode structure can be accommodated in the aluminum laminated film. The laminated electrode structure was inserted into the pit, and another aluminum laminated film (not formed with a pit) having the same size as the above film was put thereon to heat-weld at the three sides of both of the aluminum laminated films. Then, the non-aqueous electrolyte solution was poured from the remaining one side of both aluminum laminated films. After that, a multi-layered laminate-type non-aqueous secondary battery (hereafter it may also be referred to simply as "multi-layered laminate-type battery") was prepared by heat-sealing the remaining one side of both aluminum laminated films under vacuum. This multi-layered laminate-type battery has a rated current value of 15 Ah, and a rated voltage value of 4.2 V.

Each positive electrode of the laminated electrode structure was integrated by welding both tab parts, and the integrated part of the welded tab parts was connected with a positive electrode external terminal inside the battery. Similarly, each negative electrode of the laminated electrode structure was also integrated by welding both tab parts, and the integrated part of the welded tab parts was connected with a negative electrode external terminal inside the battery. The positive electrode external terminal and the negative electrode external terminal were drawn at one terminal side to the outside of the outer packaging structure using aluminum laminated films, so as to be connectable with an external device, etc.

(3) Battery Evaluation of Single-Layered Laminate-Type Battery

As for the single-layered laminate-type battery obtained as above, firstly the first-time charging processing and measurement of the first-time charge-discharge capacity were carried out, according to a procedure of the following (3-1). Next, each single-layered laminate-type battery was evaluated, according to procedures of the following (3-2) and (3-3). Charge-discharge was carried out using a charge-discharge apparatus ACD-01 (trade name, manufactured by Asuka Electronics Co., Ltd.) and a constant temperature chamber PLM-63S (trade name, manufactured by Hutaba K.K. Co., Ltd.).

(3-1) First-Time Charge-Discharge Processing of Single-Layered Laminate-Type Battery The single-layered laminate-type battery was charged till attaining a battery voltage of 4.2 V under a constant current of 1.8 mA corresponding to 0.2 C, by setting an ambient temperature of the single-layered laminate-type battery at 25° C., and then charged under a constant voltage of 4.2 V for 8 hours. After that, it was discharged to 2.7 V, under a constant current of 1.8 mA corresponding to 0.2 C. The first-time efficiency was calculated by dividing discharge capacity at this time with charge capacity. In addition, discharge capacity this time was defined as initial capacity.

(3-2) Discharge Capacity Measurement, Under High Rate, of Single-Layered Laminate-Type Battery (Load Test)

Using the battery, which had been first-time charge-discharge processed by the method described in the above item (3-1), charging was carried out up to a battery voltage of 4.2 V under a constant current of 9 mA corresponding to 1 C, and then charging was carried under a constant voltage of 4.2 V for 3 hours in total. After that, it was discharged to a battery voltage of 2.7 V, under a constant current of 9 mA corresponding to 1 C. Discharge capacity at this time was defined as "A". Next, after charging up to a battery voltage of 4.2 V under a constant current of 9 mA corresponding to 1 C, charging was carried out under a constant voltage of 4.2 V for 3 hours in total. After that, discharge was carried out to a battery voltage of 2.7 V under a constant current of 45 mA corresponding to 5 C. Discharge capacity at this time was defined as "B". The following value was calculated as load test measurement value.

Capacity retention rate=100×B/A [%]

(3-3) 50° C. Cycle Measurement of Single-Layered Laminate-Type Battery

As for the battery, which had been subjected to the first-time charge-discharge processing by the method described in the above item (3-1), charge-discharge cycle characteristics at 50° C. was evaluated.

Firstly, ambient temperature of the single-layered laminate-type battery was set at 50° C. After attaining 4.2 V by charging under constant current corresponding to 1 C, charging was carried out at 4.2 V for 3 hours in total, and subsequently, discharging was carried out to 2.7 V under constant current corresponding to 1 C. By defining the step for carrying out charging and discharging each one time, as one cycle, 100 cycles of charge-discharge were carried out. In addition, discharges at the $1^{st}$, $50^{th}$ and $100^{th}$ times were carried out under constant current corresponding to 0.3 C, instead of 1 C.

At this time, discharge capacity rate of each cycle, relative to discharge capacity at the $2^{nd}$ time, as 100%, was defined as discharge capacity retention rate.

(3-4) A.C. Impedance Measurement of Single-Layered Laminate-Type Battery

Measurement of A.C. impedance was carried out using Frequency Response Analyzer 1400 (trade name), manufactured by Solartron Metrology Co., Ltd., and Potentio-Galvanostat 1470E (trade name), manufactured by Solartron Metrology Co., Ltd. As the non-aqueous secondary battery to be measured, the single-layered laminate-type battery was used, after charging of 1 cycle, 50 cycles and 100 cycles, in carrying out cycle measurement at 50° C. by the method described in the above item (3-3). In this measurement, only one battery was used, and after carrying out measurement after charging at cycle of each predetermined times, cycle measurement at 50° C. was continued to be provided to the next-time measurement.

As measurement conditions, amplitude and frequency were set at ±5 mV, and 0.1 to 20 kHz, respectively to determine A.C. impedance value at 20 kHz and 0.1 Hz. Ambient temperature of the battery in measurement of A.C. impedance was 25° C.

(4) Battery Evaluation of Multi-Layered Laminate-Type Battery

As for the multi-layered laminate-type battery obtained as above, firstly output characteristics was evaluated, according to a procedure of the following (4-1). Next, charge-discharge DCR (direct current internal resistance) and charge-discharge cycle characteristics were evaluated, according to procedures of the following (4-2) and (4-3).

(4-1) Output Characteristics (Discharge Capacity Retention Rate)

As for the multi-layered laminate-type battery obtained in each Example and Comparative Example, constant current charging was carried out to 4.2 V at 23° C. under a current value of 0.2 C, and then constant voltage charging was carried out at 4.2 V till attaining a current value of 0.1 C to measure charge capacity (0.2 C charge capacity). Next, as for the multi-layered laminate-type battery after the charging, discharging was carried out under constant current at a current value of 0.2 C, till attaining 2.5 V to measure discharge capacity (0.2 C discharging capacity) at this time.

Next, as for the multi-layered laminate-type battery after measurement of the 0.2 C discharge capacity, constant current-constant voltage charging, and constant current discharging were carried out under the same conditions as in the 0.2 C charge-discharge capacity measurement, except for changing current value in constant current charging and constant current discharging to each 2 C.

Then, discharge capacity retention rate was obtained, as a value obtained by dividing 0.2 C discharge capacity with 2 C discharge capacity and is shown in percentage.

(4-2) Load Test (Measurement of Charge-Discharge DCR (Direct Current Internal Resistance))

As for the multi-layered laminate-type battery obtained in each Example and Comparative Example, constant current charging was carried out at 25° C. for 30 minutes under a current value of 1 C, and then discharged for 10 seconds under a current value of 1 C to measure voltage decreased for 10 seconds from start of the discharge: $\Delta V_1$.

Next, constant current charging under the above condition and constant current discharging under a current value of 2 C were carried out in this order to similarly measure voltage decreased for 10 seconds from start of discharge under a constant current of 2 C: $\Delta V_2$, and DCR was calculated by the following equation.

DCR (mΩ)=($\Delta V_2$-$\Delta V_1$)/(current value of 2 C−current value of 1 C)

(4-3) Charge-Discharge Cycle Characteristics

As for the multi-layered laminate-type battery obtained in each Example and Comparative Example, after carrying out charging to 4.2 V under constant current at a current value of 2 C at 23° C., charge-discharge was repeated, by defining a series of operations of charging carried out under a constant voltage of 4.2 V till attaining a current value of 0.1 C, and discharging carried out under constant current with a current value of 2 C till attaining 2.5 V, as one cycle, to calculate capacity retention rate at 100 cycles by the following equation.

Capacity retention rate (%)=(discharge capacity at 100 cycles/discharge capacity at 1 cycle)×100

(5) Preparation of Electrolyte Solution

Under inert atmosphere, various types of non-aqueous solvents and various types of electrode protection additives were mixed, so that each attains predetermined concentration, and further various types of lithium salts were added, so that each attains predetermined concentration to prepare electrolyte solutions (S11) to (S22). Compositions of these electrolyte solutions are shown in TABLE 1.

In addition, various types of the nitrogen-containing cyclic compounds are added, so as to attain predetermined parts by mass, relative to 100 parts by mass of these electrolyte solutions, as original electrolyte solutions to prepare electrolyte solutions (S31) to (S66). Compositions of these electrolyte solutions are shown in TABLE 2.

TABLE 1

| Electrolyte solution No. | Composition of non-aqueous electrolyte solution [% by volume] | | | | | | | | Lithium salt [Mol number relative to 1 L of non-aqueous solvent] | | |
|---|---|---|---|---|---|---|---|---|---|---|---|
| | AN | EC | PC | EMC | DEC | VC | ES | PS | $LiPF_6$ | LiBOB | LiTFSI |
| S11 | 83 | — | — | — | — | 17 | — | — | 1.3 | 0.1 | — |
| S12 | 47 | — | — | — | 38 | 11 | 4 | — | 1.3 | 0.1 | — |
| S13 | 47 | — | 38 | — | — | 11 | 4 | — | 1.3 | 0.1 | — |
| S14 | 47 | — | 38 | — | — | 11 | — | 4 | 1.3 | 0.1 | — |
| S15 | 60 | 25 | — | — | — | 10 | 3 | — | 1.2 | — | — |
| S16 | 50 | 50 | — | — | — | — | — | — | 1.0 | — | — |
| S17 | 30 | 60 | — | — | — | 10 | — | — | 0.3 | 0.1 | 2.0 |
| S18 | 50 | — | — | — | 40 | 10 | — | — | 1.3 | 0.1 | — |
| S19 | 100 | — | — | — | — | — | — | — | 1.0 | — | — |
| S20 | 100 | — | — | — | — | — | — | — | — | 1.0 | — |
| S21 | 100 | — | — | — | — | — | — | — | — | — | 1.0 |
| S22 | — | 30 | — | 70 | — | — | — | — | 1.0 | — | — |

TABLE 2

| Electrolyte solution No. | original-electrolyte solution No. | Nitrogen-containing cyclic compound Type | Addition amount [parts by mass] |
|---|---|---|---|
| S31 | S11 | 1,2,3-benzotriazole | 1.0 |
| S32 | S11 | 5-methyl-1H-benzotriazole | 1.0 |
| S33 | S11 | 1-(trimethylsilyl)-1H-benzotriazole | 1.0 |
| S34 | S11 | benzotriazole-1-yl-acetoacetic acid ethyl ester | 1.0 |
| S35 | S11 | 1-benzyl-1H-benzotriazole | 1.0 |
| S36 | S11 | 5-(trifluoromethyl)-1H-benzotriazole | 1.0 |
| S37 | S11 | 1-(pyrrolydinylmethyl)-1H-benzotriazole | 1.0 |
| S38 | S11 | 1-(methylsulfonyl)-1H--benzotriazole | 1.0 |
| S39 | S11 | 1H-benzotriazole-1-sulfonyl azide | 1.0 |
| S40 | S11 | benzoimidazole | 0.5 |
| S41 | S11 | 1-benzyl-1H-benzoimidazole-2-yl amine | 1.0 |
| S42 | S12 | 1-methyl-1H-benzotriazole | 1.0 |
| S43 | S12 | 1-methylbenzoimidazole | 1.0 |
| S44 | S13 | 1-amino-1H-benzotriazole | 1.0 |
| S45 | S13 | 4-methyl-1H-benzotriazole | 0.5 |
| S46 | S13 | 5-methylbenzoimidazole | 0.5 |
| S47 | S13 | 5-aminobenzoimidazole | 0.5 |
| S48 | S14 | 1-methyl-1H-benzotriazole-4-amine | 1.0 |
| S49 | S14 | 1-(2,2-dichloroacetyl)-1H-benzotriazole | 1.0 |
| S50 | S14 | 1H-benzotriazole-1-yl methylisocyanide | 1.0 |
| S51 | S15 | 5-nitrobenzotriazole | 0.5 |
| S52 | S15 | 5,6-dimethylbenzoimidazole | 1.0 |
| S53 | S15 | 5-nitrobenzoimidazole | 0.5 |
| S54 | S16 | 1-propargyl-1H-benzotriazole | 1.0 |
| S55 | S16 | 1-cyanobenzoimidazole | 0.5 |
| S56 | S17 | 5-chlorobenzotriazole | 0.5 |
| S57 | S17 | 5-chlorobenzoimidazole | 0.5 |
| S58 | S18 | 1-(chloromethyl)-1H-benzotriazole | 1.0 |
| S59 | S18 | 4,5,6,7-tetrabromobenzotriazole | 1.0 |
| S60 | S13 | 1-[N,N-bis(2-ethylhexyl)aminomethyl]benzotriazole | 1.5 |
| S61 | S13 | 1-[N,N-bis(2-ethylhexyl)aminomethyl]methylbenzotriazole | 2.0 |
| S62 | S12 | 1-methyl-1H-benzotriazole | 0.5 |
| S63 | S12 | 1-methyl-1H-benzotriazole | 0.25 |
| S64 | S12 | 1-methyl-1H-benzotriazole | 0.1 |
| S65 | S12 | 1-methyl-1H-benzotriazole | 0.05 |
| S66 | S12 | 1-methyl-1H-benzotriazole | 0.01 |

Abbreviations of the non-aqueous solvents and the lithium salts in TABLE 1 each have the following meanings:
(Non-Aqueous Solvents)
  AN: acetonitrile
  EC: ethylene carbonate
  PC: propylene carbonate
  EMC: ethyl methyl carbonate
  DEC: diethyl carbonate
  VC: vinylene carbonate
  ES: ethylene sulfite
  PS: 1,3-propane sultone
(Lithium Salts)
  $LiPF_6$: lithium hexafluorophosphate
  LiBOB: lithium bis(oxalate)borate ($LiB(C_2O_4)_2$)
  LiTFSI: lithium bis(trifluoromethanesulfonyl)imide ($LiN(SO_2CF_3)_2$)

Comparative Examples 1 to 9, Reference Examples 1 to 2, and Examples 1 to 31

As for various types of electrolyte solutions obtained as above, the positive electrode immersion test was carried out by the method described in the above item (1). The resulting evaluation results are shown in TABLE 3.

TABLE 3

| | Electrolyte solution No. | Positive electrode immersion test |
|---|---|---|
| Comparative Ex. 1 | S11 | poor |
| Comparative Ex. 2 | S12 | poor |
| Comparative Ex. 3 | S13 | poor |
| Comparative Ex. 4 | S14 | poor |
| Comparative Ex. 5 | S15 | poor |
| Comparative Ex. 6 | S16 | poor |
| Comparative Ex. 7 | S17 | poor |
| Comparative Ex. 8 | S18 | poor |
| Comparative Ex. 9 | S19 | poor |

TABLE 3-continued

| | Electrolyte solution No. | Positive electrode immersion test |
|---|---|---|
| Ref. Ex. 1 | S20 | good |
| Ref. Ex. 2 | S21 | good |
| Ex. 1 | S31 | good |
| Ex. 2 | S32 | good |
| Ex. 3 | S33 | good |
| Ex. 4 | S34 | good |
| Ex. 5 | S35 | good |
| Ex. 6 | S36 | good |
| Ex. 7 | S37 | good |
| Ex. 8 | S38 | good |
| Ex. 9 | S39 | good |
| Ex. 10 | S40 | good |
| Ex. 11 | S41 | good |
| Ex. 12 | S42 | good |
| Ex. 13 | S43 | good |
| Ex. 14 | S44 | good |
| Ex. 15 | S45 | good |
| Ex. 16 | S46 | good |
| Ex. 17 | S47 | good |
| Ex. 18 | S60 | good |
| Ex. 19 | S61 | good |
| Ex. 20 | S48 | good |
| Ex. 21 | S49 | good |
| Ex. 22 | S50 | good |
| Ex. 23 | S51 | good |
| Ex. 24 | S52 | good |
| Ex. 25 | S53 | good |
| Ex. 26 | S54 | good |
| Ex. 27 | S55 | good |
| Ex. 28 | S56 | good |
| Ex. 29 | S57 | good |
| Ex. 30 | S58 | good |
| Ex. 31 | S59 | good |

In the electrolyte solution containing the fluorine-containing inorganic lithium salt and acetonitrile, generation of a dark brown gel-like substance was confirmed in Comparative Example 1 to Comparative Example 9 not containing the nitrogen-containing cyclic compound. This gel-like substance has been revealed, from analysis result, to contain complex cations composed of a transition metal and acetonitrile. On the other hand, in the electrolyte solution containing the fluorine-containing inorganic lithium salt and acetonitrile, generation of this dark brown gel-like substance was not confirmed in Example 1 to Example 31, containing the nitrogen-containing cyclic compound.

From these results, it has been suggested that the nitrogen-containing cyclic compound contributes to high-temperature durability of a battery, in the electrolyte solution containing the fluorine-containing inorganic lithium salt and acetonitrile.

In addition, in Reference Example 1 and Reference Example 2, where only an organic lithium salt was used as lithium ions, generation of the dark brown gel-like substance was not confirmed. From this fact, it has been suggested that generation of the dark brown gel-like substance is a problem specific to the electrolyte solution containing the fluorine-containing inorganic lithium salt, and acetonitrile.

Examples 32 and 33, as well as Comparative Example 10

A single-layered laminate-type battery was prepared, according to the method described in the above item (2-1-3), by combining the positive electrode (P1), the negative electrode (N1), and the electrolyte solutions described in TABLE 4. As for this single-layered laminate-type battery, first-time charge-discharge processing was carried out by the method described in the above item (3-1), and discharge capacity measurement was carried out by the method described in the above item (3-2). Capacity retention rate in this load test is shown in TABLE 4.

TABLE 4

| | Electrolyte solution No. | Initial charge-discharge First-time efficiency [%] | Load test capacity retention rate [%] |
|---|---|---|---|
| Ex. 32 | S31 | 86.0 | 80.3 |
| Ex. 33 | S46 | 83.5 | 56.8 |
| Comparative Ex. 10 | S22 | 83.2 | 6.6 |

From comparison of Example 32 and Example 33 and Comparative Example 10, it has been confirmed that capacity retention rate in the load test is significantly enhanced in the case of using the electrolyte solution containing acetonitrile, as compared with the case of using the electrolyte solution not containing acetonitrile.

Examples 34 to 40, and Comparative Example 11

A single-layered laminate-type battery was prepared, according to the method described in the above item (2-1-3), by combining the positive electrode (P1), the negative electrode (N1) prepared as above, and the electrolyte solutions described in TABLE 5. As for this single-layered laminate-type battery, first-time charge-discharge processing was carried out by the method described in the above item (3-1), and cycle measurement at 50° C. and A.C. impedance measurement were carried out by the method described in the above items (3-3) and (3-4). Evaluation results are shown in TABLE 5.

TABLE 5

| | Electrolyte solution No. | Initial charge-discharge First-time efficiency [%] | 50° C. cycle measurement Charge-discharge capacity retention rate [%] | | AC impedance [Ω] | | | | |
|---|---|---|---|---|---|---|---|---|---|
| | | | | | 1 cycle | | 50 cycles | | 100 cycles | |
| | | | 49 cycles | 99 cycles | 20 kHz | 0.1 Hz | 20 kHz | 0.1 Hz | 20 kHz | 0.1 Hz |
| Ex. 34 | S42 | 86.3 | 84.6 | 71.5 | 0.77 | 3.61 | 3.00 | 17.25 | 3.75 | 30.06 |
| Ex. 35 | S62 | 86.8 | 83.6 | 70.9 | 1.02 | 4.03 | 3.65 | 20.99 | 4.64 | 31.39 |
| Ex. 36 | S63 | 85.7 | 85.2 | 74.0 | 0.98 | 3.87 | 3.03 | 17.30 | 3.92 | 27.04 |
| Ex. 37 | S64 | 86.4 | 86.0 | 73.7 | 0.98 | 3.90 | 3.14 | 15.10 | 4.01 | 25.79 |
| Ex. 38 | S65 | 87.2 | 86.0 | 75.0 | 0.87 | 3.89 | 3.10 | 14.92 | 4.00 | 25.74 |

TABLE 5-continued

| | Electrolyte solution No. | Initial charge-discharge First-time efficiency [%] | 50° C. cycle measurement Charge-discharge capacity retention rate [%] | | AC impedance [Ω] | | | | | |
|---|---|---|---|---|---|---|---|---|---|---|
| | | | | | 1 cycle | | 50 cycles | | 100 cycles | |
| | | | 49 cycles | 99 cycles | 20 kHz | 0.1 Hz | 20 kHz | 0.1 Hz | 20 kHz | 0.1 Hz |
| Ex. 39 | S66 | 87.3 | 86.1 | 75.1 | 0.94 | 3.80 | 3.56 | 16.30 | 4.13 | 29.41 |
| Ex. 40 | S43 | 85.4 | 82.4 | 64.3 | 0.91 | 4.19 | 3.40 | 16.89 | 4.19 | 49.87 |
| Comparative Ex. 11 | S12 | 86.8 | 74.8 | 24.3 | 0.80 | 3.21 | 5.23 | 28.02 | 18.68 | 339.72 |

From comparison of Examples 34 to 40, and Comparative Example 11, it has been confirmed that the case of using the electrolyte solution containing acetonitrile, the fluorine-containing inorganic lithium salt and the nitrogen-containing cyclic compound is superior in 50° C. cycling performance, as compared with case of using the electrolyte solution not containing the nitrogen-containing cyclic compound, and is also capable of suppressing increase in internal resistance upon repeated charge-discharge cycles.

Example 41

A multi-layered laminate-type battery was prepared, according to the method described in the above item (2-2-3), by combining the positive electrode (P2), the negative electrode (N2) prepared as above, and the electrolyte solution (S64). As for this multi-layered laminate-type battery, the output characteristics (discharge capacity retention rate) test, the load test (charge-discharge DCR measurement), and the charge-discharge cycle characteristics test were carried out by the methods described in the above items (4-1) to (4-3). Evaluation results are shown in TABLE 6.

Comparative Example 12

A multi-layered laminate-type battery was prepared similarly as in Example 41, except for using the electrolyte solution (S12). As for this multi-layered laminate-type battery, firstly, the first-time charging was started by the method described in the above item (4-1); however, test continuation was abandoned due to generation of swelling gas.

evaluation. It has been confirmed that the multi-layered laminate-type battery of Example 41 shows cycling performance equivalent to that of a small-size single-layered laminate battery.

From the above results, it has been revealed that the non-aqueous secondary battery using the electrolyte solution of the present embodiment attains extremely high rate characteristic, while maintaining high-temperature durability performance comparable to an existing electrolyte solution.

INDUSTRIAL APPLICABILITY

The non-aqueous secondary battery prepared by using the non-aqueous electrolyte solution of the present invention is expected to be utilized as a battery for a mobile device, for example, a mobile phone, a mobile audio device, a personal computer, IC (Integrated Circuit) tag, etc.; an automotive battery for a hybrid car, a plug-in hybrid car, an electric car, etc.; a storage system for housing; etc.

LIST OF SYMBOLS

1 non-aqueous secondary battery
2 battery outer package
3 positive electrode external terminal
4 negative electrode external terminal
5 positive electrode
5A positive electrode active material layer
5B positive electrode current collector
6 negative electrode

TABLE 6

| | Composition of non-aqueous electrolyte solution [mL] | | | | Mol number relative to 1 L of non-aqueous solvent | | Additives | | Initial charge-discharge First-time efficiency [%] | Load test | | | Cycle test Capacity retention rate [%] |
|---|---|---|---|---|---|---|---|---|---|---|---|---|---|
| | | | | | | | | | | Discharge capacity retention rate [%] | | | |
| | AN | EC | VC | ES | DEC | LiPF$_6$ | LiBOB | Type | Addition amount [parts by mass*] | | | Discharge DCR [mΩ] | Charge DCR [mΩ] | |
| Ex. 41 | 47 | — | 11 | 4 | 38 | 1.3 | 0.1 | MBTA | 0.1 | 82 | 99 | 2.73 | 2.70 | 86 |

*Addition amount of the additives is amount (parts by mass), relative to 100 parts by mass of parts where the additives are excluded from the total amount of electrolyte solution.

In general, a large capacity multi-layered laminate-type battery tends to generate uneven potential on the electrode surface, and gas generation is a serious problem. However, it has been proved that the multi-layered laminate-type battery of Example 41 operates without any problem and also solves a problem in scale-up, which had not been confirmed in a small-size single-layered laminate battery

6A negative electrode active material layer
6B negative electrode current collector
7 separator
10 positive electrode
11 positive electrode mixture layer
12 positive electrode current collector
13 tab portion 20 negative electrode
21 negative electrode mixture layer
22 negative electrode current collector
23 tab portion

The invention claimed is:

1. A non-aqueous electrolyte solution comprising:
a non-aqueous solvent containing acetonitrile,
LiPF$_6$, and
a compound represented by the following general formula (1):

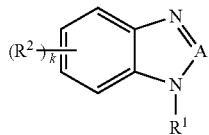

wherein A is a nitrogen atom,
R$^1$ is an alkyl group having 1 to 4 carbon atoms, bis(N, N'-alkyl)aminomethyl group, or bis(N,N'-alkyl)aminoethyl group,
R$^2$ is an alkyl group having 1 to 4 carbon atoms, a fluorine-substituted alkyl group having 1 to 4 carbon atoms, an alkoxy group having 1 to 4 carbon atoms, a fluorine-substituted alkoxy group having 1 to 4 carbon atoms, nitrile group, nitro group, amino group, or a halogen atom, and k is an integer of 0 to 4.

2. The non-aqueous electrolyte solution according to claim 1, wherein the non-aqueous solvent contains acetonitrile in 20 to 100% by volume.

3. The non-aqueous electrolyte solution according to claim 1, wherein content of the compound represented by general formula (1) above is 0.01 to 10 parts by mass, relative to 100 parts by mass of the non-aqueous electrolyte solution.

4. A non-aqueous secondary battery comprising:
a positive electrode having a positive electrode active material layer containing at least one transition metal element selected from Ni, Mn, and Co, on one surface or both surfaces of a current collector;
a negative electrode having a negative electrode active material layer on one surface or both surfaces of another current collector; and
the non-aqueous electrolyte solution according to claim 1.

5. The non-aqueous secondary battery according to claim 4, wherein the positive electrode active material layer and the negative electrode active material layer face each other, and
ratio of the entire area of the surface of the side of the negative electrode active material layer opposing to the positive electrode active material layer, relative to the area of the region where the positive electrode active material layer and the negative electrode active material layer face each other, is larger than 1.0 and below 1.1.

6. The non-aqueous electrolyte solution according to claim 2, wherein content of the compound represented by general formula (1) above is 0.01 to 10 parts by mass, relative to 100 parts by mass of the non-aqueous electrolyte solution.

7. A non-aqueous secondary battery comprising:
a positive electrode having a positive electrode active material layer containing at least one transition metal element selected from Ni, Mn, and Co, on one surface or both surfaces of a current collector;
a negative electrode having a negative electrode active material layer on one surface or both surfaces of another current collector; and
the non-aqueous electrolyte solution according to claim 2.

8. A non-aqueous secondary battery comprising:
a positive electrode having a positive electrode active material layer containing at least one transition metal element selected from Ni, Mn, and Co, on one surface or both surfaces of a current collector;
a negative electrode having a negative electrode active material layer on one surface or both surfaces of another current collector; and
the non-aqueous electrolyte solution according to claim 3.

* * * * *